US012691037B2

(12) United States Patent
Giamo et al.

(10) Patent No.: US 12,691,037 B2
(45) Date of Patent: Jul. 28, 2026

(54) MEDICINAL FLUID DELIVERY DEVICE

(71) Applicant: Takeda Pharmaceutical Company Limited, Osaka (JP)

(72) Inventors: Joseph M. Giamo, Allston, MA (US); Thomas Boyajian, Wilmington, MA (US); Amey Mathakari, Billerica, MA (US); Anh Nguyen, Dover, MA (US); Dhairya Kiritkumar Mehta, Irvine, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 255 days.

(21) Appl. No.: 18/471,533

(22) Filed: Sep. 21, 2023

(65) Prior Publication Data

US 2024/0082111 A1     Mar. 14, 2024

Related U.S. Application Data

(63) Continuation of application No. 17/908,735, filed as application No. PCT/US2021/020997 on Mar. 5, 2021, now Pat. No. 11,793,721.
(Continued)

(51) Int. Cl.
*A61J 1/20*          (2006.01)
*A61M 5/178*        (2006.01)

(52) U.S. Cl.
CPC .......... *A61J 1/2089* (2013.01); *A61J 1/2058* (2015.05); *A61J 1/2082* (2015.05); *A61J 1/2096* (2013.01);
(Continued)

(58) Field of Classification Search
CPC .. A61M 5/1409; A61M 5/1782; A61J 1/2089; A61J 1/201; A61J 1/2096; A61J 1/2058; A61J 1/20
See application file for complete search history.

(56) References Cited

U.S. PATENT DOCUMENTS

| 4,623,343 A | 11/1986 | Thompson |
| 4,994,029 A | 2/1991 | Rohrbough |
(Continued)

FOREIGN PATENT DOCUMENTS

| CN | 101111281 A | 1/2008 |
| CN | 101426465 A | 5/2009 |
(Continued)

OTHER PUBLICATIONS

Extended European Search Report dated Mar. 18, 2024 for European Application No. EP 21763799.0.
(Continued)

*Primary Examiner* — Ariana Zimbouski
(74) *Attorney, Agent, or Firm* — Wolf, Greenfield & Sacks, P.C.

(57)          ABSTRACT
In some embodiments, a reconstitution or medicinal fluid delivery device includes a transfer engine including two fluidly connected spikes, each configured to pierce a container. A check valve may be disposed between the two spikes to allow unidirectional flow from one container to the other. Physical access to a fluid outlet may be obstructed by a housing until the reconstitution or medicinal fluid delivery device is actuated, whereupon physical access to the fluid outlet is permitted. The reconstitution or medicinal fluid delivery device may be placed on a flat surface and actuated with force applied in a single direction toward the flat surface.

12 Claims, 50 Drawing Sheets

Related U.S. Application Data

(60) Provisional application No. 62/985,797, filed on Mar. 5, 2020.

(52) U.S. Cl.
CPC ... *A61M 5/1782* (2013.01); *A61M 2205/3331* (2013.01); *A61M 2205/3368* (2013.01); *A61M 2205/3553* (2013.01); *A61M 2205/3584* (2013.01)

(56) References Cited

U.S. PATENT DOCUMENTS

| | | | |
|---|---|---|---|
| 5,329,976 | A | 7/1994 | Haber et al. |
| 6,213,994 | B1 | 4/2001 | Jansen et al. |
| D1,002,837 | S | 10/2023 | Boyajian et al. |
| 11,793,721 | B2 | 10/2023 | Giamo et al. |
| 2004/0010242 | A1 | 1/2004 | Heyes et al. |
| 2004/0176724 | A1 | 9/2004 | Kamen et al. |
| 2009/0062732 | A1 | 3/2009 | Radmer |
| 2009/0099547 | A1 | 4/2009 | Radmer |
| 2009/0182300 | A1 | 7/2009 | Radmer et al. |
| 2012/0029464 | A1 | 2/2012 | Kragelund et al. |
| 2012/0053555 | A1* | 3/2012 | Ariagno ............... A61J 1/2089 |
| | | | 604/416 |
| 2012/0089088 | A1 | 4/2012 | Foshee et al. |
| 2013/0046270 | A1 | 2/2013 | Foshee et al. |
| 2014/0303556 | A1 | 10/2014 | Travanty |
| 2017/0020784 | A1 | 1/2017 | Schweiss et al. |
| 2018/0110922 | A1* | 4/2018 | Dunki-Jacobs ....... A61J 1/2075 |
| 2018/0204636 | A1 | 7/2018 | Edwards et al. |
| 2019/0009027 | A1 | 1/2019 | Edwards et al. |
| 2019/0125972 | A1 | 5/2019 | Srinivasan et al. |
| 2021/0154097 | A1* | 5/2021 | McLoughlin ......... A61J 1/2006 |
| 2022/0370289 | A1* | 11/2022 | McLoughlin ........... A61J 1/201 |
| 2023/0140678 | A1 | 5/2023 | Giamo et al. |

FOREIGN PATENT DOCUMENTS

| | | | |
|---|---|---|---|
| CN | 108040465 | A | 5/2018 |
| EP | 2 545 833 | A2 | 1/2013 |
| EP | 2934617 | A1 | 10/2015 |
| EP | 3 057 635 | B1 | 12/2019 |
| JP | 2002-529204 | A | 9/2002 |
| JP | 2004-267773 | A | 9/2004 |
| JP | 2004-529739 | A | 9/2004 |
| JP | 2009-534144 | A | 9/2009 |
| JP | 2013-520272 | A | 6/2013 |
| JP | 2013-525004 | A | 6/2013 |
| JP | 2013-544139 | A | 12/2013 |
| JP | 2016-504155 | A | 2/2016 |
| JP | 2016-054805 | A | 4/2016 |
| JP | 2018-509252 | A | 4/2018 |
| JP | 2018-519141 | A | 7/2018 |
| RU | 2077343 | C1 | 4/1997 |
| WO | WO 2005/007223 | A2 | 1/2005 |
| WO | WO 2014/100658 | A1 | 10/2015 |
| WO | WO 2017/147202 | A1 | 8/2017 |
| WO | WO 2019/217864 | A1 | 11/2019 |

OTHER PUBLICATIONS

International Search Report and Written Opinion mailed Jul. 1, 2021 in connection with International Application No. PCT/US2021/020997.

International Preliminary Report on Patentability mailed Sep. 15, 2022 for International Application No. PCT/US2021/020997.

EP 21763799.0, Mar. 18, 2024, Extended European Search Report.

* cited by examiner

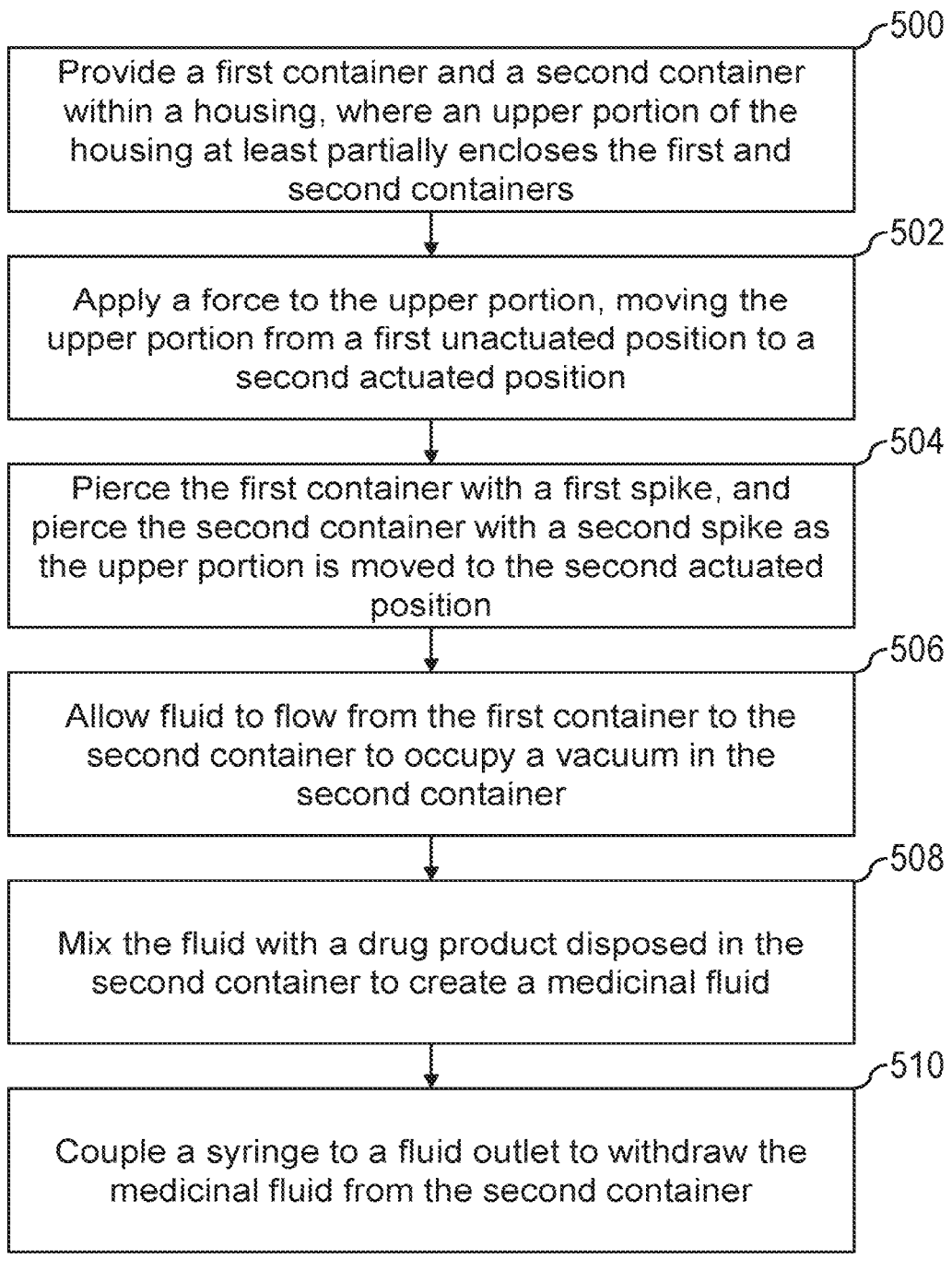

500

Provide a first container and a second container within a housing, where an upper portion of the housing at least partially encloses the first and second containers

502

Apply a force to the upper portion, moving the upper portion from a first unactuated position to a second actuated position

504

Pierce the first container with a first spike, and pierce the second container with a second spike as the upper portion is moved to the second actuated position

506

Allow fluid to flow from the first container to the second container to occupy a vacuum in the second container

508

Mix the fluid with a drug product disposed in the second container to create a medicinal fluid

510

Couple a syringe to a fluid outlet to withdraw the medicinal fluid from the second container

FIG. 15

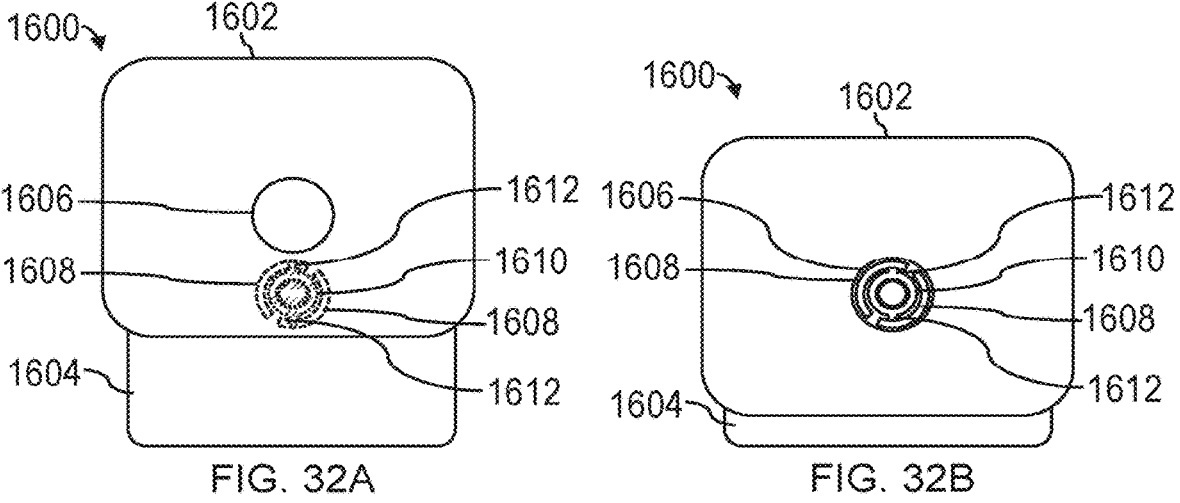
FIG. 32A
FIG. 32B
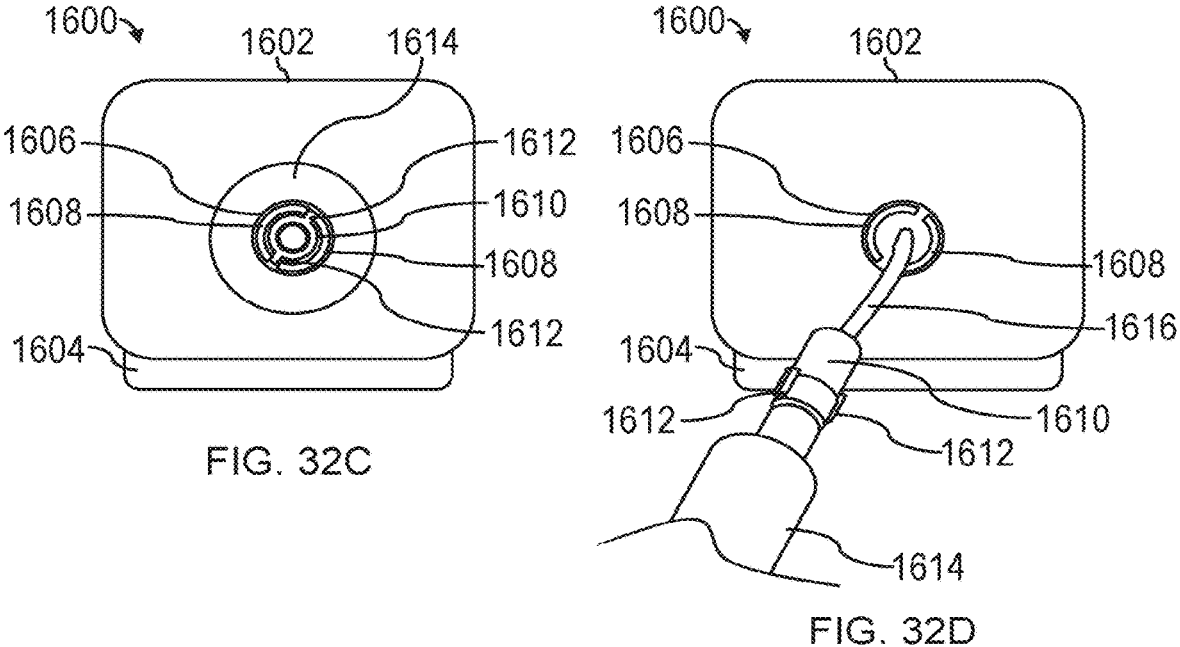
FIG. 32C
FIG. 32D

3200

421

424

422

421

432

434

424

422

421

430

424

422

3300

451

821

451

300

350

740

750

744

745

35

745

85

11

14

87

823

822

3300

314

821

314

745

745

760

760

745

745

823

822

4600
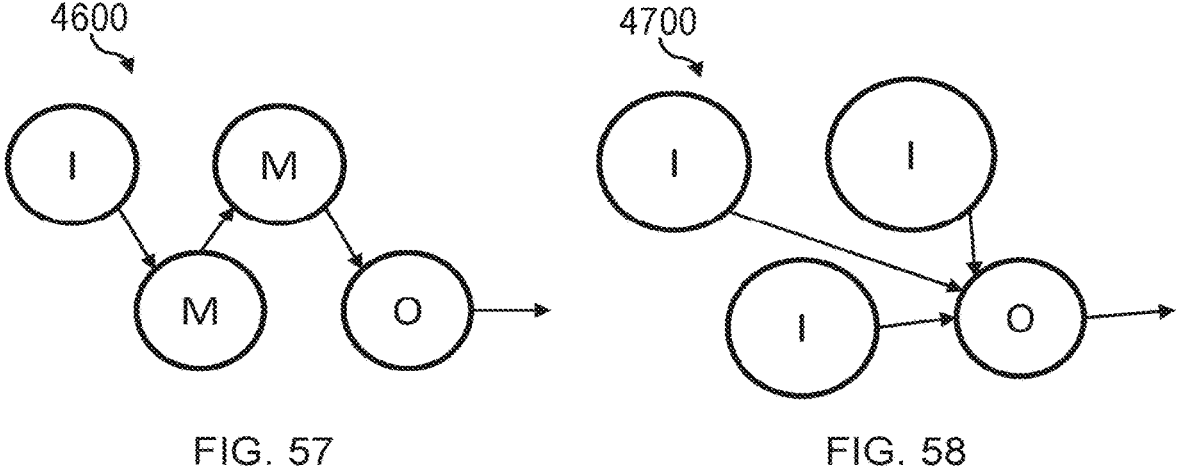
FIG. 57
4700
FIG. 58
4800
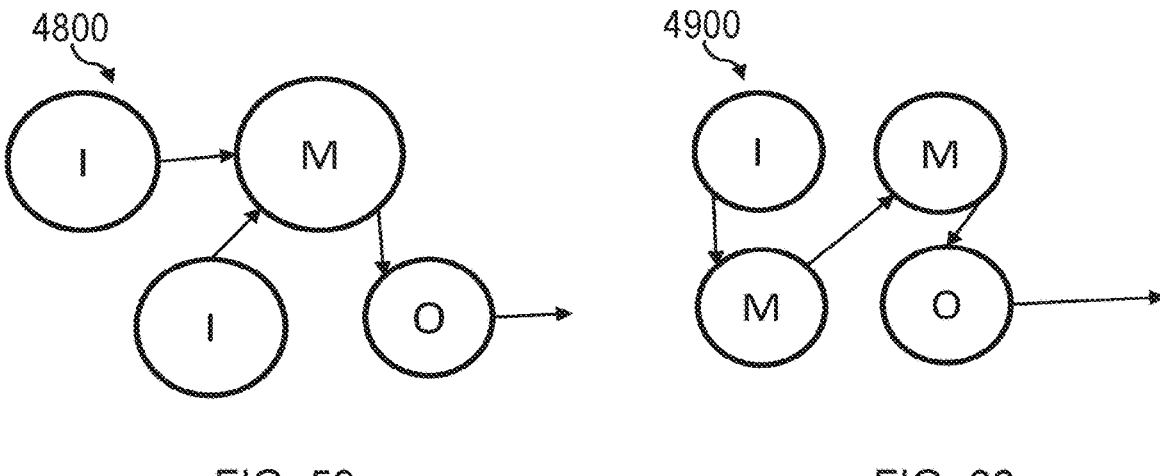
FIG. 59
4900
FIG. 60

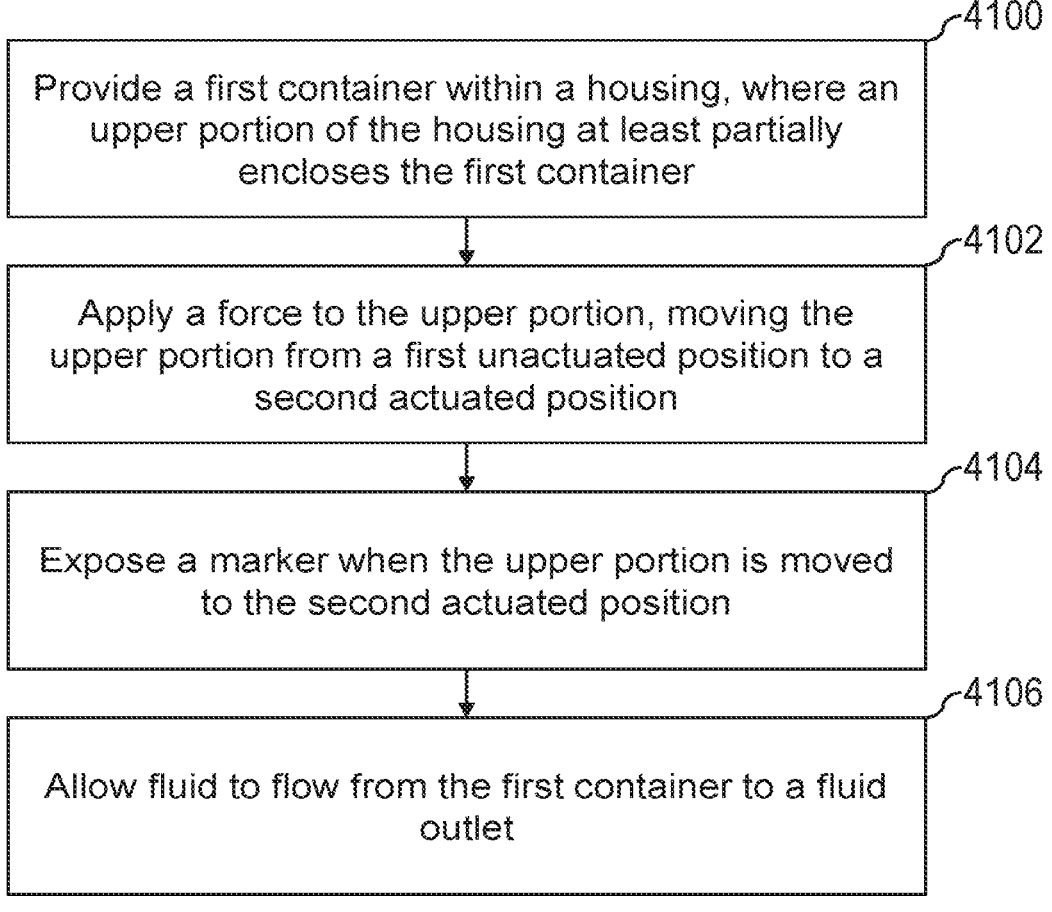

4100

Provide a first container within a housing, where an upper portion of the housing at least partially encloses the first container

4102

Apply a force to the upper portion, moving the upper portion from a first unactuated position to a second actuated position

4104

Expose a marker when the upper portion is moved to the second actuated position

4106

Allow fluid to flow from the first container to a fluid outlet

MEDICINAL FLUID DELIVERY DEVICE

RELATED APPLICATIONS

This application is a continuation of U.S. application Ser. No. 17/908,735, filed Sep. 1, 2022, which is a national stage filing under 35 U.S.C. § 371 of International Patent Application Serial No. PCT/US2021/020997, filed Mar. 5, 2021, which claims the benefit under 35 U.S.C. § 119(e) of U.S. Provisional Application Ser. No. 62/985,797, filed Mar. 5, 2020,. The contents of these applications are incorporated herein by reference in their entirety.

FIELD

Disclosed embodiments are related to medicinal fluid delivery devices, such as reconstitution devices, and related methods of use.

BACKGROUND

Medicinal fluids are administered to patients through a variety of methods. These conventional methods typically include injection by a syringe, ingestion, or delivery by an infusion pump and needle. Controlled volumes of medicinal fluids are prescribed and delivered through one or more of these methods.

In some cases, drugs products are manufactured in a dehydrated or otherwise unconstituted form, e.g. in a lyophilized form. That is, a drug may be stored and packaged as a dry material, which is combined and mixed with water or another reconstituting fluid prior to administration to a patient. In such cases, a predetermined amount of drug and, often, sterile water for injection are provided for a patient or other health care provider to combine shortly before administration.

SUMMARY

In some embodiments, systems and methods for administering medicinal fluids to a patient are provided. In particular, a reconstitution system allowing for simplified reconstitution of dry (e.g. powdered) drug products is provided. In some embodiments, the system allows for simplified access of liquid medicament. In some embodiments, a reconstitution device includes a first fluid path including a first open end disposed in a first spike, and an opposite end including an air inlet. In some embodiments, the device also includes a second fluid path having a second open end disposed in the first spike and a third open end disposed in a second spike. In some embodiments, a valve is disposed in the second fluid path between the second open end and third open end. In some embodiments, a third fluid path includes a fourth open end disposed in the second spike and an opposite end including a fluid outlet. Accordingly, in some embodiments, the device includes two interconnected dual-lumen spikes, which allow fluid transmission from a first container (e.g., containing sterile water) to a second container (e.g., containing a drug for reconstitution). In some embodiments, the fluid outlet may include a luer lock valve, such that a syringe may be fluidly connected to the fluid outlet and a reconstituted medicinal fluid may be withdrawn from the device. In some embodiments, a container including a powdered drug may be configured to contain a low or zero pressure vacuum, such that sterile water or another fluid from another container may be forced into the drug containing container without manually applied pressure or pumping. In some embodiments, a pressure differential between a drug containing container and a fluid containing container may be great enough that the fluid from the fluid containing container is expelled into the drug containing container, thereby agitating the drug to facilitate reconstitution.

In some embodiments, a reconstitution device may include a housing with an upper portion and a lower portion, where the lower portion is slidably received in the upper portion. In some embodiments, the upper portion may be configured to hold at least two containers, and the lower portion may include at least one spike for each of the at least two containers. In some embodiments, the upper portion may be configured to at least partially enclose the at least two containers and selectively retain them away from the spikes in the lower portion. In some embodiments, the upper portion may also be configured to apply force to the at least two containers as the upper portion slides from a first, unactuated position to a second, actuated position. In some embodiments, when the upper portion moves to the actuated position, the at least two containers may be pierced by spike(s) associated with that container. In some embodiments, the containers may be in fluid communication upon being pierced such that fluid from one container may flow to the other container. In some embodiments, a first container may be under vacuum, such that fluid from a second container is urged into the first container as the result of a pressure differential between the two containers.

In some embodiments, a reconstitution device includes a first fluid path having a first open end and an inlet, a second fluid path having a second open end and a third open end, the first open end and the second open end defining a first container receiving end, a valve positioned along the second fluid path between the second open end and the third open end, and a third fluid path having a fourth open end and an outlet, the third open end and the fourth open end defining a second container receiving end. The first container receiving end and second container receiving end face in a same direction.

In some embodiments, a reconstitution device includes a housing having a lower portion and an upper portion in slidable engagement with the lower portion, the upper portion being movable relative to the lower portion between an unactuated position and an actuated position, and a transfer engine disposed within the lower portion of the housing with a first container receiving end and a second container receiving end facing towards the upper portion of the housing. The reconstitution device also includes a fluid outlet in fluid communication with the second container receiving end of the transfer engine. The upper portion engages a first container and a second container such that the first container and second container move towards the first container receiving end and the second container receiving end, respectively, when the upper portion moves from the unactuated position to the actuated position. Physical access to the fluid outlet is at least partially obstructed when the upper portion is in the unactuated position, and physical access to the fluid outlet is permitted when the upper portion is in the actuated position.

In some embodiments, a reconstitution device includes a housing having a lower portion and an upper portion in slidable engagement with the lower portion, the upper portion being movable relative to the lower portion between an unactuated position and an actuated position. The reconstitution device also includes a transfer engine disposed within the lower portion of the housing with a first container receiving end and a second container receiving end facing towards the upper portion of the housing, where the transfer engine and lower portion are distinct components. The reconstitution device also includes a fluid outlet in fluid communication with the second container receiving end of the transfer engine.

In some embodiments, a reconstitution device includes a housing having a first portion and a second portion in movable engagement with the first portion, the first and second portions being moveable relative to one another between an unactuated configuration and an actuated configuration, a first spike coupled to the second portion of the housing, and a first ring coupled to the first portion of the housing and configured to at least partially surround a shoulder of a first container to retain the first container relative to the first spike.

In some embodiments, a medicinal fluid delivery device includes a housing having a lower portion and an upper portion in movable engagement with the lower portion, the upper portion being movable relative to the lower portion between an unactuated position and an actuated position, a fluid outlet configured to deliver fluid from a container disposed within the housing when the upper portion is in the actuated position, and a marker that is at least partially obstructed in the unactuated position of the upper portion, and where the marker is accessible in the actuated position of the upper portion.

In some embodiments, a medicinal fluid delivery device includes a housing having a lower portion and an upper portion in movable engagement with the lower portion, the upper portion being movable relative to the lower portion between an unactuated position and an actuated position, a fluid outlet configured to deliver fluid from a container disposed in the housing when the upper portion is in the actuated position, a communication module configured to send messages via at least one communication protocol, and a trigger configured to activate the communication module when the upper portion is moved from the unactuated position to the actuated position.

In some embodiments, a medicinal fluid delivery device includes an inlet adapter having an inlet container containing a medicinal fluid, an inlet spike configured to pierce the inlet container, where the inlet spike is configured to receive the medicinal fluid from the inlet container, an air inlet, an inlet adapter fluid channel fluidly connected to the inlet spike, and an inlet adapter coupling. The medicinal fluid delivery device also includes an intermediate adapter having an intermediate container containing a medicinal fluid or medicinal solid, an intermediate spike configured to pierce the intermediate container, a first intermediate fluid channel fluidly connected to the intermediate spike and configured to fluidly connect to the inlet adapter fluid channel, a second intermediate fluid channel fluidly connected to the intermediate spike, a first intermediate adapter coupling configured to connect to the inlet adapter coupling to releasably attach the intermediate adapter to the inlet adapter, and a second intermediate adapter coupling. The medicinal fluid delivery device also includes an outlet adapter having an outlet container containing a medicinal solid, an outlet spike configured to pierce the outlet container, an outlet adapter fluid channel fluidly connected to the outlet spike and configured to fluidly connect to the second intermediate fluid channel, an outlet fluidly connected to the outlet spike, and an outlet adapter coupling configured to connect to the second intermediate adapter coupling to releasably attach the outlet adapter to the intermediate adapter.

In some embodiments, a medicinal fluid delivery device includes an inlet adapter having an inlet spike configured to pierce an inlet container, an air inlet, an inlet adapter fluid channel fluidly connected to the inlet spike, and an inlet adapter coupling spaced from the inlet adapter fluid channel. The medicinal fluid delivery device also includes an intermediate adapter having an intermediate spike configured to pierce an intermediate container, a first intermediate fluid channel fluidly connected to the intermediate spike and configured to fluidly connect to the inlet adapter fluid channel, a second intermediate fluid channel fluidly connected to the intermediate spike, a first intermediate adapter coupling configured to be received in the inlet adapter coupling to releasably interlock the intermediate adapter with the inlet adapter, and a second intermediate adapter coupling, where the first intermediate adapter coupling and second intermediate coupling are spaced from the first intermediate fluid channel and the second intermediate fluid channel. The medicinal fluid delivery device also includes an outlet adapter having an outlet spike configured to pierce an outlet container, an outlet adapter fluid channel fluidly connected to the outlet spike and configured to fluidly connect to the second intermediate fluid channel, an outlet fluidly connected to the outlet spike, and an outlet adapter coupling configured to be received in the second intermediate adapter coupling to releasably interlock the outlet adapter with the intermediate adapter, where the outlet adapter coupling is spaced from the outlet adapter fluid channel.

In some embodiments, a medicinal fluid delivery device includes a housing having a lower portion and an upper portion in movable engagement with the lower portion, the upper portion being movable relative to the lower portion between an unactuated position and an actuated position. The medicinal fluid delivery device may include a transfer engine disposed within the lower portion of the housing with a first container receiving end facing towards the upper portion of the housing, and a fluid outlet in fluid communication with the transfer engine. The upper portion may be configured to engage a first container such that the first container moves towards the first container receiving end when the upper portion moves from the unactuated position to the actuated position. Physical access to the fluid outlet may be at least partially obstructed when the upper portion is in the unactuated position. Physical access to the fluid outlet may be permitted when the upper portion is in the actuated position.

In some embodiments, a medicinal fluid delivery device includes an inlet adapter having: an inlet spike configured to pierce an inlet container, an air inlet, and an inlet adapter fluid channel fluidly connected to the inlet spike. The medicinal fluid delivery device may also include an intermediate adapter having: an intermediate spike configured to pierce an intermediate container, a first intermediate fluid channel fluidly connected to the intermediate spike and configured to fluidly connect to the inlet adapter fluid channel, and a second intermediate fluid channel fluidly connected to the intermediate spike. The medicinal fluid delivery device may also include an outlet adapter having: an outlet spike configured to pierce an outlet container, an outlet adapter fluid channel fluidly connected to the outlet spike and configured to fluidly connect to the second intermediate fluid channel, and an outlet fluidly connected to the outlet spike. The medicinal fluid delivery device may also include an adapter plate. The inlet adapter, the intermediate adapter, and the outlet adapter may be configured to couple to the adapter plate.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIG. 15 is a flow chart of one embodiment of a reconstitution and medicinal fluid delivery process;

FIG. 32A is a schematic of another embodiment of a reconstitution device in a first state;

FIG. 32B is a schematic of the reconstitution device of FIG. 32A in a second state:

FIG. 32C is a schematic of the reconstitution device of FIG. 32A in a third state;

FIG. 32D is a schematic of the reconstitution device of FIG. 32A in a fourth state;

FIG. 57 is a plan schematic of another embodiment of a transfer engine;

FIG. 58 is a plan schematic of another embodiment of a transfer engine;

FIG. 59 is a plan schematic of another embodiment of a transfer engine;

FIG. 60 is a plan schematic of another embodiment of a transfer engine;

FIG. 63 is a flow chart of another embodiment of a medicinal fluid delivery process;

DETAILED DESCRIPTION

Figure 1:
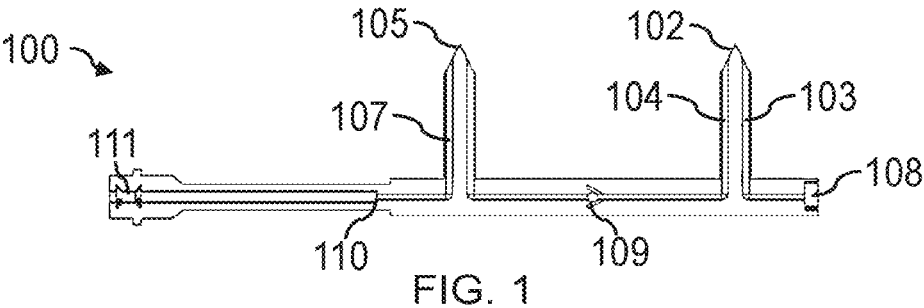
FIG. 1 is a schematic view of one embodiment of a transfer engine for a reconstitution device.

During a typical reconstitution and administration process, syringes may be used to mix a liquid diluent (e.g., sterile water for injection) with a liquid, dry, or otherwise unconstituted medicament, e.g. a medicament in lyophilized form. At each step, a nurse or other medical professional takes care to avoid contamination as reconstituting fluid is withdrawn from packaging and expelled into a mixing container or container of medicament. Such a process typically includes handling multiple containers and syringes.

Accordingly, conventional reconstitution methods performed by nurses and other medical professionals can be time consuming and complicated.

In some cases, patient-performed reconstitution and administration may be a preferable option for convenience and cost. Difficult procedures which are already time consuming when performed by medical professionals can be challenging for a patient practicing self-administration. Reducing the time consumption and complexity of medicinal fluid reconstitution and administration may be desirable for self-administering patients, as well as for health care providers.

In view of the above, the inventors have recognized the benefits of a reconstitution device which allows a patient or a health care provider to reconstitute and administer medicament contained in one container with a reconstituting fluid in another container. As compared to a conventional reconstitution and administration process, the reconstitution device may enable the use of a simpler reconstitution and administration process having less steps. The reconstitution device may also allow for reconstitution and administration to occur with reduced handling of containers. Furthermore, the reconstitution device may allow for less pressure to be applied to actuate the device than conventional devices, promoting an easier feel of actuation for a user. Additionally, the reconstitution device may improve agitation and mixing of a medicament and reconstituting fluid.

In some embodiments, a transfer engine may include multiple fluid paths in a compact arrangement that. e.g., facilitates transfer of fluid from a first container to a second container to reconstitute a drug located in the second container. In some embodiments, a reconstitution device includes a first fluid path including a first open end and an air inlet. The reconstitution device also includes a second fluid path having a second open end and a third open end. The first and second open ends may be parallel to one another and together define a first container receiving end. The reconstitution device also includes a valve positioned along the second fluid path between the second open end and the third open end. A third fluid path includes a fourth open end and a fluid outlet. The third open end and fourth open end may be parallel to one another and together define a second container receiving end. In some embodiments, a container receiving end may include a spike configured to spike into a container. According to this embodiment, the device includes two interconnected dual-lumen spikes, which allow fluid transmission from a first container (e.g., containing sterile water) to a second container (e.g., containing a drug for reconstitution). In some embodiments, the first open end of the first fluid path and the second open end of the second fluid path are disposed in a first spike. In some embodiments, the third open end of the second fluid path and the fourth open end of the third fluid path are disposed in a second spike. A portion of the first fluid path and a portion of the second fluid path may form the lumens of the first spike. A portion of the second fluid path and a portion of the third fluid path may form the lumens of the second spike. In some embodiments, a transfer engine may be used with fluid delivery devices other than reconstitution devices, e.g. devices for pooling or devices used to access a single container. As such, it should be appreciated that, in some embodiments, a transfer engine may include just a single container receiving end, rather than multiple container receiving ends.

In some embodiments, the fluid outlet may include a luer lock valve, such that a syringe or other delivery device may be fluidly connected to the fluid outlet, and a reconstituted medicinal fluid may be withdrawn from the transfer engine. However, in other embodiments other suitable fluid outlets may be employed with a reconstitution device, including, but not limited to, a luer activated device, simple luer or other threaded connector, slip-fit connector, and a pierceable septum. In some embodiments, a container including a powdered drug may be configured to contain a low or zero pressure vacuum, such that sterile water or another fluid from another container may be forced into the drug containing container without manually applied pressure or pumping. In some embodiments, a pressure differential between a drug containing container and a fluid containing container may be great enough that the fluid from the fluid containing container is expelled into the drug containing container at a speed that may help to agitate the drug to facilitate reconstitution.

The inventors have also recognized the benefits of a self-contained reconstitution device that allows a reconstitution process to be performed with the application of force in a single direction. A first container may be predisposed in the reconstitution device containing a reconstituting fluid along with a second container containing a medicament. The reconstitution device may allow force to be applied to a housing to fluidly join the first container to the second container, allowing the fluid to flow from the first container to the second container and reconstitute the medicament.

In some embodiments, a reconstitution device may include a housing having a lower and an upper portion, where the lower portion is slidably received in the upper portion, or vice versa. The upper portion may be configured to hold at least two containers, and the lower portion may include at least one spike for each of the at least two containers. The upper portion may be configured to at least partially enclose the at least two containers and selectively retain them away from the spikes disposed in the lower portion. The upper portion may also be configured to apply force to the at least two containers as the upper portion slides from a first, unactuated position to a second, actuated position where the upper portion is closer to the lower portion. In particular, a bottommost surface of the upper portion is closer to a base of the lower portion. When the upper portion is moved to the actuated position, the at least two containers may be pierced by the spike(s) associated with that container. Upon being pierced, the containers may be in fluid communication such that fluid from one container may flow to the other. In some embodiments, a first container may be under vacuum, such that fluid from a second container is urged into the first container as the result of a pressure differential between the two containers. The lower portion of the housing may be formed as a base that may be placed on a flat surface (e.g., table, countertop, etc.). The base may support the reconstitution device, and provide a platform against which force may be applied by a user. In some embodiments, a top surface of the upper portion of the housing may be curved, such that the reconstitution device may not be stable if a user attempts to use the upper portion as a base by resting the top surface of the upper portion on a flat surface. The instability may help to signal to a user that the device has been placed in an incorrect orientation for use. Such an arrangement also may promote a single orientation for use of the reconstitution device. Such an arrangement may also improve ergonomics relative to conventional reconstitution devices. The curved surface may offer a natural place to rest the hand, corresponding in shape to other objects and surfaces commonly received in the palm of the user. In this regard, the curved upper surface may yield positive transference, thereby promoting preferred handling and operation of the reconstitution device.

The inventors have also recognized the benefits of providing feedback to a user for the complete activation of a reconstitution device. Furthermore, the inventors have recognized the benefits of one or more retention features that retain a reconstitution device in an actuated condition to discourage repeated activation or retrieval of used containers form the reconstitution device. Additionally, such an arrangement may mitigate migration of an upper portion of a housing away from a lower portion of the housing as a result of elasticity of a pierced septum of a container biasing the upper portion away from the lower portion.

In some embodiments, a reconstitution device may include a housing having a lower portion and an upper portion, where the lower portion is slidably received in the upper portion, or vice versa. The upper portion may be configured to hold at least two containers, and the lower portion may include at least one spike for each of the at least two containers. The upper portion may be configured to at least partially enclose the at least two containers and selectively retain them away from the spikes disposed in the lower portion. The upper portion may also be configured to apply force to the at least two containers as the upper portion slides from a first, unactuated position to a second, actuated position where the upper portion is closer to the lower portion. The upper portion of the housing may have at least one upper stop and the lower portion may have at least one lower stop. The at least one upper stop may be configured to engage the at least one lower stop when the upper housing is moved to an actuated position to pierce each of the at least two containers. In some embodiments, the upper and lower stops may be corresponding shelves or ledges of the housing that abut one another to prevent further movement of the upper portion of the housing toward the lower portion of the housing. In some embodiments, the containers may function as an upper stop, abutting the lower portion of the housing (e.g., bottoming out) when the upper housing is moved to the actuated position. Upper and lower stops may be disposed on any suitable portion of an upper and lower housing that may be brought into contact with one another, as the present disclosure is not so limited. In some embodiments, an upper portion and lower portion of a housing may include one or more retention features to enable one-directional capture of the reconstitution device in an actuated position. The retention features may include flexible tabs, ratchet and pawl, hook and loop fasteners, adhesive, or another suitable arrangement for fastening two portions of a reconstitution device housing together when actuated. For example, in one embodiment, flexible tabs disposed on a lower portion of the housing may engage corresponding detents or recesses on an upper portion of the housing when the upper portion is moved to an actuated position.

The inventors have also recognized the benefits of obstructing physical user access to the fluid outlet before device actuation and permitting user access to the fluid outlet in response to actuation of a reconstitution device housing. In particular, the inventors have recognized the benefits of physically impeding access to a fluid outlet prior to the reconstitution of a medicament. The reconstitution device housing may be arranged to allow access to a fluid outlet only after two containers are fluidly joined such that fluid from a first container can flow to a second container containing a medicament for reconstitution. Such an arrangement may simplify a reconstitution and administration process, and may further ensure a medicament is reconstituted before a user attempts to couple a delivery device (e.g., a syringe, infusion pump, etc.) to the reconstitution device. This may help to prevent a user from prematurely withdrawing medicament before reconstitution is complete. Additionally, in cases where a vacuum is employed to transfer fluid between a first and second container, such an arrangement may ensure a vacuum inside of a container is maintained until pressure is equalized between the first and second container. In particular, such an arrangement may avoid air being drawn into a fluid path via the fluid outlet.

In some embodiments, a reconstitution device includes a housing having a lower and an upper portion, where the lower portion is slidably received in the upper portion. The upper portion may be configured to hold at least two containers, and the lower portion may include at least one spike for each of the at least two containers. The upper portion may be configured to at least partially enclose the at least two containers and selectively retain them at a distance from the spikes disposed in the lower portion prior to device actuation. The upper portion may also be configured to apply force to the at least two containers as the upper portion slides from a first, unactuated position to a second, actuated position where the upper portion is closer to the lower portion. In particular, a bottommost surface of the upper portion may be closer to a base of the lower portion. When the upper portion is moved to the actuated position, the at least two containers may be pierced by one or more associated spikes. Upon being pierced, the containers may be in fluid communication such that fluid from one container may flow from a first container to a second container and a medicament in the second container may be reconstituted by fluid from the first container. The spikes may be fluidly connected to a fluid outlet, which may be retained in the lower portion of the housing. The upper portion of the housing is configured to cover or otherwise obstruct physical user access to the fluid outlet when the upper portion is in the unactuated position. When the reconstitution device is actuated, physical access to the fluid outlet may be permitted. For example, in one embodiment, a cutout on the upper portion is configured to expose the fluid outlet when the upper portion is moved to the actuated position. In some embodiments, the fluid outlet may be connected to one or more spikes via flexible tubing, such that the fluid outlet is movable relative to the spikes. According to this embodiment, the fluid outlet may be accessed and removed from the lower housing via the cutout when the upper portion is in the actuated position. Once removed, a delivery device (e.g., syringe) may be coupled to the fluid outlet and used to withdraw the reconstituted medicament. In some embodiments, a fluid outlet may include a port cap configured to seal the fluid outlet and prevent air from entering a fluid path between the spikes and the fluid outlet until removed. According to this embodiment, the port cap may not be accessed and removed from the fluid outlet until the upper portion is in the actuated position.

While some embodiments described herein employ flexible tubing that allows a user to move a fluid outlet relative to a reconstitution device housing, other configurations where the fluid outlet is physically obstructed until activation of the reconstitution device may be employed. For example, in some embodiments, the fluid outlet may be rigidly attached to a reconstitution device housing. In some embodiments, the fluid outlet may be fixed relative to a lower portion of a housing. In some embodiments, a fluid outlet may be movably fixed to a reconstitution device housing. For example, in some embodiments, a fluid outlet may be coupled to a reconstitution device housing with a pin, such that the fluid outlet may rotate relative to the housing. In such an embodiment, activation of the reconstitution device may cause the fluid outlet to rotate from a first rotational position to a second rotational position. In another embodiment, the fluid outlet may be disposed on a ball that is disposed in a socket formed on a housing of the reconstitution device. In such an arrangement, the angle of the fluid outlet relative to the housing may be adjusted, but the fluid outlet may not be removable from the housing. Of course, a fluid outlet may have any suitable arrangement and may be associated with any suitable portion of a reconstitution device housing, as the present disclosure is not so limited. For example, a fluid outlet may be disposed on a lower, middle, or upper portion of a reconstitution device housing (e.g., a top third, middle third, or bottom third). A fluid outlet may be flexibly connected to the reconstitution device housing, may be movable about a hinge or pivot, or may be fixed relative to the housing.

In some embodiments, a reconstitution device may include a fluid outlet releasably attached to a reconstitution device outlet. The fluid outlet may also be coupled to flexible tubing that is disposed inside the reconstitution device housing when the fluid outlet is releasably attached to the housing. The fluid outlet may be rigidly retained in the lower, middle, or upper third of the reconstitution device housing, and may be physically accessible to user only after the reconstitution device housing is actuated. Once the fluid outlet is physically accessible, a delivery device may be coupled to the fluid outlet. For example, the delivery device (e.g., a syringe), may be coupled to the fluid outlet with a twisting motion. Of course, any suitable motion may be employed to couple the delivery device to the fluid outlet, as the present disclosure is not so limited. Once the delivery device is coupled, a user may pull or otherwise apply force to the fluid outlet with the delivery device to detach the fluid outlet from the reconstitution device housing. Once detached, the fluid outlet may be moved relative to the reconstitution device housing, thereby extending the flexible tubing.

The inventors have recognized benefits of promoting directional flow to ensure proper dosage and reconstitution. In particular, the inventors have recognized the benefits of a check valve or other one-way valve in promoting unidirectional flow from a first container to a second container. In some embodiments, the check valve or other one-way valve may be disposed in a fluid path between a first container and a second container. During a reconstitution process, a reconstituting fluid may flow from the first container to the second container and may be retained in the second container by the check valve. Such an arrangement may help to prevent backflow and loss of fluid or reconstituted medicament from the second container.

In some embodiments, a transfer engine for a reconstitution device includes a first fluid path extending between an inlet and first spike, a second fluid path extending between the first spike and a second spike, and a third fluid path extending between the second spike and a fluid outlet. In some embodiments, a check valve is positioned along the second fluid path. The check valve is configured to allow flow in a direction from the first spike to the second spike, but prevent flow in the opposite direction. Accordingly, if a first container containing a reconstituting fluid is pierced by and fluidly connected with the first spike, the fluid may flow from the first container, through the second fluid path and into the second container. If a second container containing a medicament for reconstitution is pierced by and fluidly connected with the second spike, the fluid from the first container may flow into the second container, but may be unable to flow back to the first container due to the presence of the check valve. In some embodiments, the second container may contain at least a partial vacuum, while the interior pressure of the first container may be at atmospheric pressure or may be above atmosphere pressure, such that the fluid in the first container is urged to flow to the second container by the pressure differential between the first container and the second container. The pressure differential may be arranged such that all of the fluid from the first container flows past the check valve towards the second container so that it may mix with and reconstitute the medicament. The check valve inhibits backflow of reconstituted drug, ensuring the correct dosage of the reconstituted medicament is retained in the second container and is accessible to a delivery device (e.g., syringe) via the fluid outlet.

The inventors have also recognized the benefits of improving agitation and mixing during a reconstitution process without requiring a user to handle one or more containers. In particular, the inventors have recognized the benefits of a check valve disposed between a first container and a second container that retains fluid in the second container and inhibits backflow to the first container. As reconstituted or partially reconstituted medicament is withdrawn and deposited in to the second container with a delivery device (e.g., a syringe), the fluid may be agitated to facilitate mixing but will remain accessible to the delivery device in the second container. The delivery device may then be used to effectively agitate and mix the medicament to ensure the medicament is fully dissolved or rehydrated prior to administration.

In some embodiments, a reconstitution device includes a first container and a second container disposed within an upper portion of a housing, where an upper portion of the housing at least partially encloses the first and second container. In some embodiments, a method of performing a reconstitution process includes applying a force to the upper portion to move the upper portion from a first unactuated position to a second actuated position. A first container may be pierced with a first spike disposed in a lower portion of the housing and a second container may be pierced by a second spike disposed in the lower portion of the housing as the upper portion is moved to the second actuated position. Once pierced, fluid may flow from the first container to the second container to occupy a vacuum or low pressure volume in the second container. As the fluid flows from the first container to the second container, the fluid may flow through a check valve configured to prevent flow in the opposite direction (i.e., back towards the first container). The method also includes withdrawing at least a portion of the fluid from the second container with a syringe via a fluid outlet. Once at least a portion of the fluid is withdrawn, the syringe may be used to redeposit the fluid into the second container. The syringe may be used to withdraw from and redeposit fluid into the second container until a drug in the second container is sufficiently mixed and reconstituted. During the moving of the fluid back and forth into and out of the second container, the check valve may ensure no fluid or medicament travels back to the first container. Once reconstituted, the drug may be fully withdrawn by the syringe and then self-administered by the user or administered to a patient.

While some embodiments described herein are directed to a reconstitution device, it should be appreciated that the various features and methods described herein may be used with a medicinal fluid delivery device that is not necessarily used for reconstitution. For example, in some embodiments, a medicinal fluid delivery device may be used with only a single container (e.g. to access the contents of the single container for delivery to a patient). In another example, a medicinal fluid delivery device may be used to pool contents from a plurality of containers without reconstitution. In other embodiments, however, a medicinal fluid delivery device may both reconstitute and pool (e.g., access the contents of two or more containers containing a fluid and one or more containers containing a solid). Accordingly, the various features and methods described herein are also applicable to a medicinal fluid delivery device having any number of containers, as the present disclosure is not so limited.

The inventors have also recognized the benefits of a reconstitution device or medicinal fluid delivery device which provides cues to a user practicing self-administration via one or more alerts on the reconstitution device itself or through a complementary device. The reconstitution or medicinal fluid delivery device may provide a visual, audio, and/or haptic alert to a user at to the status of a reconstitution process, and such an arrangement may simplify a reconstitution or medicinal fluid delivery process for a user.

In some embodiments, a reconstitution or medicinal fluid delivery device may include a first container having a fluid (e.g., reconstituting fluid) and a second container having a medicament (e.g., a lyophilized medicament). The reconstitution or medicinal fluid delivery device may also include a power source (e.g., battery), processor, and at least one indicator (e.g., alert module). The at least one indicator may include a visual indicator (e.g., LED, display screen, etc.), auditory indicator (e.g., speaker), and/or haptic indicator (e.g., eccentric rotating mass actuator, linear resonant actuator, piezoelectric actuator, etc.). The at least one indicator may indicate one or more states of the reconstitution or medicinal fluid delivery device during a reconstitution or medicinal fluid delivery process. For example, in one embodiment, the at least one indicator may indicate when a reconstitution device is actuated and a reconstituting fluid is flowing and mixing with a medicament. In another example, the at least one indicator may indicate when a reconstituting fluid has had suitable time to mix with the medicament, thereby indicating when a medicinal fluid is suitable to withdraw from the reconstitution device with a delivery device (e.g., syringe). In yet another example, the reconstitution or medicinal fluid delivery device may include an orientation sensor (e.g., accelerometer, gyroscope, etc.) and the indicator may indicate when the reconstitution or medicinal fluid delivery device is in a predetermined orientation, or conversely, when the reconstitution or medicinal fluid delivery device is in an orientation different than the predetermined orientation. In some embodiments, the reconstitution or medicinal fluid delivery device may include a communication device (e.g., a radio transceiver transmitting and receiving radio signals using one or more of Bluetooth, Bluetooth Low-Energy, Wi-Fi, 802.15.4, ZigBee, GSM, HSPA, CDMA, and/or any other suitable protocol). The communication device may be employed to communicate and transmit one or more alerts to a remote device (e.g., smartphone, pager, personal computer, tablet, etc.). The remote device may then provide the alert to a user by a visual, auditory, and/or haptic indicator.

The inventors have also recognized the benefits of a medicinal fluid delivery device configured to communicate with one or more remote devices. The medicinal fluid delivery device may be configured to communicate information to the one or more remote devices. For example, in some embodiments, dosage, time, and/or one or more sensor values (e.g., temperature, orientation, etc.) may be communicated to the one or more remote devices, such that the one or more remote devices may track a treatment schedule, or otherwise record information regarding usage of the medicinal fluid delivery device. In some embodiments, the medicinal fluid delivery device may include a marker which is revealed or otherwise accessible (e.g., physically accessible, visually accessible, or radio accessible) once the medicinal fluid delivery device is actuated. In other embodiments, a communication module of the medicinal fluid delivery device may be activated by a trigger once the medicinal fluid delivery device is actuated.

In some embodiments, a medicinal fluid delivery device includes a housing having a lower portion and an upper portion in movable engagement with the lower portion. Similar to previously discussed embodiments, the upper portion may be movable relative to the lower portion between an unactuated position (e.g., an upper position) and an actuated position (e.g., a lower position). The medicinal fluid delivery device may also include a fluid outlet configured to deliver fluid from a container disposed within the housing when the upper portion is in the actuated position. In some embodiments, the fluid outlet may be inaccessible to a user when the upper portion is in the unactuated position. According to such an embodiment, moving the upper portion to the actuated position may permit physical access to and/or reveal the fluid outlet. The medicinal fluid delivery device may also include a marker configured to be readable by a remote device (e.g., a smartphone) when accessible. For example, the marker may be a QR code, barcode, radio-frequency identification (RFID) tag, near-field communication (NFC) tag, or another suitable marker. The marker may be unpowered, such that the medicinal fluid delivery device does not include an onboard power source. In some embodiments, the marker may be partially obstructed when the upper portion is in the unactuated position, and the marker may be accessible to a user when the upper portion is in the actuated position. For example, in some embodiments, the upper portion may enclose the marker in the unactuated position and may reveal the marker in the actuated position (e.g., via a cutout). The marker may be employed by a remote device to obtain information about the medicinal fluid delivery device, such as dosage, date of manufacture, etc.

In some embodiments, a medicinal fluid delivery device includes a housing having a lower portion and an upper portion in movable engagement with the lower portion. Similar to previously discussed embodiments, the upper portion is movable relative to the lower portion between an unactuated position (e.g., an upper position) and an actuated position (e.g., a lower position). The medicinal fluid delivery device may also include a fluid outlet configured to deliver fluid from a container disposed within the housing when the upper portion is in the actuated position. In some embodiments, the fluid outlet may be inaccessible to a user when the upper portion is in the unactuated position. According to such an embodiment, moving the upper portion to the actuated position may permit physical access to and/or reveal the fluid outlet. The medicinal delivery device may also include a communication module configured to send messages via at least one communication protocol (e.g., Bluetooth, Bluetooth Low-Energy, Wi-Fi, 802.15.4, ZigBee, GSM, HSPA, CDMA, and/or any other suitable protocol). The communication module may be configured to send messages to a remote device (e.g., a smartphone) including information about the medicinal fluid delivery device (e.g., dosage, drug identity, time, and/or one or more sensor values such as temperature, orientation, etc.). The medicinal fluid delivery device may also include a trigger configured to activate the communication module when the upper portion is moved to the actuated position. Such an arrangement may ensure the communication module draws little to no power before actuation, such that a power source of the medicinal fluid delivery device has enough power for the communication module for a desired shelf life. In some embodiments, the trigger may be a switch, hall effect sensor, strain gauge, or other suitable sensor configured to detect the upper portion moving to the actuated position.

The inventors have also recognized the benefits of a reconstitution device that provides a user with mechanical advantage and/or electromechanical assist to reduce the force used to actuate the reconstitution device relative to conventional reconstitution devices. Such an arrangement may allow for easier and more consistent activation of a reconstitution device by a user.

In some embodiments, an upper portion of a housing and a lower portion of a housing may be operatively coupled via a screw mechanism where rotational force applied to the screw mechanism applies linear force bringing the upper portion closer to the lower portion, where the screw mechanism provides mechanical advantage relative to direct application of linear force. As another example, in some embodiments a lever may be linked to a lower portion of a housing so that linear force applied to the lever magnifies the force applied to an upper portion of a housing to move the upper portion of the housing toward the lower portion. In yet another embodiment, an upper housing may include an incline plane squeeze mechanism, where squeezing at least one wedge including an incline plane in a direction parallel to a surface on which the reconstitution device is disposed may force an upper housing portion toward a lower housing portion (or, alternatively, two containers toward corresponding spikes). Of course, any suitable arrangement including mechanical advantage or not including mechanical advantage may be employed for a reconstitution device, as the present disclosure is not so limited. Some embodiments of reconstitution devices including mechanical advantage are discussed further with reference to FIGS. 19A-21B.

In some embodiments, a housing of a reconstitution device may include a mechanical or electromechanical actuator that reduces the force of activation for the reconstitution device. For example, a reconstitution device may include one or more of a spring (e.g., compression, tension, torsion, air), servo, motor, and linear actuator. According to some embodiments, a reconstitution device may include a power source (e.g., battery), which may supply power to an electromechanical actuator. The actuator may be actuated by a user to correspondingly actuate the reconstitution device. Various user input devices may be employed for such an activation, including, but not limited to, a button or switch. In embodiments where a mechanical assist element is employed (e.g., a spring), a user may operate a release to actuate the reconstitution device. That is, the spring or other mechanical assist element may be pre-biased (i.e., have stored potential energy), which may be used to actuate a device when released. Of course, any mechanical or electromechanical assist configuration, or a combination thereof, may be employed in a reconstitution device, as the present disclosure is not so limited.

The inventors have also recognized the benefits of a modular medicinal fluid delivery device that may be employed to deliver a wide range of medicinal fluids in different volumes. In particular, the inventors have recognized the benefits of a modular transfer engine which may include multiple adapters that may be interchanged or expanded as appropriate for a given fluidly delivery application. An adapter may include at least one fluid channel configured to connect to at least one second fluid channel of another adapter. Additionally, the adapter may include a coupling separate and spaced from the at least one fluid channel which may be employed to physically interlock the adapter with another adapter. In this manner, the transfer engine may include any number of adapters in any desired configuration to deliver a medicinal fluid. The modular transfer engine may be employed for reconstituting lyophilized solids, or for pooling multiple medicinal fluids, or for accessing a single container.

In some embodiments, a medicinal fluid delivery device may be modular. The modular medicinal fluid delivery device may include an inlet adapter, an intermediate adapter, and an outlet adapter. The medicinal fluid delivery device may be arranged such that any number of intermediate adapters may be employed in a modular fashion to suit a particular delivery volume. In some embodiments, the inlet adapter, intermediate adapter, and outlet adapter may all be configured to fluidly connect to a container. For example, the inlet adapter, intermediate adapter, and outlet adapter may all include a spike configured to pierce a container to fluidly connect the container to the respective adapter. The inlet adapter may include an inlet adapter fluid channel and an inlet adapter coupling. The intermediate adapter may include a first intermediate fluid channel, a second intermediate fluid channel, a first intermediate adapter coupling, and a second intermediate adapter coupling. The outlet adapter may include an outlet adapter fluid channel and an outlet adapter coupling. The first intermediate adapter coupling is configured to connect with the inlet adapter coupling and the second intermediate adapter coupling is configured to connect with the outlet adapter coupling. Likewise, the inlet adapter fluid channel is configured to fluidly connect to the first intermediate fluid channel, and the outlet adapter fluid channel is configured to fluidly connect to the second intermediate fluid channel. The fluid channels may be separate from and spaced apart from the couplings, such that the adapters may be physically connected together (e.g., via the couplings) separately from the fluid connections (e.g., via the fluid channels). In cases where additional intermediate adapters are desired, the additional intermediate adapters may be identical to the first intermediate adapter and may be configured to fluidly and physically attach to the first intermediate adapter and inlet adapter, or the first intermediate adapter and outlet adapter. In some embodiments, additional intermediate adapters may not be identical to a first intermediate adapter but may nonetheless be configured to fluidly and physically attach to the first intermediate adapter and inlet adapter, or the first intermediate adapter and outlet adapter. Of course, any suitable number of intermediate adapters may be employed, as the present disclosure is not so limited. Additionally, it should be noted that the modular medicinal fluidly delivery device may be employed for reconstituting a solid medicament stored in one or more containers, for pooling liquid medicament from one or more containers, or any combination of reconstitution and pooling, or for accessing the contents of just a single container.

For purposes of this disclosure, the term "couple" (in all of its forms, couples, coupling, coupled, etc.) generally means the joining of two components directly or indirectly to one another. Such joining may be stationary in nature or movable in nature; may be achieved with the two components and any additional intermediate members being integrally formed as a single unitary body with one another or with the two components; and may be permanent in nature or may be removable or releasable in nature, unless otherwise stated.

Although particular embodiments of the present device will be described further herein, other alternate embodiments of all components related to the present reconstitution device are interchangeable to suit different applications. Turning to the figures, specific non-limiting embodiments of reconstitution devices and corresponding methods are described in further detail. It should be understood that the various systems, components, features, and methods described relative to these embodiments may be used either individually and/or in any desired combination as the disclosure is not limited to only the specific embodiments described herein.

FIG. 1 is a schematic view of one embodiment of a transfer engine 100 that may be used in a reconstitution device or other mixing device. As shown in FIG. 1, the transfer engine includes a first spike 102 and a second spike 105 which are each configured to pierce a rubber stopper, septum, or any other suitable seal of a container. The first spike 102 is associated with a first fluid path 103 and a second fluid path 104. In particular, a first open end of the first fluid path is disposed in the first spike, as is a second open end of the second fluid path. The portions of the first and second fluid paths disposed in the first spike are parallel to one another, and together they define a first container receiving end. According to the embodiment of FIG. 1, the first fluid path is associated with an inlet 108. In the depicted embodiment, the inlet is configured as an air inlet and includes a hydrophobic filter configured to allow air to pass into the first fluid path while any liquids are inhibited from crossing the hydrophobic filter. Of course, any suitable inlet or vent to allow air to enter the transfer engine may be employed, as the present disclosure is not so limited. In some embodiments, the air inlet may be configured as check valve configured to let air in to the first fluid path while preventing air or fluid from exiting the first fluid path. The second fluid path extends between the first spike and a second spike 105. A check valve 109 is positioned along the second fluid path 104. The check valve 109 is configured to allow fluid and air to flow through the second fluid path in a direction from the first spike toward the second spike, but not vice versa. A third fluid path 107 has a fourth open end also disposed in the second spike, and extends from the fourth open end to an outlet 111. The portions of the second fluid path and third fluid path that are disposed in the second spike are parallel to one another, and together they define a second container receiving end. The outlet of the depicted embodiment is configured as a luer activated valve. Of course, any suitable valve or fluid outlet connection may be employed with the transfer engine 100, as the present disclosure is not so limited. For example, in other embodiments another suitable fluid outlet may be employed with the transfer engine including, but not limited to, a luer activated device, simple luer or other threaded connector, slip-fit connector, and pierceable septum. According to the embodiment of FIG. 1, the transfer engine also includes a drug filter 110 disposed in the third fluid path configured to filter any drug precipitates or undissolved medicament from fluid flowing to the outlet.

According to the transfer engine of FIG. 1, the first container receiving end and second container receiving end are each configured to receive a first container and a second container, respectively. The first container may be configured to contain a reconstituting fluid (e.g., sterile water for injection), while the second container may contain a medicament (e.g., dry drug product) for reconstituting. When the first container is pierced by the first spike 102 and the second container is pierced by the second spike 105, the fluid from the first container may flow into the second container and mix with the medicament to form a medicinal fluid. The check valve 109 may retain the medicinal fluid in the second container and inhibit backwards flow of the fluid from the second container to the first container. Once the medicinal fluid is disposed in the second container, it may be withdrawn via the outlet 111 with a delivery device, such as a syringe. One embodiment of a reconstitution process is described further with reference to FIGS. 3-6.

Figure 2:
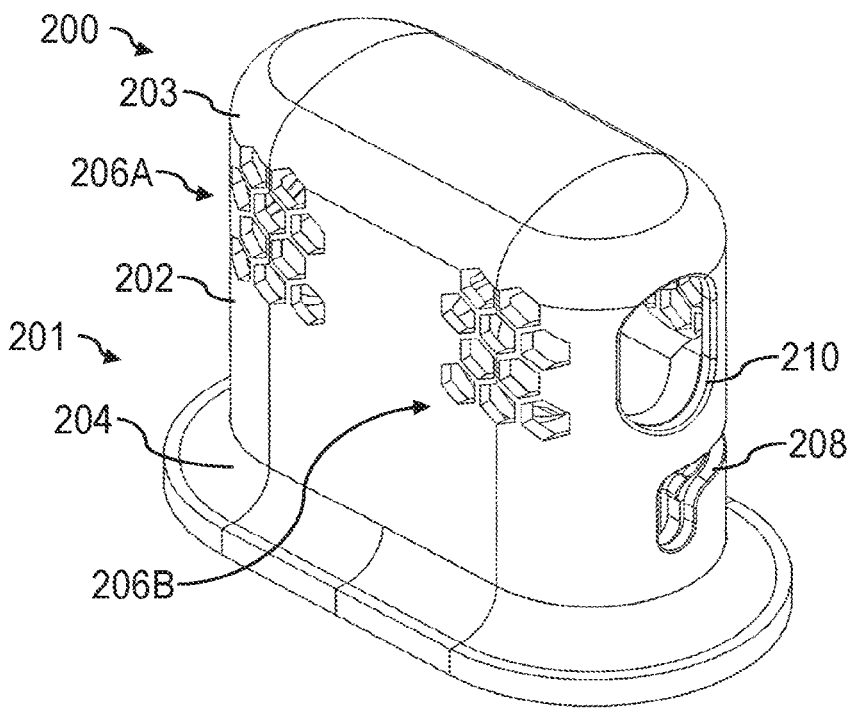
FIG. 2 is perspective view of one embodiment of a reconstitution device.

FIG. 2 is perspective view of one embodiment of a reconstitution device 200. The reconstitution device shown in FIG. 2 may include a transfer device (e.g., a transfer device similar to that of FIG. 1) configured to reconstitute a medicinal fluid using two containers. That is, the reconstitution device of FIG. 2 is configured to house two containers and reconstitute and deliver a drug. As shown in FIG. 2, the reconstitution device includes a housing 201 having an upper portion 202 and a lower portion 204. According to the embodiment shown in FIG. 2, the upper portion 202 is slidable relative to the lower portion 204 between an actuated position and an unactuated position. Examples of this sliding movement and associated features will be discussed further with reference to the embodiments of FIGS. 7-12. The lower portion 204 is formed as a flat base on which the reconstitution device may be supported in a stable orientation on a flat surface such as a table, desk, countertop, etc. In contrast, the upper portion 202 includes a rounded top surface 203, such that the reconstitution device is not supported in a stable orientation by the rounded top when placed on a flat surface. Accordingly, the housing 201 shown in FIG. 2 is configured to have a primary orientation where the housing is stable when placed on a flat surface. In this primary orientation, force may also be applied to the upper portion 202 while the lower portion 204 inhibits rotation of the housing. Additionally, the rounded top surface 203 is configured to provide a handle for a user to grasp, promoting correct use of the reconstitution device.

According to the embodiment of FIG. 2, the reconstitution device is configured to house two containers. As noted previously, the two containers may be joined by a transfer engine disposed in the reconstitution device, exemplary embodiments of which are described herein. Each of the containers may contain a specific dosage of a medicament and/or reconstitution fluid. Before reconstituting and administering a medicinal fluid, a patient may wish to check that the containers of the correct size and dosage are disposed in the reconstitution device, especially in cases where the containers are enclosed by the upper portion 202 of the housing 201 and are non-removable. Accordingly, in the embodiment of FIG. 2, the upper portion 202 includes windows 206A, 206B configured to allow a user to view inside of the upper portion. In particular, the windows 206A, 206B may be aligned with a label of a container disposed inside of the housing, allowing a user to obtain information about the medicament in the container, e.g., drug type, volume, dosage, etc. The windows 206A, 206B have a covering to inhibit a user from inserting fingers into the reconstitution device. According to the embodiment in FIG. 2, the upper portion also includes a window 210 which further improves visibility of the label. In some embodiments, the window 210 may allow a user to contact and rotate a container that is adjacent the window to better view the label of the container. Such windows may be disposed on opposing sides of the upper portion, allowing both containers disposed in the housing to be viewable and/or suitably rotated to view the label. In some embodiments, a window of a reconstitution device housing may include a magnification lens to allow a user to more easily read text on a container disposed within the reconstitution device housing. In some embodiments. LEDs or other suitable lighting elements may be disposed inside of the upper portion to illuminate any labels of the containers and/or provide one or more visual alerts to a user. Illumination of the containers may be beneficial for medicaments where patient visualization is desirable. In some embodiments, the lighting elements may emit a wavelength of light under which a medicament disposed in the containers is not susceptible to breaking down. Such an arrangement may be beneficial for some light-sensitive medicaments. In some embodiments, a reconstitution device may not have any windows and may be arranged to conceal containers inside of the housing. As an example, such an arrangement may be suitable for photosensitive medicaments susceptible to light degradation.

According to the embodiment of FIG. 2, the reconstitution device 200 is configured to obstruct access to a fluid outlet of a transfer engine disposed in the housing 201 prior to device actuation, and subsequently permit access to the fluid outlet after device actuation. That is, sliding of the upper portion 202 relative to the lower portion 204, selectively exposes or covers a fluid outlet, depending on the position of the upper portion relative to the lower portion. In some embodiments, the reconstitution device obstructs access to the fluid outlet by both concealing the fluid outlet from the user and physically obstructing access to the fluid outlet. In other embodiments, the fluid outlet is visible to the user prior to device actuation, but access to the fluid outlet is discouraged, e.g. by a physical obstruction.

Figure 9:
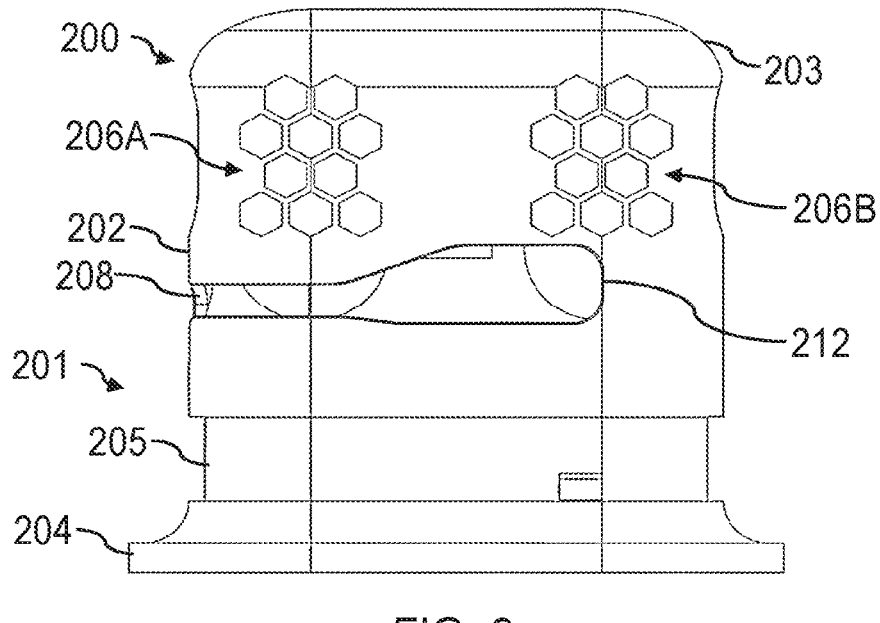
FIG. 9 is a side elevation view of the reconstitution device of FIG. 7.
Figure 10A:
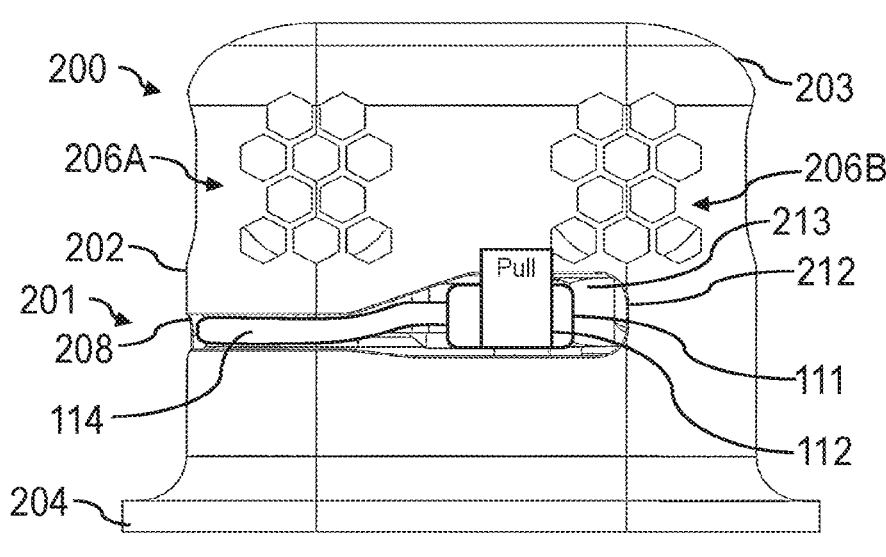
FIG. 10A is a side elevation view of the reconstitution device of FIG. 8.
Figure 10B:
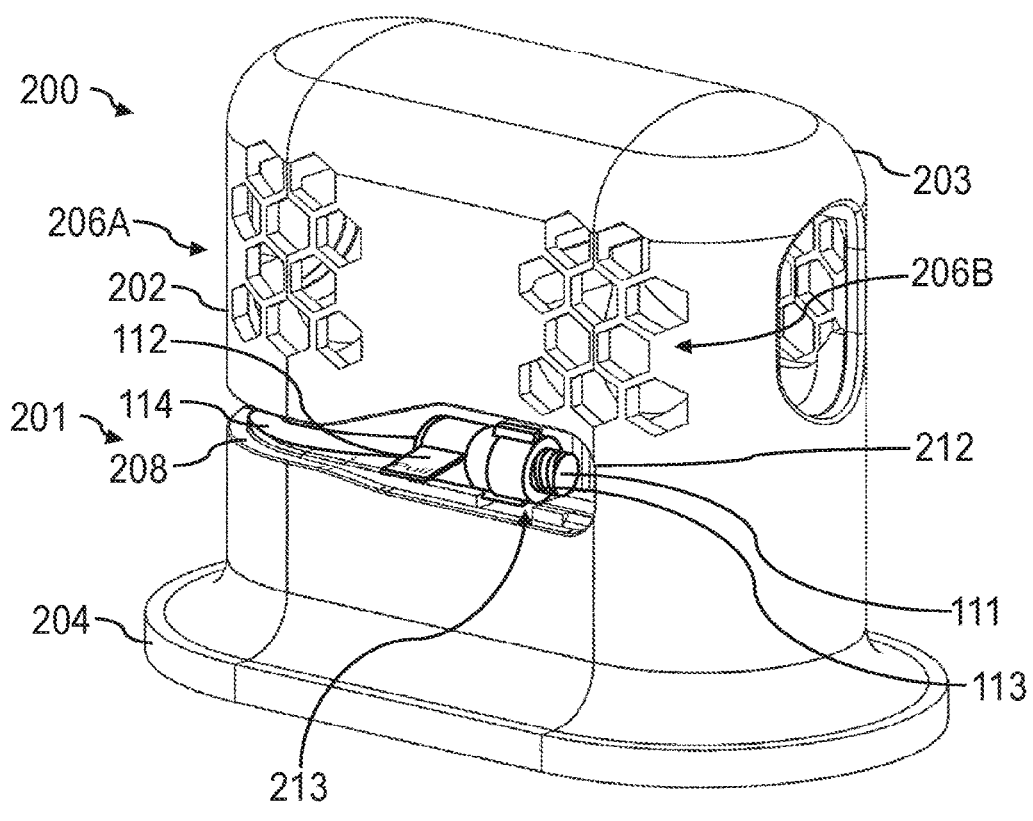
FIG. 10B is a perspective view of the reconstitution device of FIG. 10A.

In the embodiment of FIG. 2, and as shown in FIGS. 9-10B, the upper portion includes a slot 208 that forms a part of a larger cutout that exposes and allows a fluid outlet to be physically accessed and removed from the housing when the upper portion is in the actuated position as shown in FIGS. 10A-10B.

Figure 3:
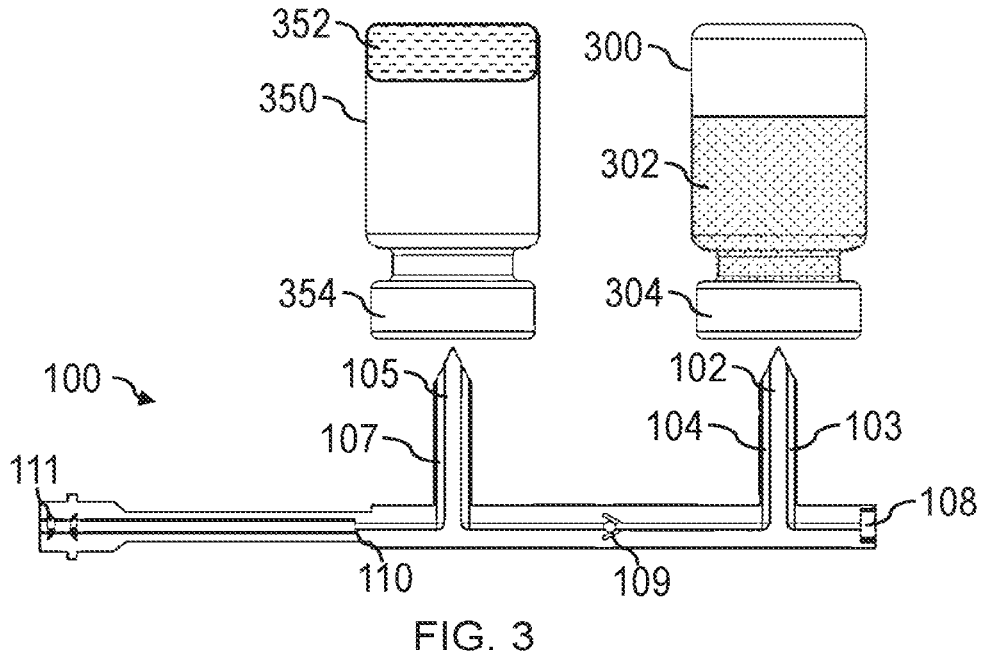
FIG. 3 is a schematic view of one embodiment of a transfer engine for a reconstitution device during a first stage of one embodiment of a reconstitution and medicinal fluid delivery process.

FIG. 3 is a schematic view of one embodiment of a transfer engine 100 for a reconstitution device during a first stage of one embodiment of a reconstitution and medicinal fluid delivery process. According to the embodiment of FIGS. 3-6, the transfer engine is similar to the embodiment described in FIG. 1. A first fluid path 103 extends between an inlet 108 and a first open end disposed in a first spike 102. A second fluid path 104 extends between a second open end disposed in the first spike 102 and a third open end disposed in a second spike 105. A third fluid path 107 extends between a fourth open end disposed in the second spike and an outlet 111. The first spike defines a first container receiving end while the second spike defines a second container receiving end. The inlet 108 is configured as an air vent and includes a hydrophobic filter allowing air to flow into the transfer engine but preventing fluid from flowing out of the transfer engine via the inlet. A check valve 109 may be included along the second fluid path 104. The check valve 109 is configured to allow fluid to flow in one direction through the second fluid path in a direction from the first spike toward the second spike. The outlet 111 is configured as a luer activated valve which may receive a delivery device (e.g., a syringe) that is able to withdraw a reconstituted medical fluid from the transfer engine. According to the embodiment of FIGS. 3-6, the transfer engine also includes a drug filter 110 disposed in the third fluid path configured to filter any drug precipitates or undissolved medicament from flowing to the outlet. The drug filter may be positioned anywhere in the fluid path between the outlet 111 and the fourth open end of the third fluid path 107.

As shown in the embodiments of FIGS. 3-6, two containers are employed with the transfer engine 100. In particular, a first container 300 is configured to be pierced by the first spike 102. The first container includes a reconstitution fluid 302 sealed by a stopper 304. The reconstitution fluid may be sterile water for injection or another suitable fluid. Stopper 304 is configured as a stopper with a septum that may be pierced by the first spike 102. The stopper may be made of rubber, silicone, or any other suitable material. Of course, any suitable stopper or seal may be employed, as the present disclosure is not so limited. A second container 350 is configured to be pierced by the second spike 105. The second container includes a medicament 352 disposed in a bottommost portion of the second container opposite a stopper 354. Such an arrangement may ensure the medicament does not block or otherwise inhibit flow of fluid through either the second fluid path 104 or third fluid path 107 via the third and fourth open ends, respectively. Of course, in other embodiments, the medicament may be disposed in another portion of the second container, and the present disclosure is not so limited. For example, the medicament may be disposed adjacent and abutting the stopper 354. In some embodiments, though the medicament may be abutting the second spike 105 when the stopper 354 is pierced, the flow of fluid therethrough may break up the medicament so that the fluid paths remain free. In some embodiments, a piercing tip of a spike may lift the medicament and keep the medicament spaced from the open ends of the fluid paths. Like the stopper of the first container, the stopper 354 of the second container is configured as a stopper with a septum that may be pierced by the second spike 105. The medicament may be a lyophilized drug product that may be in a powered form to facilitate dissolution into the reconstituting fluid. Of course, the medicament may take any suitable form, as the present disclosure is not so limited. As shown in the embodiments of FIGS. 3-6, the first and second containers are inverted to allow gravity to urge fluid disposed in the containers towards the outlet 111 or an otherwise lower height portion of the transfer engine. Put another way, in some embodiments, the first and second containers are arranged such that air inside of the containers is disposed in the containers at an end opposite the spikes. Such an arrangement may ensure fluid is drawn through the spikes before air in the containers. Additionally, according to the embodiment of FIGS. 3-6, 10 mL containers are shown. However, any suitably sized container may be employed, including, but not limited to containers having a volume greater than or equal to 0.1 mL, 0.3 mL, 0.5 mL, 1 mL, 1.25 mL, 2 mL, 2.5 mL, 5 mL, 10 mL, 20 mL, 30 mL, and 40 mL, 50 mL, 75 mL, 100 mL, 200 mL, and 300 mL.

As shown in the state of FIG. 3, the first container 300 is inverted and positioned above the first spike 102. Likewise, the second container 350 is inverted and positioned above the second spike 105. The stopper 304 of the first container and the stopper 354 of the second container are spaced from the first spike and second spike respectively, such that the first container and second container remain sealed and not in fluid communication with the transfer engine 100. Accordingly, the state shown in FIG. 3 may be the state of a reconstitution device just prior to initiating a reconstitution process. The first container and second container may be retained in a spaced relationship relative to the spikes 102, 105 so that the fluid 302 in the first container and medicament 352 in the second container remain sterile and ready for use during transportation, storage, and delivery to an end user or patient. In some embodiments, the transfer engine 100 may be disposed in a first housing portion while the first and second containers 300, 350 are disposed in a second housing portion. The second housing portion may be selectively movable relative to the first housing portion upon initiating a reconstitution process. When a reconstitution process has not been initiated, the second housing portion may ensure the first and second containers remain sealed until initiating that process. For example, in some embodiments, a pin or safety may be removed or otherwise activated by a user to enable the containers to be pierced by the spikes. In another example, a threshold force applied to the second housing portion may be required before the first and second containers are permitted to be pierced.

Figure 4:
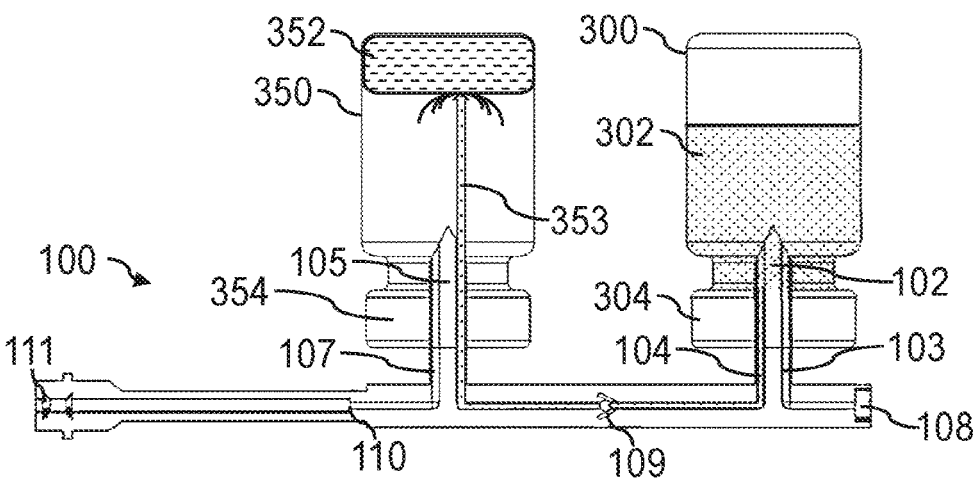
FIG. 4 is a schematic view of the transfer engine of FIG. 3 during a second stage of the reconstitution and medicinal fluid delivery process.

FIG. 4 is a schematic view of the transfer engine 100 of FIG. 3 during a second stage of the reconstitution and medicinal fluid delivery process. According to the stage of FIG. 4, the first container 300 and second container 350 have been pierced by the first spike 102 and second spike 105, respectively. According to the embodiment of FIG. 4, the second container 350 is under at least partial vacuum, such that the pressure inside of the second container 350 is lower than the pressure inside of the first container 300 and/or atmospheric pressure surrounding the transfer engine. Accordingly, as shown in FIG. 4, when the first container and second container are pierced simultaneously, the pressure differential between the first container 300 and second container 350 urges the reconstituting fluid 302 into the second container 350. Indeed, as shown in FIG. 4, the pressure differential may be so great that the fluid 302 is ejected out of the third open end of the second fluid path 104 and impacts the medicament 352 disposed on an end of the second container 350 opposite the second spike 105. As the fluid is urged into the second container 350, it mixes with the medicament and forms a medicinal fluid. The arrangement of the medicament on a bottommost portion spaced from the second spike 105 is configured to allow the jet of fluid 353 to impact and disperse the medicament to facilitate mixing of the medicament and reconstitution fluid. In some embodiments, the medicament 352 dissolves in the reconstituting fluid. In other embodiments, the medicament rehydrates the medicament.

In some embodiments, at least one spike of a reconstitution device may include open ends for internal lumens (i.e., fluid paths) that direct fluid flow into a container at an angle. For example, in some embodiments, the lumens inside the spike may terminate in open ends disposed in a side of the spike. That is, the open ends may be formed in a substantially vertical surface of the spikes, such that fluid flow through the spike is directed sideways relative to a piercing direction of the spike. In some embodiments, a spike may include multiple open ends for an internal lumen so that flow is directed out of multiple sides of the spike. In some embodiments, an open end may be angled relative to a piercing or insertion direction of the spike so that fluid flow is directed at that angle. In some embodiments, an open end of an internal lumen of a spike may be angled between 1 and 90 degrees relative to a piecing direction of the spike. Depending on the angle of the open end, and a particular spike arrangement, different types of fluid flow may be generated when fluid flows out of the spike into a container. For example, flow angled relative to a spike piercing direction may generate a vortex inside of a container. In some embodiments, a spike may include a flow nozzle which generates a gentle or otherwise slow misting spray. Without wishing to be bound by theory, different medicaments may be more readily reconstituted depending on the flow. Additionally, some medicaments may be damaged by particularly harsh or powerful flow. Accordingly, exemplary embodiments described herein may employ any suitable spike arrangement to generate a desirable fluid flow inside of a container.

As noted above, in some cases, different medicaments may be damaged or degraded by particular harsh or powerful flow. Additionally, some reconstituted medicaments may be susceptible to breaking down under high fluid shear. Accordingly, in some embodiments, one or more fluid paths of a transfer engine may include a flow restrictor or otherwise be configured to restrict a flow rate between a first container, a second container, and an outlet. For example, in some embodiments, a diameter of a fluid path between a first container and a second container may have a cross-sectional area smaller than that of fluid paths elsewhere in the transfer engine. In some embodiments, a fluid path between a second container and a fluid outlet may have a cross-sectional area smaller than that of fluid paths elsewhere in the transfer engine. In some embodiments, a fluid path may include a flow rate check valve that is configured to close if a fluid flow rate is too high. Such arrangements may ensure fluid flows at correct rates and medicament is not inadvertently damaged when withdrawn into a delivery device.

Of course, the reconstituting fluid and medicament may take any initial form to ultimately form medicinal fluid, as the present disclosure is not so limited. Additionally, the exemplary transfer engine and process shown in FIG. 4 may be used for mixing two fluids, as the present disclosure is not so limited. The two fluids may be the same fluid or different fluids.

According to the embodiment of FIG. 4, as the reconstitution fluid 302 flows into the second container 350, the fluid 302 is prevented from flowing back to the first container 300 by the check valve 109. The pressure differential between the first container 300 and second container 350 may be arranged such that substantially all of the reconstitution fluid flows past the check valve 109. As the fluid is displaced from the first container 300, air enters the inlet 108 to replace the flowing fluid. Accordingly, once pressure is equalized between the first container, second container, and atmosphere, the first container may contain air, while the second container contains both the reconstituting fluid and the medicament. Such an arrangement may be beneficial to help prevent portions of the reconstitution fluid from flowing back into the first container 300. In some cases, fluid that flows back to the first container 300 may be difficult to withdraw from the transfer engine. Additionally, the check valve may help to ensure the full dose of medicament remains in the second container 350 to be mixed and reconstituted and therefore a full dose or a proper concentration is able to be withdrawn via the outlet 111.

In some embodiments, once the pressure is equalized between the first container 300, second container 350, and atmospheric pressure, the medicament has not yet completely combined with the reconstituting fluid. Accordingly, in some embodiments, a user may swirl or shake the transfer engine 100 or a device including the transfer engine to ensure proper mixing of the reconstituting fluid 302 and medicament 352. In some embodiments as will be discussed further with reference to FIG. 6, a delivery device may be used to agitate and mix the reconstitution fluid and medicament.

Figure 5:
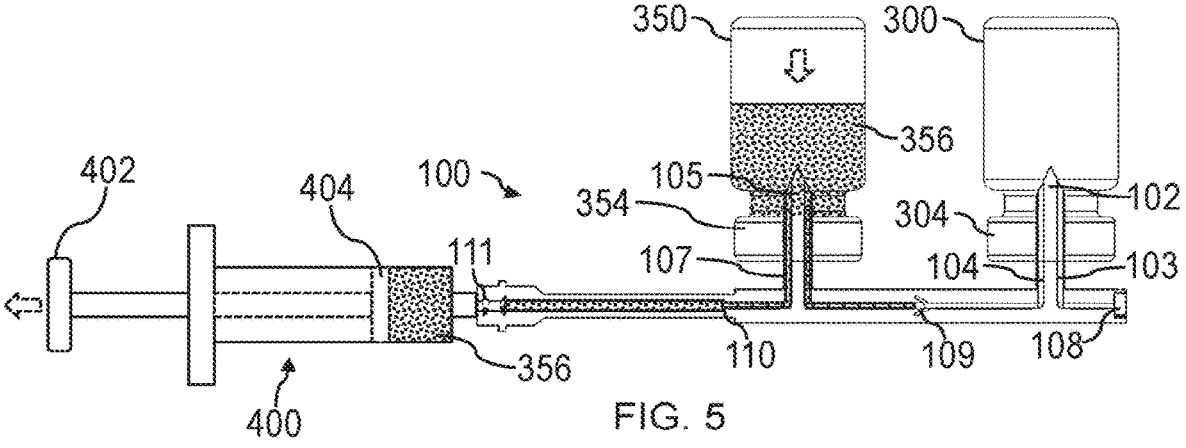
FIG. 5 is a schematic view of the transfer engine of FIG. 3 during a third stage of the reconstitution and medicinal fluid delivery process.

FIG. 5 is a schematic view of the transfer engine 100 of FIG. 3 during a third stage of the reconstitution and medicinal fluid delivery process. As shown in FIG. 5, a delivery device is connected to the outlet 111. The delivery device of FIG. 5 is a syringe 400 including a handle 402 connected to a plunger 404. The syringe may be connected to the outlet with a luer lock connector or any other suitable fluid and mechanical connection. According to the state of FIG. 5, the handle has been withdrawn in a direction away from the transfer engine 100 to fill the syringe with a medicinal fluid 356 formed by the reconstituted medicament shown in FIGS. 3-4. As shown in FIG. 5, the check valve 109 prevents the medicinal fluid from flowing back to the first container 300. The medicinal fluid is withdrawn from the second container 350 and is replaced by air via the inlet 108, as shown by the dashed arrow. According to the embodiment of FIG. 5, the filter 110 filters any drug precipitates or undissolved medicament from being transferred to the syringe. Accordingly, if the medicinal fluid 356 is fully reconstituted the fluid may be withdrawn into the syringe 400 and subsequently administered to a patient using a suitable administration process.

Figure 6:
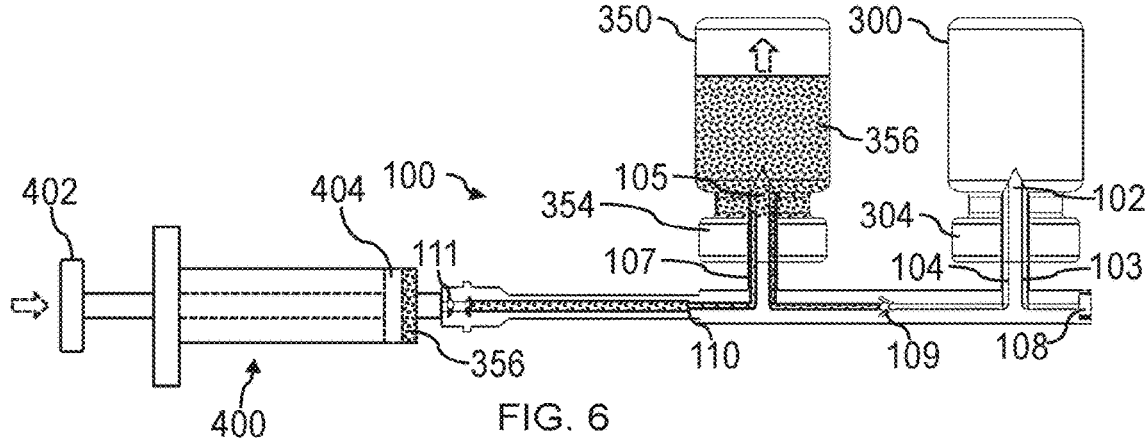
FIG. 6 is a schematic view of the transfer engine of FIG. 3 during an optional fourth stage of the reconstitution of medicinal fluid delivery process.

In some embodiments, a further mixing step may be administered to facilitate reconstitution or other mixing of the container contents. This mixing step may be optional in some embodiments. FIG. 6 is a schematic view of the transfer engine of FIG. 3 during a fourth stage of the reconstitution of medicinal fluid delivery process. In particular, in the state shown in FIG. 6, the syringe 400 is employed to facilitate mixing of the medicinal fluid 356, complementing or replacing other methods of mixing such as swirling and shaking of the transfer engine 100. From the state shown in FIG. 5, where the medicinal fluid is at least partially drawn into the syringe, the handle 402 of the syringe may be pushed towards the transfer engine 100 to correspondingly move the plunger 404 and drive the medicinal fluid back into the second container 350. Such action may facilitate combination of the medicament with the reconstituting fluid. As shown in FIG. 6, the medicinal fluid is inhibited from flowing back to the first container 300 by the check valve. Accordingly, the back flow of the medicinal fluid into the second container may compress the air in the second container and elevate the pressure of the medicinal fluid. A process of withdrawing and depositing a portion of the medicinal fluid from the second container may be repeated until the medicinal fluid is sufficiently combined for administration.

In some embodiments, the third fluid path 107 may include an air outlet that allows the second container 350 to depressurize. In one embodiment, the air outlet may be arranged as a one-way vent, such that air may escape the second container 350 via the third fluid path 107, but air may not enter the second container. According to this embodiment, the source of any air disposed in the second container 350 may originate from the air inlet 108 so that the reconstitution fluid may be drawn from the first container into the second container. However, when the syringe 400 is used to mix the medicinal fluid 356 by moving portion of the medicinal fluid back and forth from the second container 350, the air outlet may allow the pressure of the fluid to remain effectively constant, thereby reducing the force to deposit the fluid back into the second container. Of course, the air outlet may take any suitable form of valve or filter and may be disposed on any suitable part of the transfer engine 100 and/or second container 350. For example, the air outlet may be disposed on a second container side of the check valve 109 in the second fluid path 104. As another example, the air outlet may be disposed on the second container (e.g., the base of the second container) so that pressurized air above the medicinal fluid 356 can escape.

Figure 7:
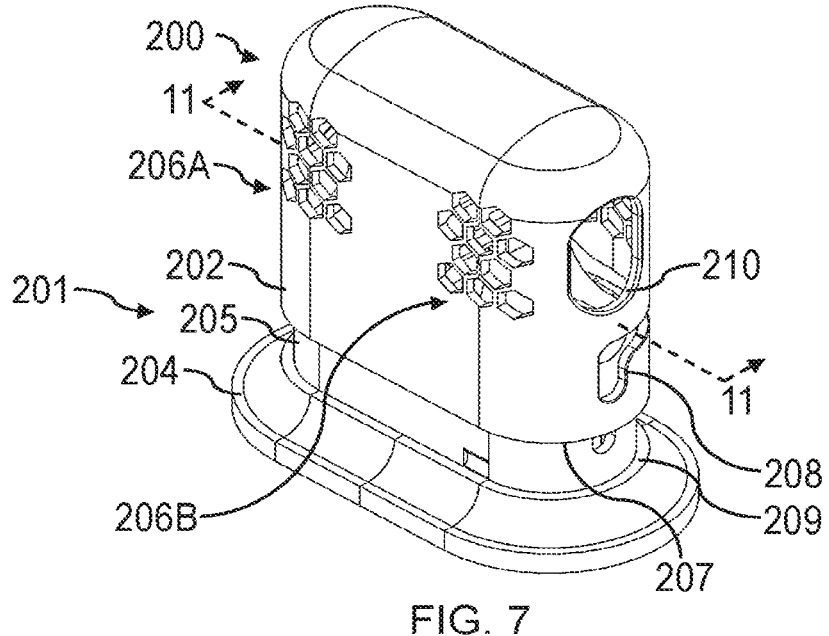
FIG. 7 is a perspective view of one embodiment of a reconstitution device in an unactuated state.
Figure 8:
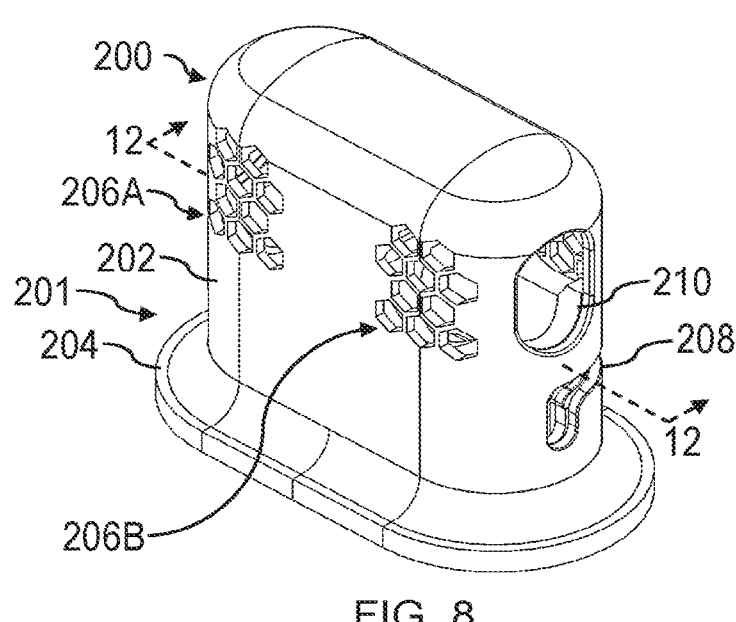
FIG. 8 is a perspective view of the reconstitution device of FIG. 7 in an actuated state.

FIG. 7 is a perspective view of one embodiment of a reconstitution device 200 in an unactuated state, while FIG. 8 shows the reconstitution device in an actuated state. As shown in FIGS. 7-8, the reconstitution device includes a housing 201 including an upper portion 202 and a lower portion 204, arranged similarly to the housing described with reference to FIG. 2. The lower portion 204 includes an inner guide 205 which supports the upper portion 202 and allows the upper portion to slide relative to the lower portion 204. That is, the inner guide allows the upper portion to move linearly relative to the lower portion between the unactuated position shown in FIG. 7 and the actuated position shown in FIG. 8. When the upper portion is in the unactuated position, containers disposed within the upper portion may be spaced from a transfer engine disposed in the lower portion 204. That is, the containers may remain sealed and fluidly disconnected from the transfer engine. When the upper portion is moved to the actuated position shown in FIG. 8, the containers may be moved towards the transfer engine so that the containers area each pierced by a spike to bring the container into fluid communication with the transfer engine, thereby starting a reconstitution process. Such an arrangement will be described further with reference to FIGS. 11-12.

In some embodiments, the inner guide may include one or more engagement features that slidably engage with feature (s) on the upper portion 202. For example, the inner guide may have grooves shaped to receive fins of the upper portion, where the fins are slidable along the grooves. The components may be reversed such that the grooves are on the upper portion and the fins are on the inner guide. Other sliding engagement arrangements may be used, such as other rails, an elongated member running through an enclosed channel, or any other suitable sliding engagement arrangement.

According to the embodiment of FIGS. 7-8, the reconstitution device 200 include an upper stop 207 formed on the upper portion 202 of the housing 201, and a lower stop 209 formed on the lower portion 204 of the housing. The upper stop and lower stop are formed as ledges that are configured to abut one another and prevent further movement of the upper portion 202 toward the lower portion 204 when then reconstitution device is actuated. That is, the upper and lower stops define an actuated position where the upper stop and lower stop are in contact with one another. In the embodiment of FIGS. 7-8 the upper and lower stops extend along a perimeter of the upper and lower portion of housing, respectively. Of course, in other embodiments the stops may have any suitable arrangement, and the present disclosure is not so limited.

FIG. 9 is a side elevation view of the reconstitution device 200 of FIG. 7 in an unactuated state and FIG. 10A is a side elevation view of the reconstitution device in an actuated state. FIGS. 9-10B in particular show how physical access to a fluid outlet 111 of the reconstitution device may be obstructed prior to actuation. According to the specific embodiment of FIGS. 9-10B, the fluid outlet 111 may be at least partially concealed or enclosed within the housing 201 prior to actuation. Upon actuation, the fluid outlet 111 may be exposed so that it may be accessed by a delivery device once a medicinal fluid is reconstituted. As shown in FIG. 9, the upper portion 202 of the housing includes a slot 208 and a cutout 212 that form an opening in the upper portion of the housing. However, in the position shown in FIG. 9, nothing is accessible through the cutout 212 or slot 208 except for some of the inner guide 205 of the lower portion 204 of the housing 201. However, when the upper portion is moved toward the lower portion, the cutout 212 aligns with the fluid outlet 111, thereby permitting physical access and removal of the fluid outlet. As shown in FIG. 9, the fluid outlet 111 is disposed in a fluid outlet receptacle 213 formed in the lower portion 204. Accordingly, as the cutout 212 aligns with the fluid outlet receptacle 213, the fluid outlet 111 is accessible and removable from the fluid outlet receptacle through the cutout 212. To facilitate removal, the fluid outlet includes a flexible leash 112. User access to the flexible leash 112 may be permitted upon alignment of the cutout 212 with the fluid outlet receptacle 213. In some embodiments, the leash may at least partially unfurl when the cutout is aligned with the fluid outlet receptacle. The leash may allow a user to pull on the fluid outlet 111 from outside the housing 201, thereby facilitating its removal. According to the embodiment of FIGS. 10A-10B, the fluid outlet is connected to an associated transfer engine via flexible tubing 114, which allows the fluid outlet to be removed and manipulated while the housing 201 remains stationary. The flexible tubing 114 is aligned with the slot 208, which allows a portion of the flexible tubing to be released through the slot to allow the fluid outlet to be manipulated. Accordingly, in the embodiment of FIGS. 10A-10B, once multiple containers are pierced the fluid outlet 111 may be exposed and accessible to a user to connect a delivery device. Such an arrangement may ensure a medicinal fluid is at least partially reconstituted before a delivery device is connected.

As shown in FIG. 10B, the fluid outlet 111 is disposed in the fluid outlet receptacle 213 and is physically accessible to a user when the reconstitution device is actuated. According to the embodiment of FIG. 10B, the fluid outlet 111 is a luer activated device including external threads 113 configured to receive corresponding threads of a syringe or other delivery device. The fluid outlet 111 includes a flexible leash 112 that is configured to be folded inside the reconstitution device housing and then unfurls when the device is actuated. The leash 112 may be formed of any suitable flexible material, including a plastic film, rubber, etc. A user may pull on the leash to remove the fluid outlet 111, which may otherwise be difficult to grasp and remove from the fluid outlet receptacle 213. In some embodiments, the leash 112 may be disposed on the flexible tubing 114 instead of the fluid outlet 111 so that the flexible tubing may be used to remove the fluid outlet from the fluid outlet receptacle. In some embodiments, the leash may be a molded sleeve which fits over at least a portion of the fluid outlet 111 and provides a region in which a user can grasp the leash and use it to remove the fluid outlet from the fluid outlet receptacle.

Of course, while one embodiment of a housing selectively permitting physical access to a fluid outlet is shown and described with reference to FIGS. 9-10B, other suitable configurations are contemplated. For example, in one embodiment, an upper housing may not include a cutout, but may instead move a wall of the upper housing out of alignment with a fluid outlet receptacle. In another embodiment, a moveable component (e.g., cam, door, etc.) may be moved concurrently with the actuation of a housing of a reconstitution device, thereby providing physical access to a fluid outlet only after actuation. In some embodiments, a fluid outlet may be visible to a user prior to actuation of a reconstitution device, but may be at least partially obstructed so that the fluid outlet may not be physically accessed. In one such embodiment, a fluid outlet receptacle may have an opening that is partially open when the reconstitution device is unactuated. When the reconstitution device is actuated, the opening of the receptacle may be widened or otherwise opened further so that the fluid outlet may be physically accessed through the opening. Of course, the fluid outlet may be retained in any suitable portion of a reconstitution device housing prior to actuation of the device, including a lower portion of a housing or upper portion of a housing, as the present disclosure is not so limited. In some embodiments, an upper portion of the housing is shaped as shown in the embodiment of FIGS. 9-10B, but the housing is transparent such that the fluid outlet is visible but not physically accessible prior to device actuation.

Figure 11:
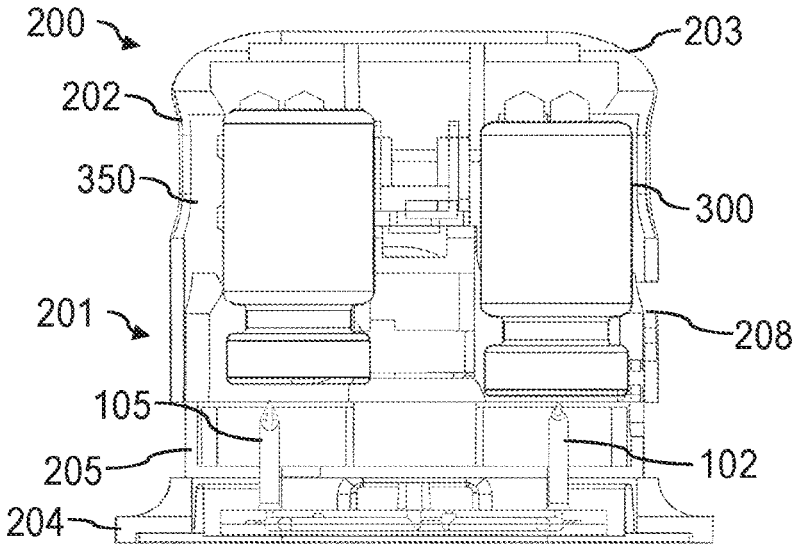
FIG. 11 is a cross-sectional view of the reconstitution device of FIG. 7 taken along line 11-11.
Figure 12:
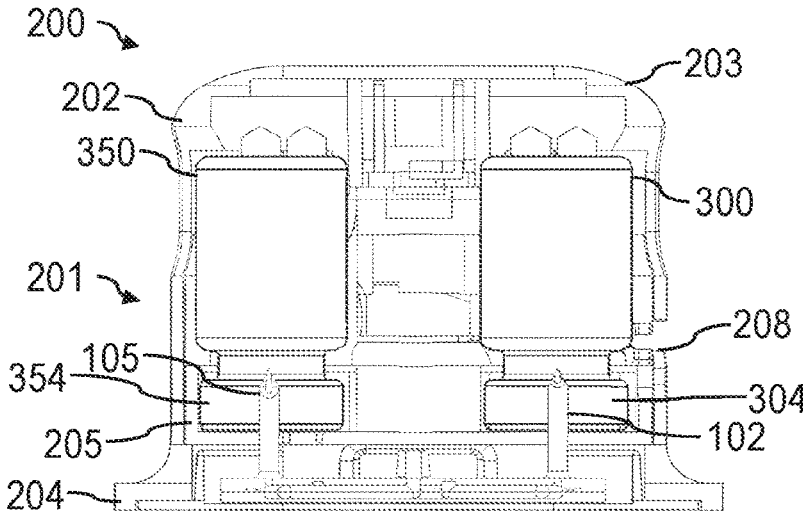
FIG. 12 is a cross-sectional view of the reconstitution device of FIG. 8 taken along line 12-12.

FIG. 11 is a cross-sectional view of the reconstitution device of FIG. 7 taken along line 11-11 showing the reconstitution device with containers in an unactuated state, while FIG. 12 is a cross-sectional view of the reconstitution device of FIG. 8 taken along line 12-12 showing the reconstitution device with containers in an actuated state. As shown in FIG. 11 and discussed previously, the reconstitution device includes a housing 201 having an upper portion 202 and a lower portion 204. The lower portion is slidably disposed in the upper portion, with an inner guide 205 providing the sliding interface with the upper portion. As shown in FIGS. 11-12, a first container 300 and second container 350 are disposed in the upper portion 202. In FIG. 11, the first and second containers are spaced from a first spike 102 and second spike 105, respectively, of a transfer engine such that the first and second containers remained sealed. In FIG. 12, the first and second containers are moved toward the spikes 102, 105 such that the spikes pierce a stopper 304 of the first container and a stopper 354 of the second container simultaneously. When moving from the unactuated position to the actuated position, a user may place the lower portion 204 of the housing 201 on a flat surface to serve as a base. The user may then apply a force to the curved top surface 203 of the housing to move the upper portion 202 towards the lower portion 204, thereby moving the first and second containers 300, 350 into contact with the spikes. Once the first and second containers are pierced, a reconstitution process may begin, an exemplary embodiment of which was described previously with reference to FIGS. 3-6.

It should be noted that while a particular embodiment of a housing 201 is shown in FIGS. 11-12, the housing may take any suitable shape to allow two containers to be selectively moved towards one or more container receiving ends of a fluid transfer engine. For example, in one embodiment, the upper portion of the housing may be received inside of the lower portion. As another embodiment, the top surface 203 of the housing may not be curved or may be curved to a lesser extent. Additionally, the upper housing may include one or more retaining features to secure the first container 300 and second container 350 therein. For example, tabs, projections, and/or shelves corresponding to a shape of the containers may be employed to retain the spacing between the containers and the transfer engine. Additionally, in some embodiments, one or more biasing members may be employed to bias the reconstitution device toward an unactuated position, such that a threshold force must be applied to the upper portion to actuate the reconstitution device.

In some embodiments, the transfer engine may be a distinct component from the lower portion of the housing. That is, the transfer engine and housing of a reconstitution device may be formed separately. The lower portion of the housing may include a slot or transfer engine receiving portion configured to receive the transfer engine. The transfer engine may be secured to the lower portion with any suitable configuration, including, but not limited to, mechanical fasteners (e.g., screws, bolts, etc.), snap-fit tabs, and adhesives (e.g., glue, epoxy, etc.). Such an arrangement may allow the fluid pathway of the transfer engine to be sterilized prior to being assembled with a reconstitution device housing. In some embodiments, reconstitution devices include other components that may be sensitive to certain sterilization processes, such as containers of medicament or electronics. In some embodiments, having a transfer engine that can be separately sterilized prior to assembly with the device housing may avoid the need to sterilize the reconstitution device in its entirety, and thus components that are sensitive to certain sterilization processes need not be exposed to such processes.

In some embodiments, a reconstitution device may be stored and transported in a packaging container. The packaging container may be formed as a clamshell or blister pack which has a shape corresponding to the shape of a housing of the reconstitution device. The packaging container may also include one or more projections or tabs which block an upper portion of the housing from moving relative to the lower portion of the housing, or vice versa. That is, the one or more projections or tabs may engage the upper portion to retain it in an unactuated position. Such an arrangement may ensure a reconstitution device is not inadvertently actuated during transportation and storage.

In some embodiments, a reconstitution device having a housing with an upper portion and lower portion that are movable relative to one another between an actuated and unactuated position may include one or more locking latches that, after actuation of the device, permanently lock the housing in an actuated position. For example, in one embodiment, latches disposed in a lower portion of the housing may capture and permanently retain an upper portion of the housing when the upper housing is moved to an actuated position. The latches may be disposed inside of the housing so that they are not accessible to a user. Accordingly, the housing may be effectively locked in the actuated position, and the upper portion cannot be moved back to the unactuated position non-destructively. Such an arrangement may inhibit a user from taking a reconstitution device apart or discourage attempts to retrieve used containers from the reconstitution device.

Figure 13:
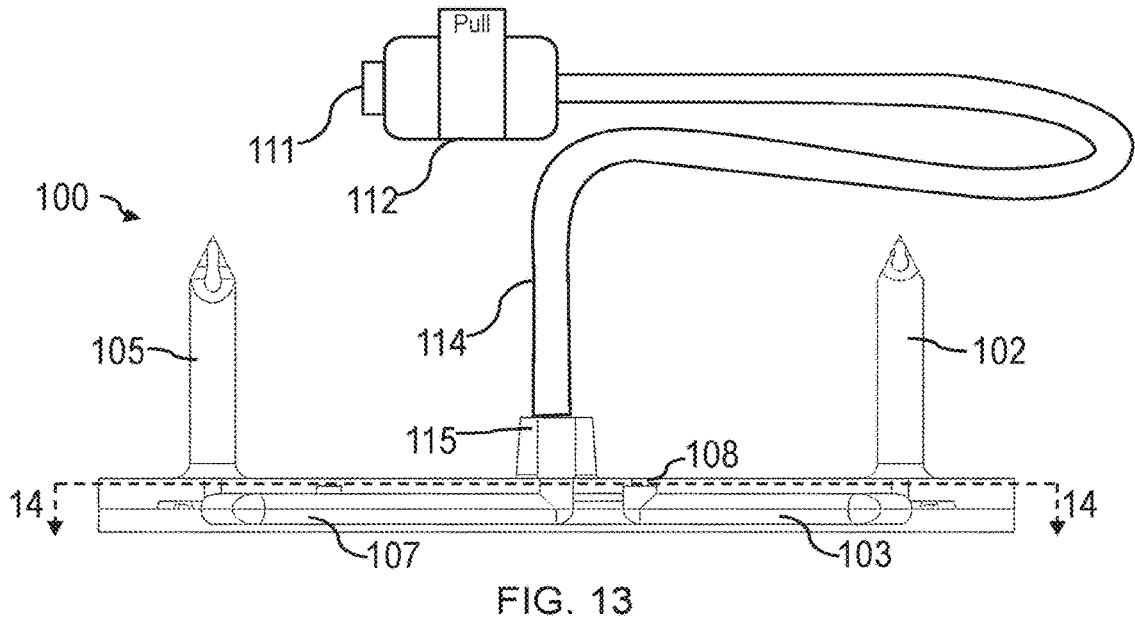
FIG. 13 is a side elevation view of one embodiment of a transfer engine of a reconstitution device.

FIG. 13 is a side elevation view of one embodiment of a transfer engine 100 of a reconstitution device. As shown in FIG. 13, the transfer engine includes a first spike 102 and a second spike. Similarly to the schematic described with reference to FIG. 1, the first spike 102 is associated with an air inlet 108 and a first fluid path 103. The air inlet includes a hydrophobic filter that allows air into the first fluid path 103, while preventing fluid from escaping the first fluid path. The second spike 105 is associated with a third fluid path 107 which extends to a fluid outlet connector 115. A second fluid path extends between the first spike 102 and second spike 105, as will be discussed further with reference to FIG. 14. According to the embodiment of FIG. 13, the fluid outlet 111 is connected to the third fluid path 107 via flexible tubing 114, such that the fluid outlet may be moved relative to the first spike and second spike. The fluid outlet 111 is configured as a luer activated valve, and includes a leash 112 configured to assist a user in removing the fluid outlet from a reconstitution device housing. According to the embodiment of FIG. 13, the fluid outlet 111 is adjacent to the air inlet 108, such that the transfer engine effectively forms a geometric circuit. Additionally, in some embodiments as shown in FIG. 13, portions of all of the fluid paths are coplanar with one another in the transfer engine.

In some embodiments, each of the spikes 102, 105 of the transfer engine 100 may have a corresponding sheath configured to seal and/or protect the fluid paths disposed in the transfer engine. The sheaths may be arranged to be compressible and are broken by the spikes 102, 105 when containers are pierced by the spikes. Such an arrangement may help the sterilized fluid paths of the transfer engine remain sterile during storage and transport of a reconstitution device. Additionally, the sheaths may provide a fluid seal for the spikes that prevent loss of any reconstitution fluid or medicament in an instance where one container is pierced and fluidly connected to the transfer engine before the other.

Figure 14:
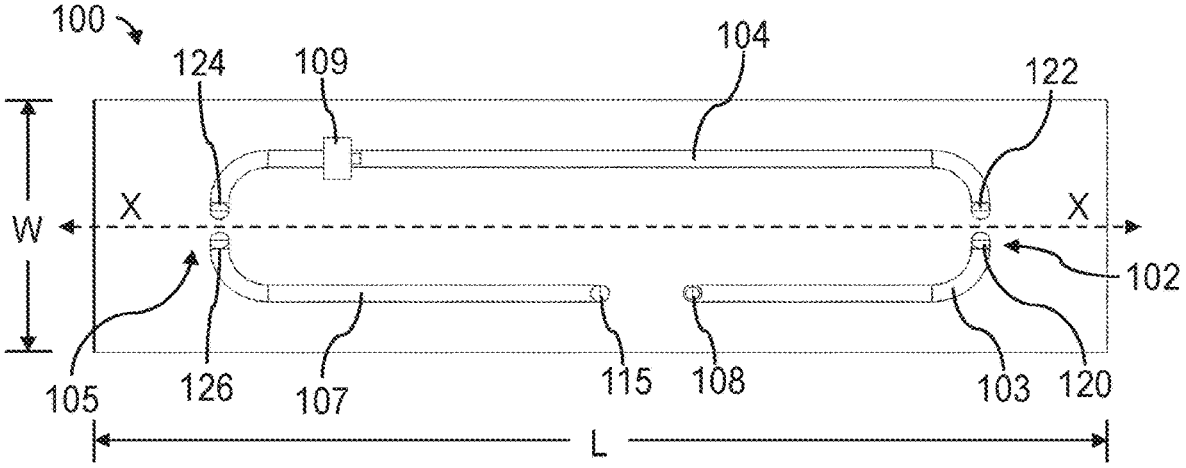
FIG. 14 is a top cross-sectional view of the transfer engine of FIG. 13 taken along 14-14.

FIG. 14 is a top cross-sectional view of the transfer engine 100 of FIG. 13 taken along 14-14 showing the geometric arrangement of the various fluid paths. As shown in FIG. 14, the first fluid path 103 extends between the air inlet 108 and the position of the first spike 102. The first fluid path 103 defines a first lumen 120 in the first spike. The second fluid path 104 defines a second lumen 122 in the first spike and a third lumen 124 in the second spike 105. A check valve 109 is positioned along the second fluid path 104. Finally, a third fluid path 107 defines a fourth lumen 126 in the second spike, and extends to the fluid outlet connector 115. As noted previously, the fluid outlet connector may receive flexible tubing which creates a continuous fluid path to a movable fluid outlet.

According to the embodiment of FIG. 14, the transfer engine 100 is arranged in a compact rectangular shape. The parallel, circuit-like arrangement of the fluid paths and first and second spikes 102, 105 is such that the size of a reconstitution device containing the transfer engine may be reduced for case of transport and handling. That is, at least part of the fluid pathway is curved onto itself, rather than extending in a single linear path. As shown in FIG. 14, portions of the first fluid path 103, second fluid path 104, and third fluid path 107 are all parallel to one another. Indeed, each of the fluid paths has a portion parallel to a longitudinal axis X-X of the transfer engine. Furthermore, according to some embodiments as shown in FIG. 14, at least a portion of the first fluid path 103 may be mirrored across the longitudinal axis X-X to form at least a portion of the second fluid path 104. Likewise, at least a portion of the second fluid path 104 may be mirrored across the longitudinal axis X-X to form the third fluid path 107. Accordingly, the fluid paths are at least partially symmetrical across the longitudinal axis to reduce the overall size of the transfer engine. It should be noted that while the first, second, and third fluid paths of FIG. 14 include curved portions where the fluid path changes directions, any suitable arrangement may be employed to change the direction of the fluid path. For example, in some embodiments, the fluid paths may include one or more angular portions transition the direction of the fluid path.

While a rectangular shaped transfer engine is shown in the embodiment of FIG. 14, in other embodiments a transfer engine may take any suitable shape. For example, a transfer engine may be circular, elliptical, square, or another suitable shape, and the present disclosure is not so limited in this regard.

According to the embodiment of FIG. 14, the transfer engine 100 may have a rectangular size well-suited for placement in a compact reconstitution device. That is, the overall width W of the transfer device is less than an overall length L of the transfer device. In particular, according to the embodiment of FIG. 14, a ratio between the length L and the width W may be between 3 and 5. Accordingly, the length of the transfer engine may be between 3 and 5 times longer than the width of the transfer engine, making it well-suited for accommodating linearly arranged containers. As the transfer engine may include a movable fluid outlet that is connected via flexible tubing (see FIG. 13), the fluid paths extending between the spikes 102, 105, inlet 108, and fluid outlet connector 115 may be arranged in parallel to reduce the overall size of a reconstitution device employing a transfer engine. Put another way, the first fluid path 103 and third fluid path 107 wrap around to run in parallel to the second fluid path 104, thereby reducing overall length of the transfer engine without a substantial increase in width. Of course, in other embodiments any appropriate length to width ratio may be employed, as the present disclosure is not so limited.

FIG. 15 is a flow chart of one embodiment of a reconstitution and medicinal fluid delivery process. At step 500, first and second containers are provided within a housing, where an upper portion of the housing at least partially encloses the first and second containers. The first and second container may include a reconstituting fluid and a medicament for reconstitution, respectively. In some embodiments, step 500 may be omitted, and the process may start at step 502. At step 502, force is applied to the upper portion of the housing, moving the upper portion from a first unactuated position to a second actuated position. Applying the force to the upper portion may include applying force to the upper portion in a linear direction toward a flat surface on which the housing is placed. At step 504, the first container is pierced with a first spike, and the second container is pierced with a second spike as the upper portion is moved to the actuated position. At step 506, fluid is allowed to flow from the first container to the second container to occupy a vacuum in the second container. Allowing the fluid to flow to the second container may include moving the fluid past a check valve disposed between the first and second spikes and expelling the fluid into the second container at a speed that may help to facilitate reconstitution. At step 508, the fluid is mixed with a drug product or medicament in the second container to create a medicinal fluid. At step 510, a syringe (or other delivery device) is coupled to a fluid outlet to withdraw medicinal fluid from the second container.

Figure 16:
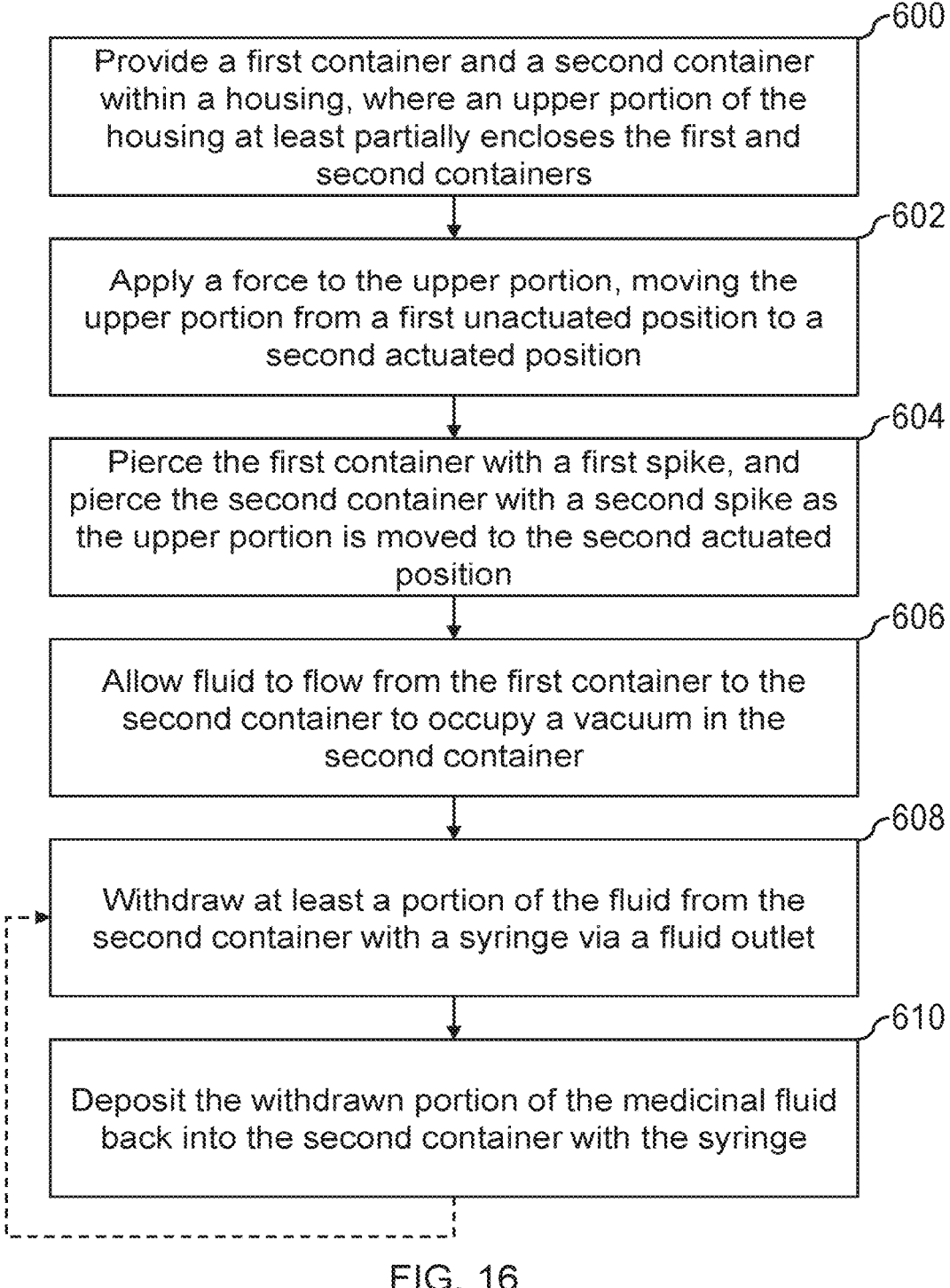
FIG. 16 is a flow chart of another embodiment of a reconstitution and medicinal fluid delivery process.

FIG. 16 is a flow chart of another embodiment of a reconstitution and medicinal fluid delivery process. At step 600, first and second containers are provided within a housing, where an upper portion of the housing at least partially encloses the first and second containers. The first and second container may include a reconstituting fluid and a medicament for reconstitution, respectively. In some embodiments, step 600 may be omitted, and the process may start at step 602. At step 602, force is applied to the upper portion of the housing, moving the upper portion from a first unactuated position to a second actuated position. Applying the force to the upper portion may include applying force to the upper portion in a liner direction toward a flat surface on which the housing is placed. At step 604, the first container is pierced with a first spike, and the second container is pierced with a second spike as the upper portion is moved to the actuated position. At step 606, fluid is allowed to flow from the first container to the second container to occupy a vacuum in the second container. Allowing the fluid to flow to the second container may include moving the fluid past a check valve disposed between the first and second spikes and expelling the fluid into the second container at a speed that may help to facilitate reconstitution. At step 608, a syringe is coupled to a fluid outlet to withdraw at least a portion of medicinal fluid from the second container. For example, in one embodiment, a syringe handle may be moved away from the fluid outlet. At step 610, the withdrawn portion of medicinal fluid is deposited back into the second container with the syringe. For example, step 610 may be accomplished by pressing the syringe handle towards the fluid outlet, increasing the pressure of the medicinal fluid.

In some embodiments, steps 608 and 610 shown in FIG. 16 may be employed in processes in which there is no vacuum or an insufficient vacuum in the second container to draw the reconstituting fluid from the first container into the second container. In such an embodiment, the syringe may be used to draw fluid from the first container, into the second container, and finally into the syringe. Once the fluid is at least partially disposed within the syringe, the withdrawn portion of the fluid may be deposited back into the second container to mix the contents of the first container and second container together, and the process may be repeated until the contents of the first container and second container are sufficiently mixed.

Figure 17:
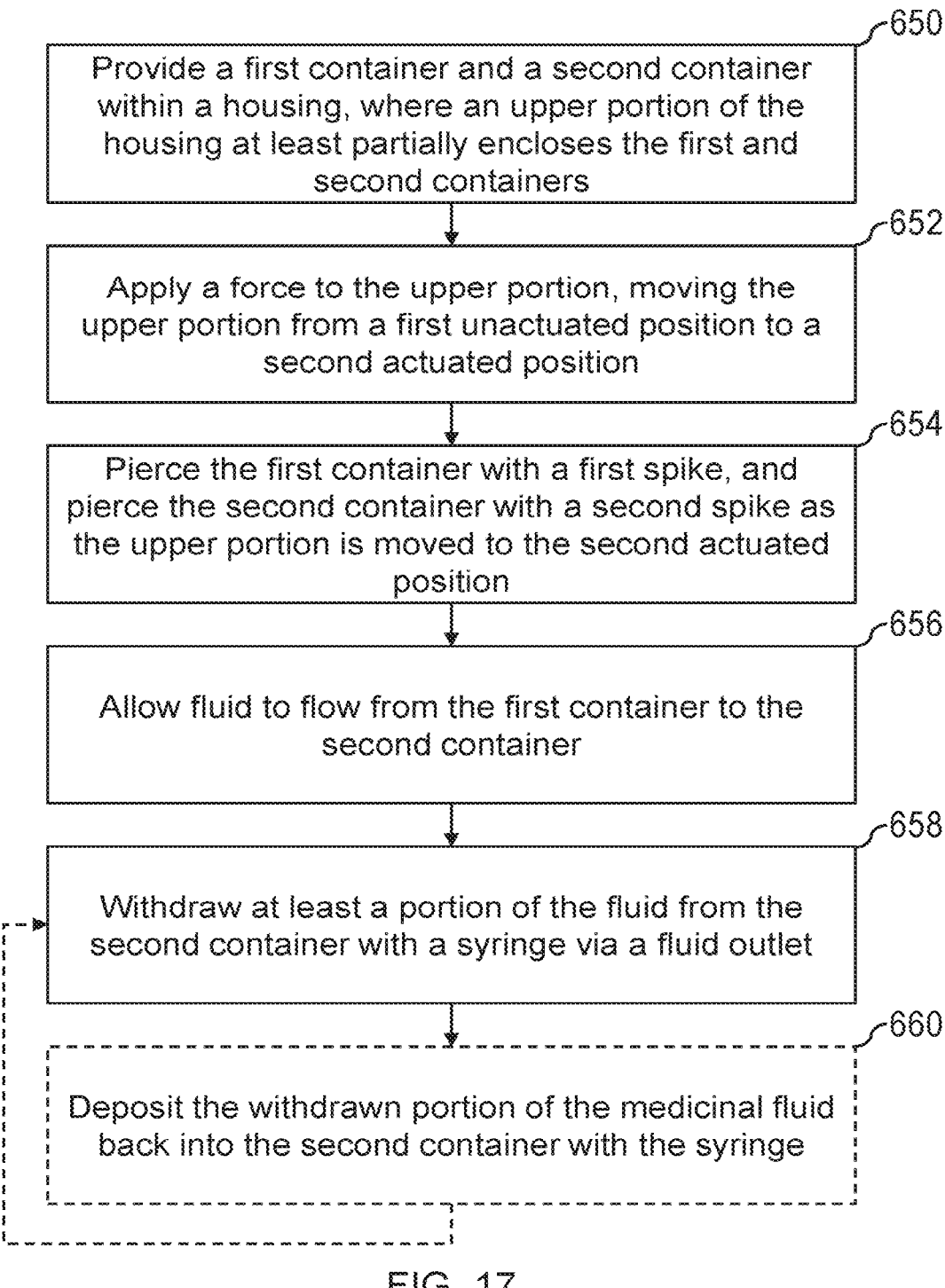
FIG. 17 is a flow chart of another embodiment of a reconstitution and medicinal fluid delivery process.

FIG. 17 is a flow chart of another embodiment of a reconstitution and medicinal fluid delivery process. At step 650, first and second containers are provided within a housing, where an upper portion of the housing at least partially encloses the first and second containers. The first and second containers may include a reconstituting fluid and a liquid medicament for reconstitution, respectively. In some embodiments, step 650 may be omitted, and the process may start at step 652. At step 652, force is applied to the upper portion of the housing, moving the upper portion from a first unactuated position to a second actuated position. Applying the force to the upper portion may include applying force to the upper portion in a linear direction toward a flat surface on which the housing is placed. At step 654, the first container is pierced with a first spike, and the second container is pierced with a second spike as the upper portion is moved to the actuated position. At step 656, fluid is allowed to flow from the first container to the second container. According to the embodiment of FIG. 17, the fluid may not automatically flow from the first container to the second container. Nevertheless, the reconstituting fluid and liquid medicament may at least partially mix once the containers are pierced. At step 658, a syringe is coupled to a fluid outlet to withdraw at least a portion of medicinal fluid from the second container. For example, in one embodiment, a syringe handle may be moved away from the fluid outlet. At step 658, all of the liquid medicament and reconstituting fluid may be drawn into the syringe in a single draw. At optional step 660, the withdrawn portion of medicinal fluid is deposited back into the second container with the syringe. For example, step 660 may be accomplished by pressing the syringe handle towards the fluid outlet. Step 660 may be employed if the medicament and reconstituting fluid are not sufficiently mixed. In some cases, steps 658 and 660 may be repeated to more thoroughly mix the reconstituting fluid and medicament.

Figure 18:
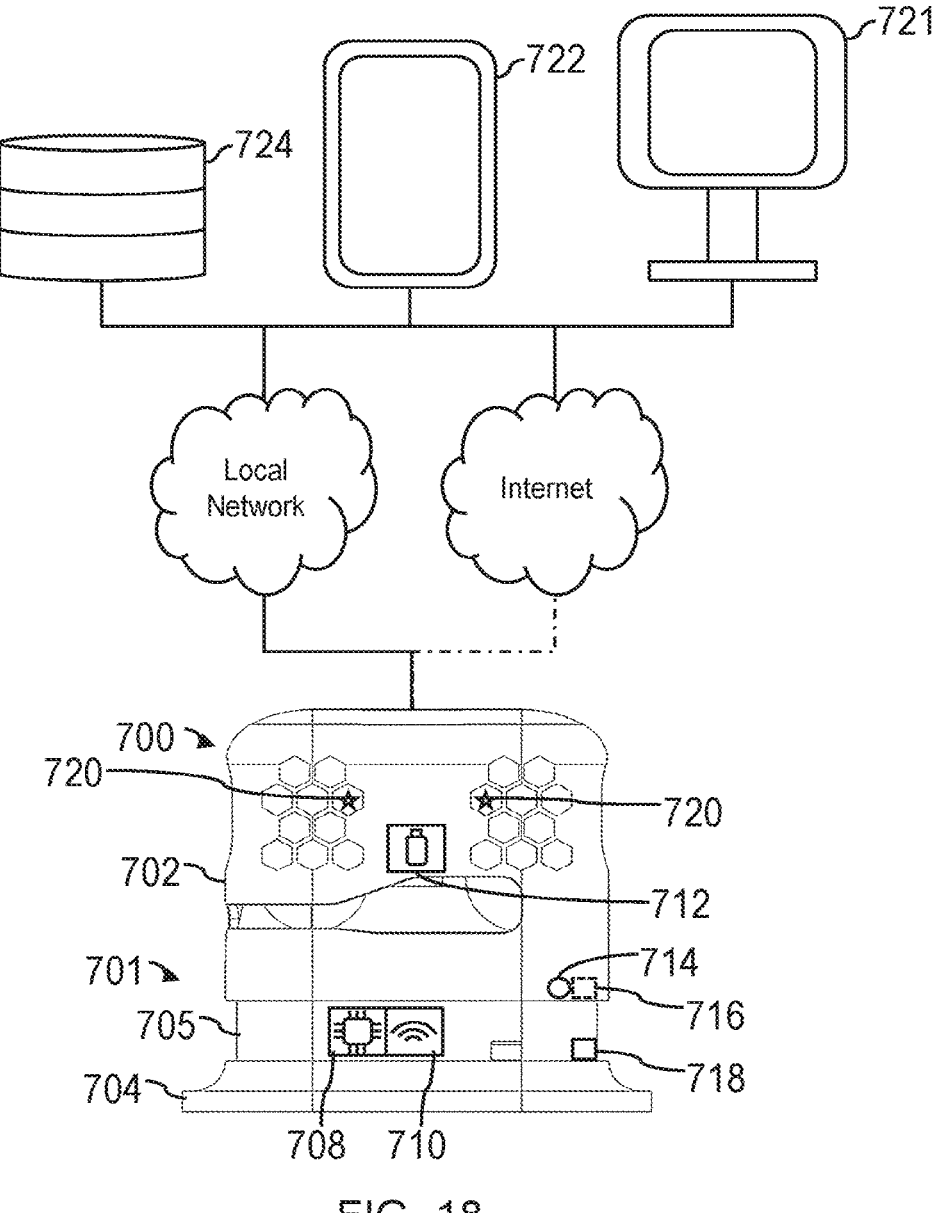
FIG. 18 is a schematic of one embodiment of a reconstitution device in communication with one or more remote devices.

FIG. 18 is a schematic of one embodiment of a reconstitution device 700 in communication with one or more remote devices. As shown in FIG. 18, the reconstitution device is similar in shape and size to the reconstitution device described with reference to FIG. 2. The reconstitution device includes a housing 701 including an upper portion 702 and a lower portion 704. The upper portion is configured to slide relative to the lower portion, and an inner guide 705 is received in the upper portion to support and guide the upper portion as it slides between an unactuated position and an actuated position. According to the embodiment of FIG. 18, the reconstitution device 700 includes a processor 708 (e.g., programmable logic controller) disposed in the lower portion 704, along with a communication device 710 and an internal power source configured as a battery 712. The processor is configured to execute a series of one or more computer readable instructions stored in volatile or non-volatile memory disposed on the lower portion 704. The communication device is configured to transmit signals by at least one of a wired and wireless protocol. For example, the communication module may be configured as a wireless transceiver configured to communicate with one or more remote devices with one or more of Bluetooth, Bluetooth Low-Energy. Wi-Fi, 802.15.4, ZigBee, GSM, HSPA, CDMA, and/or any other suitable protocol. The battery 712 may be any suitable battery, such as a NiMH. Li-Ion, or Alkaline battery, as the present disclosure is not so limited.

In some embodiments, a reconstitution device may include a marker such as a QR code or other identifying label (e.g., a barcode). Such a marker may be employed to allow the reconstitution device to be linked to an application (e.g., smartphone application) or otherwise tracked by a complementary remote device (e.g., a smartphone). In some embodiments, scanning the QR code with an appropriate reader or camera may import information regarding the dosage of a medicament, drug identity, and/or volume of a medicament disposed in the reconstitution device into the complementary remote device for display to a user. The complementary device may also track timing, dosage, frequency, drug lot information, and other medically relevant parameters to enable a user or physician to monitor an extended therapeutic process. In some embodiments, the QR code or other marker may be hidden from view inside of a reconstitution device housing or otherwise obstructed from being accessed prior to device actuation. Once the device is actuated, the QR code may be revealed or otherwise accessible to be scanned by a user.

According to some embodiments and as shown in FIG. 18, the electronics of the reconstitution device may only be activated once the reconstitution device is actuated. That is, the processor 708 and communication device 710 may be dormant, sleeping, or electrically disconnected from the power source when the upper portion 702 is in the unactuated position. When the upper portion 702 is moved to an actuated position (e.g., closer to the lower portion 704 such that, for example, a bottommost surface of the upper portion is closer to a base of the lower portion), one or more switches may be triggered to wake or connect the processor and communication device to the power source. Accordingly, the onboard power source may not be drained during transportation and storage and may retain a charge sufficient to power the reconstitution device when the device is actuated. According to the embodiment of FIG. 18, the reconstitution device includes a first Hall Effect sensor 716 and a second Hall Effect sensor 718 disposed in the lower portion 704 of the housing. The Hall Effect sensors are configured to sense the immediate presence of a magnet 714 disposed on the upper housing. That is, the first Hall Effect sensor is configured to sense when the upper portion 702 is in the unactuated position, while the second Hall Effect sensor is configured to sense when the upper portion 702 is in the actuated position. When the magnet 714 is moved adjacent to the second Hall Effect sensor 718, the processor 708 and communication device 710 may be activated. Of course, while Hall Effect sensors are shown in FIG. 18, any suitable switch or sensor may be employed to determine the position of the upper portion, including, but not limited to, a linear potentiometer or a micro-switch.

In some embodiments and as shown in FIG. 18, the reconstitution device 700 may include one or more visual indicators 720 configured as LEDs that indicate one or more states of the reconstitution device to a user. The visual indicators may be controlled by the processor 708 and may be activated by the movement of the upper portion 702 to the actuated position. The visual indicators may indicate one or more states of the reconstitution device as a reconstitution process is ongoing. For example, in one embodiment, the at least one indicator may indicate when the reconstitution device is actuated and a reconstituting fluid is flowing and mixing with a medicament. In another example, the at least one indicator may indicate when the reconstituting fluid has had suitable time to mix with the medicament based on input from a real time clock module, thereby indicating when a medicinal fluid is suitable to withdraw from the reconstitution device with a delivery device (e.g., syringe). According to one such example, the one or more visual indicators 720 may show a first color as the reconstituting fluid is mixing with the medicament, and show a second color once the reconstituting fluid has had a predetermined time to mix with the medicament. In another such example, the one or more visual indicators 720 may blink in a first pattern as the reconstituting fluid is mixing with the medicament, and blink in a second pattern or display a solid color once the reconstituting fluid has had a predetermined time to mix with the medicament. In yet another example, the reconstitution device may include an orientation sensor (e.g., accelerometer, gyroscope, etc.) and the indicator may indicate when the reconstitution device is in a predetermined orientation, or conversely, when the reconstitution device is in an orientation different than the predetermined orientation. Of course, any of the above examples may be employed alone or in any combination with one another for relaying desired information to a user, as the present disclosure is not so limited.

The indication of states by the visual indicator may be coordinated by the processor 708, which may receive and process information from one or more sensors. In some embodiments, the visual indicators may be color coded to relay the general state of the reconstitution device during a reconstitution process. For example, the visual indicators may illuminate red for an error state, yellow for a when a reconstituting fluid is mixing with a medicament inside of the device, and green for when a medicinal fluid is ready to be withdrawn from the device. Of course, any suitable color or blinking pattern may be used to indicate any desirable state, as the present disclosure is not so limited. In some embodiments, the communication device 710 may also communicate the state of the reconstitution device to a remote device, as described further below. In some embodiments, the reconstitution device may include one or more light sources configured to illuminate containers disposed within the reconstitution device.

According to the embodiment of FIG. 18, the reconstitution device 700 is configured to communicate with one or more remote devices, including, but not limited to a personal computer 721, mobile device 722, and remote server 724. Information relayed through such communication may be shared with one or more parties, which may use the information in different ways. Communication may be one-way in either direction, or two-way. The communication may utilize any suitable number of local or external networks, including the internet, to communicate with the remote devices. For example, in some embodiments, the reconstitution device may use a short-range communication protocol to communicate with a base station or local relay, such as Bluetooth, ZigBee, infrared transmission, and radio frequency (RF) communication. As such, if the reconstitution device lacks longer range communication capabilities such as Wi-Fi. or cellular network technology, or if the user has not activated these communication capabilities, then the reconstitution device may still communicate wirelessly with the local relay. In some embodiments, the reconstitution device may also use a short-range communication protocol to communicate wirelessly with nearby external devices such as a mobile device. In some embodiments, the reconstitution device may communicate wirelessly over longer distances to other external devices such as directly to a remote server 724 or personal computer 721. In some embodiments, the reconstitution device may send messages including information to one or more remote devices. The information may include time information, dosage, drug lot information, and other medically relevant parameters. In some embodiments, the reconstitution device may include a global positioning system (GPS) sensor configured to provide location information to the processor 708. In such an embodiment, the information may include location information from the GPS sensor. In some embodiments, the reconstitution device may include an accelerometer configured to detect motion and/or orientation of the reconstitution device. In such an embodiment, the information may include orientation, average acceleration, etc. from the accelerometer. In some embodiments, the reconstitution device may include a temperature sensor configured to detect a temperature of the reconstitution device. In such an embodiment, the information may include current temperature, average temperature, peak high temperature, peak low temperature, etc. from the temperature sensor.

In some embodiments, the reconstitution device 700 may directly and/or indirectly interact with a multitude of different parties that may utilize information from the reconstitution device and/or send commands or other information to the reconstitution device. As a first example, information from the reconstitution device may be sent directly or indirectly to a patient. A patient may obtain the information from the visual indicators 720 on the reconstitution device, from a mobile device 722 that may be running a companion application to the reconstitution device, or from a remote server 724. As an example, a patient may use a mobile device to obtain information from the remote server 724 via an internet website or other program. In some embodiments, the user may have access to a "patient service" feature that may serve as a type of customer service to the user. The user can connect with this service via a phone call, text, website, live chatting or other suitable communication format for assistance relating to the reconstitution device and/or the medication. As an example, in some embodiments, the patient can use the patient service feature to receive training on how to use the reconstitution device and/or any accessories relating to the reconstitution device, how to troubleshoot any issues that may have arisen, or to ask any questions relating to the reconstitution device or medication. In some embodiments, patients can use the patient service feature to help with issues relating to payment and/or insurance. The patient service may need to access information from the patient's reconstitution device in order to help the patient with some of these issues. In some embodiments, the information may be obtained from the remote server 724.

In some embodiments, the reconstitution device 700 may communicate directly or indirectly with a healthcare provider, such as a hospital, clinic, and personnel such as a nurse or physician. The healthcare provider may obtain the information from a remote server 724 or other external device such as a mobile device 722 that receives the information from the reconstitution device 700. Or, the healthcare provider may be in direct communication with the reconstitution device 700. Information that may be sent to a healthcare provider includes, but is not limited to, when a dosage was taken, how much medication was delivered, patient symptoms experienced, and so on. The healthcare provider may use the information to monitor patient adherence and/or to determine efficacy of the medication and/or the dosage regimen of the medication for the patient. From the information, the healthcare provider may, for example, choose to provide education and/or encouragement to the patient, and/or may adjust the patient's treatment. Communication between the reconstitution device and the healthcare provider may be one-way or two-way communication. For example, in some embodiments, a healthcare provider may be able to send messages such as reminders or alerts to a patient via the reconstitution device itself or to a mobile device that the patient uses in conjunction with the reconstitution device, e.g. via an application running on the mobile device that may be specific for use with the reconstitution device and/or the specific treatment that the reconstitution device is being used for. Through the application on the mobile device, or through the reconstitution device itself, a patient may be able to send questions or concerns directly to a healthcare provider, who may then provide replies back to the patient.

In some embodiments, the information communicated from the reconstitution device 700 may be integrated with a patient's Electronic Health Record. The record may include information such as when a dosage was taken, how much medication was delivered, patient symptoms experienced, and so on.

In some embodiments, the reconstitution device 700 may communicate directly or indirectly with payers, also known as insurance companies. Payers may use information from the reconstitution device to monitor aspects such as patient adherence, medication efficacy, and treatment regimen efficacy. In some embodiments, a payer may try to encourage or reward certain behaviors. For example, a payer may reward patients with good adherence by lowering rates or providing discounts. A payer may also encourage adherence by sending treatment reminders or alerts to patients and/or healthcare providers.

In some embodiments, information relayed through communication from and/or to the reconstitution device 700 may be used for data analytics, which may be used by a variety of parties. For example a supplier (e.g. a producer of a medication and/or a reconstitution device) may use information from the reconstitution device to determine what features are used most by users and when, what errors or issues are occurring, and so on. The information may be filterable into different categories such as age, gender, income, experience level, etc. In some embodiments, information gathered for data analytics may be anonymous and free of PHI (patient health information). In other embodiments, however, the information may contain PHI.

In some embodiments, information gathered from the reconstitution device 700 may help provide performance of a medication. The inventors have appreciated that, outside of clinical trials, it can be difficult to assess the performance of a medication when it has been disseminated into the wider public. Communication from reconstitution devices and other sources such as mobile devices and/or healthcare providers can help provide information regarding a medication and/or the reconstitution device's performance. Information regarding a patient's symptoms and treatment progress may be gathered from patients, e.g. via an electronic symptom diary built into a companion app running on a mobile device, and/or may be gathered from a healthcare provider's notes taken during a patient's office visit. The gathered information may help to inform future formulations and/or reconstitution device designs for the supplier, and positive performance may be used to help promote use of the medication.

In some embodiments, information relayed through communication from and/or to the reconstitution device 700 may be used to assist in supply chain management. The information may include identification of what medication was used, and when (e.g. by sending a lot/batch number or other identifier associated with the medication). Information may also include the geographical region of medication use. Such information may help a medication supplier understand supply and demand of medication, e.g. in various regions of the world, as reflected by actual use of the medication (as compared to being limited to prescription fill information). This may help the supplier understand whether more or less medication should be stocked in certain regions, whether to increase marketing efforts in certain regions, and/or whether past marketing efforts have been effective at increasing demand.

In some embodiments, the reconstitution device 700 may include a near field communication (NFC) module which allows a remote device like a smartphone to pair with the communication device 710. That is, the NFC module may relay pairing information to device with a corresponding NFC module, allowing the typical pairing process to be avoided. Such an arrangement may be beneficial to allow for reconstitution device communication without pre-pairing the device or otherwise preparing the remote device for specific use with the reconstitution device.

It should be noted that while the embodiment of FIG. 18 depicts a reconstitution device, in other embodiments a device like that of FIG. 18 may be a medicinal fluid delivery device configured to pool medicinal fluids as opposed to reconstituting a solid medicament. Accordingly, the various features and methods described with reference to FIG. 18 are also applicable to a medicinal fluid delivery device configured for pooling fluids, as the present disclosure is not so limited.

In addition to the above, it should be noted that while the device of FIG. 18 is configured for accessing and delivering the contents of two containers, any suitable number of containers may be employed. For example, in some embodiments, a medicinal fluid delivery device like that described with reference to FIG. 18 may include a single container, two containers, three containers, four containers, five containers, or any suitable number of containers. Accordingly, the various features and methods described with reference to FIG. 18 are also applicable to a medicinal fluid delivery or reconstitution device having any number of containers, as the present disclosure is not so limited.

Figure 19A:
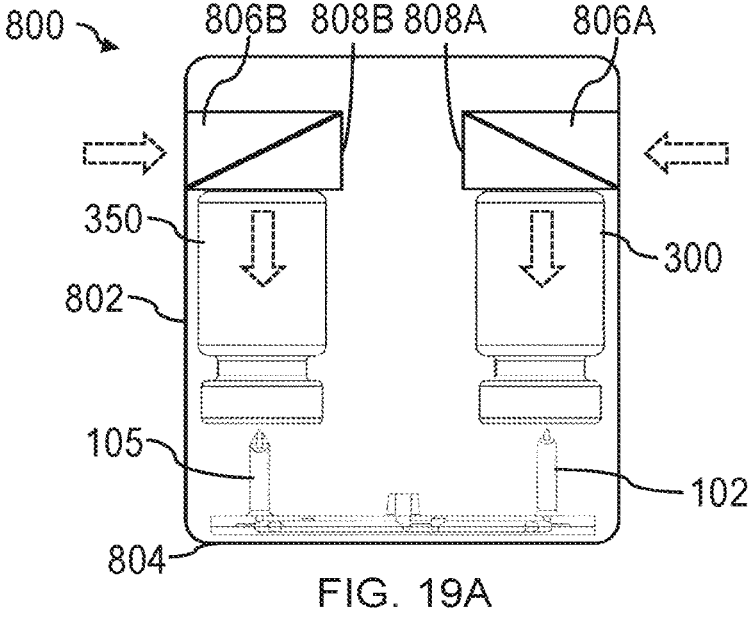
FIG. 19A is a schematic of another embodiment of a reconstitution device in a first state.
Figure 19B:
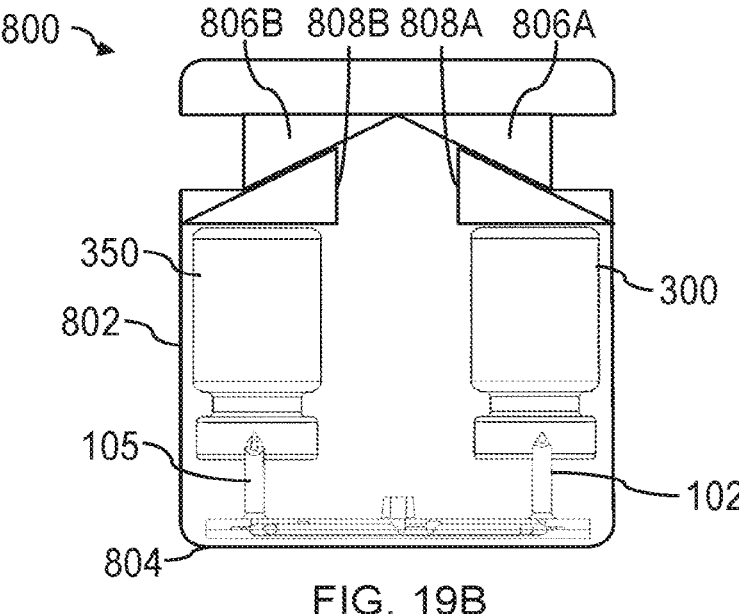
FIG. 19B is a schematic of the reconstitution device of FIG. 19A in a second state.

FIGS. 19A-19B are schematics of another embodiment of a reconstitution device 800 in an unactuated state and actuated state, respectively. According to the depicted embodiment, the reconstitution device includes a housing 802 containing a first container 300 and a second container 350. The device also includes a first actuator 806A and a second actuator 806B which are arranged as inclined planes. The first and second actuators are configured to be moved into the housing 802 to actuate the reconstitution device. In particular, the actuators are configured to move a corresponding first wedge 808A and a second wedge 808B. The first and second wedges are configured to move the first and second containers toward a base 804 of the housing 802 to be pierced by a first spike and second spike, respectively. That is, as shown in FIGS. 19A-19B, the first and second actuators may be squeezed or otherwise pressed into the housing 802 to drive the first and second wedges down toward the base 804 of the housing. As inclined planes of the actuators and wedges engage one another, sideways movement of the actuators is converted into downward movement of the wedges to drive and pierce the containers. Such an arrangement may offer mechanical advantage for piercing the containers.

Figure 20A:
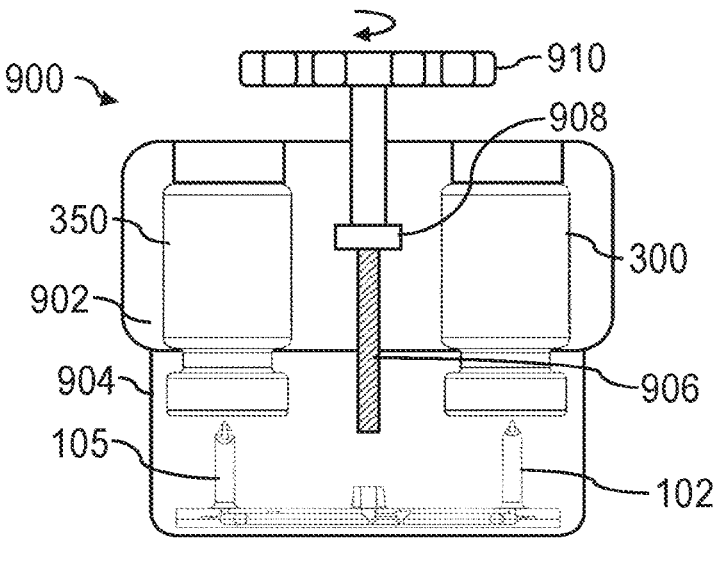
FIG. 20A is a schematic of yet another embodiment of a reconstitution device in a first state.
Figure 20B:
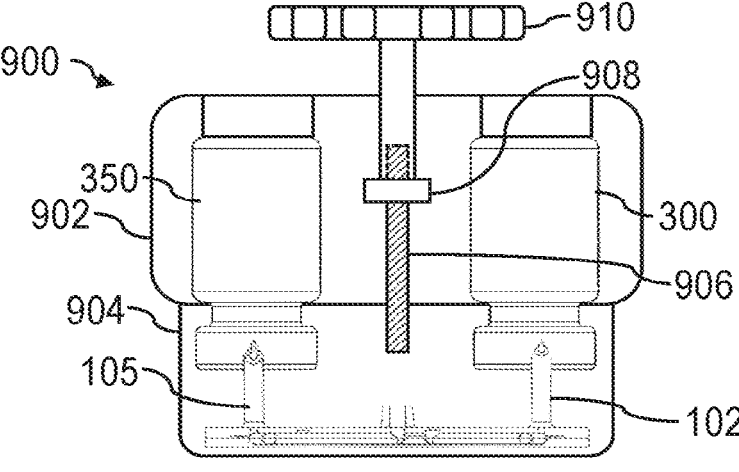
FIG. 20B is a schematic of the reconstitution device of FIG. 20A in a second state.

FIGS. 20A-20B are schematics of another embodiment of a reconstitution device 900 in an unactuated state and actuated state, respectively. As shown in FIGS. 20A-20B, the reconstitution device includes a housing with an upper portion 902 and a lower portion 904. The upper portion is movable (e.g., slidable) relative to the lower portion, where the upper portion moves toward the lower portion from an unactuated position to an actuated position. The reconstitution device includes a bolt 906 fixed to the lower portion. A nut 908 and handle 910 are threadedly coupled to the bolt and are fixed relative to the upper portion. Accordingly, a user may turn the handle 910 to move the upper portion toward the lower portion and actuate the reconstitution device. Doing so may pierce a first container 300 with a first spike 102 and a second container 350 with a second spike 105.

Figure 21A:
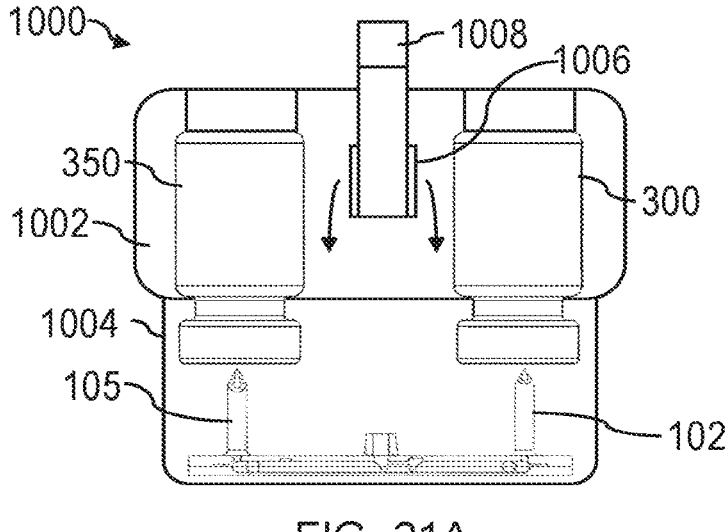
FIG. 21A is a schematic of another embodiment of a reconstitution device in a first state.
Figure 21B:
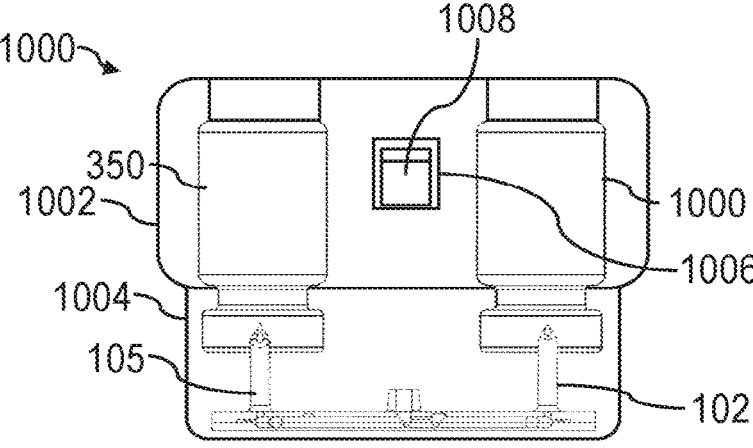
FIG. 21B is a schematic of the reconstitution device of FIG. 21A in a second state.

FIGS. 21A-21B are schematics of another embodiment of a reconstitution device 1000 in an unactuated state and actuated state, respectively. As shown in FIGS. 21A-21B, the reconstitution device includes a housing with an upper portion 1002 and a lower portion 1004. The upper portion is movable (e.g., slidable) relative to the lower portion, where the upper portion moves toward the lower portion from an unactuated position to an actuated position. The reconstitution device includes a lever 1008 which is rotatably coupled to the lower portion 1004. The lever 1008 projects out of a slot 1006 in the upper portion 1002 so that the lever may apply force to the upper portion. Accordingly, to actuate the reconstitution device the lever may be moved from the upper position shown in FIG. 21A down toward the lower portion to corresponding move the upper portion toward the lower portion. Doing so may pierce a first container 300 with a first spike 102 and a second container 350 with a second spike 105.

Figures 22, 23:
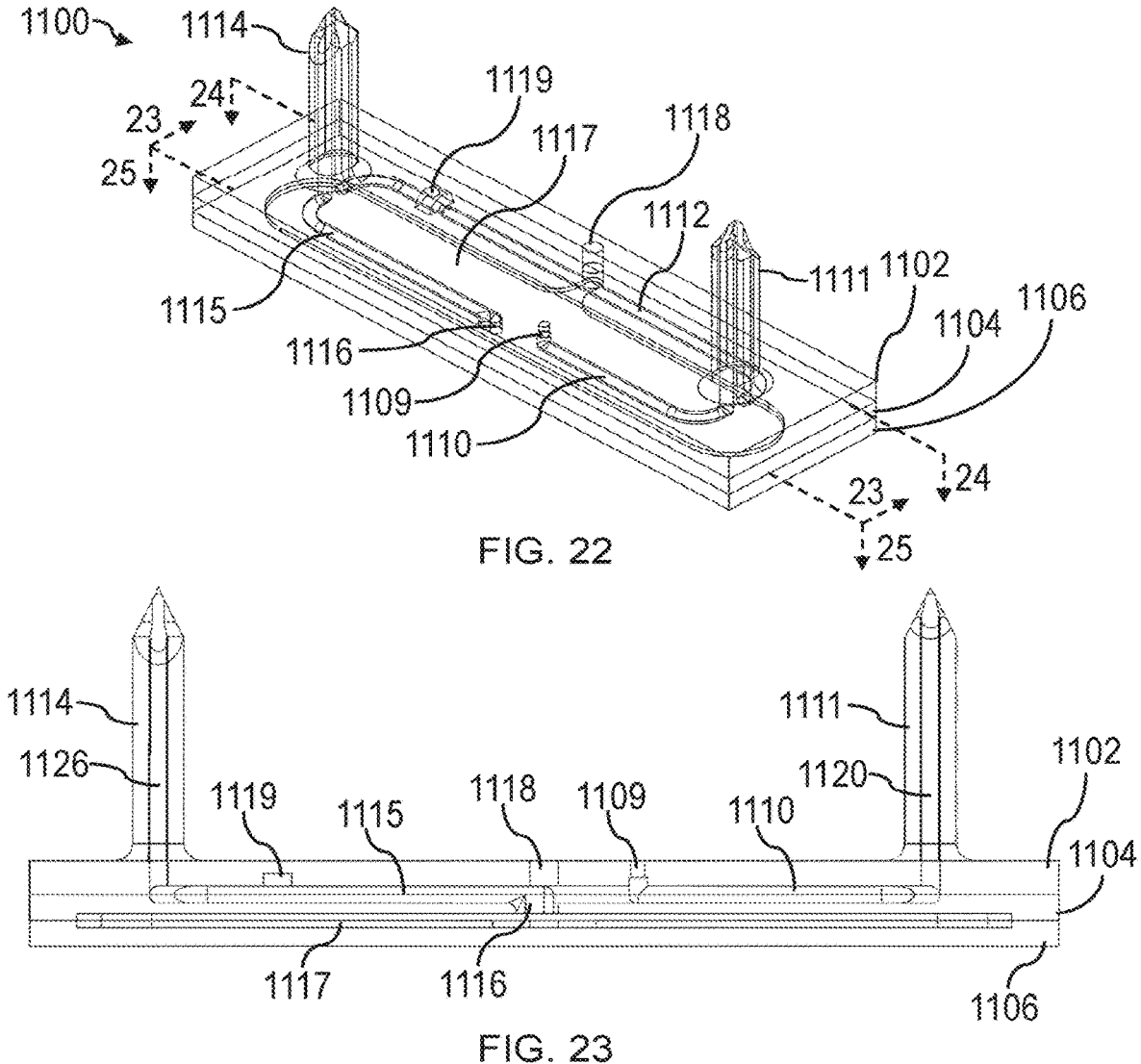
FIG. 22 is a perspective view of another embodiment of a transfer engine.
FIG. 23 is a side cross-sectional view of the transfer engine of FIG. 22 taken along line 23-23.

FIG. 22 is a perspective view of another embodiment of a transfer engine 1100. As shown in FIG. 22, the transfer engine includes a first spike 1111 and a second spike 1114 which are formed as a part of a first plate 1102. The transfer engine also includes a second plate 1104 which forms fluid pathways with the first plate, as well as a filter chamber 1117 with a third plate 1106. The transfer engine includes an inlet 1109 (e.g., air inlet) which may include a hydrophobic filter, in some embodiments. The inlet is connected to a first fluid path 1110 which curves into and extends up the first spike 1111. A second fluid path 1112 extends from the first spike 1111 to the second spike 1114. Disposed in the second fluid path is a check valve 1119 which allows one-way flow from the first spike to the second spike. A third fluid path 1115 extends from the second spike 1114 and includes a filter inlet 1116. The filter inlet allows fluid to flow from the third fluid path between the first plate 1102 and second plate 1104 to the filter chamber 1117 disposed between the second plate 1104 and the third plate 1106. A filter may be positioned in the filter chamber to effectively filter a medicinal fluid passing toward a fluid outlet. The arrangement of a filter chamber may allow for greater surface area filters to be employed. The filter chamber terminates in an outlet 1118, which may be formed as or coupled to any suitable fluid connector as discussed with reference to previous embodiments described herein.

FIG. 23 is a side cross-sectional view of the transfer engine of FIG. 22 taken along line 23-23. As shown in FIG. 23, the transfer engine is formed a three distinct plates. A first plate 1102 includes the first spike 1111 and second spike 1114. A second plate 1104 forms fluid paths with the first plate, and the filter chamber 1117 with the third plate 1106. The third plate forms the filter chamber with the second plate 1104. It should be noted that while the transfer engine of FIG. 22 is formed by three distinct plates, the transfer engine may be formed by a single unitary piece or any suitable number of components that form the various fluid paths. For example, in some embodiments a transfer engine may be formed by two distinct plates that are joined together to form a plurality of fluid paths.

As also shown in FIG. 23, the fluid paths extend into lumens of the first and second spike. That is, the first fluid path 1110 extends into a first lumen 1120 disposed in the first spike 1111. The third fluid path 1115 extends into a fourth lumen 1126 disposed in the second spike 1114.

Figures 24, 25:
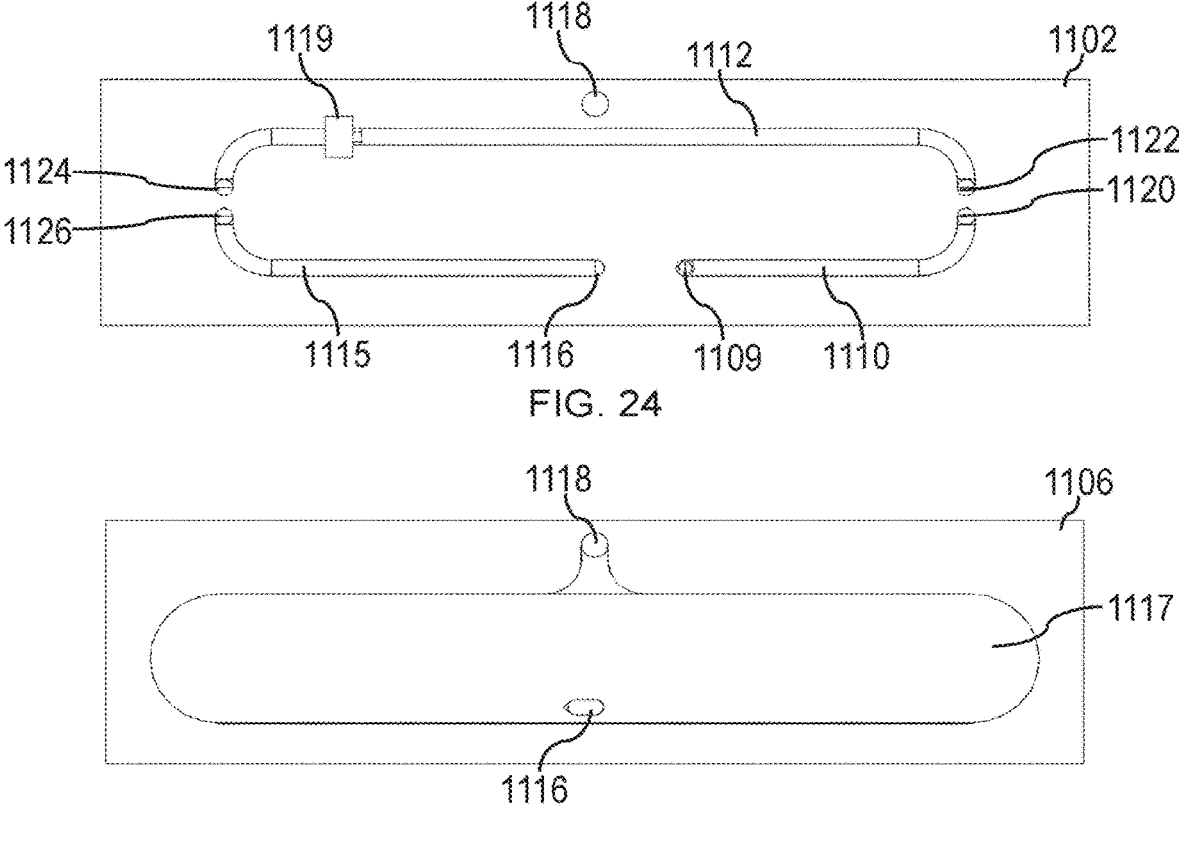
FIG. 24 is a top cross-sectional view of the transfer engine of FIG. 22 taken along line 24-24.
FIG. 25 is a top cross-sectional view of the transfer engine of FIG. 22 taken along line 25-25.
Figure 26:
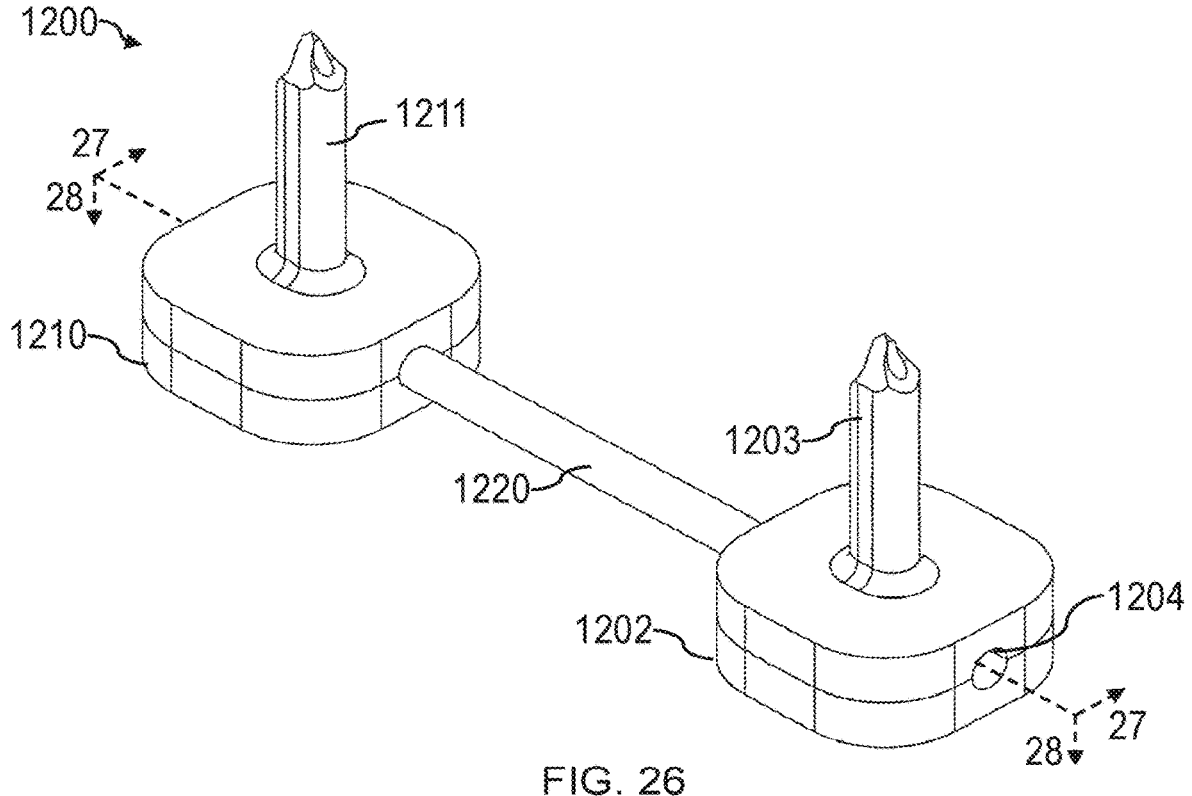
FIG. 26 is a perspective view of another embodiment of a transfer engine.

FIG. 24 is a top cross-sectional view of the transfer engine of FIG. 22 taken along line 24-24, and FIG. 25 is a top cross-sectional view of the transfer engine of FIG. 22 taken along line 25-25. As shown in FIG. 24, the fluid paths are arranged in a circuit-like configuration similar to embodiments previously discussed herein. That is, the first fluid path 1110 and third fluid path 1115 are disposed in a mirrored parallel arrangement to the second fluid path 1112. However, instead of the outlet 1118 being disposed adjacent the inlet 1109, the outlet 1118 is disposed on an opposite side of the transfer engine across from the filter inlet 1116. As shown in FIG. 24, the first fluid path 1110 extends into the first lumen 1120. The second fluid path 1112 extends from a second lumen 1122 and into a third lumen 1124. The third fluid path 1115 extends from the fourth lumen 1126 to the filter inlet 1116. FIG. 25 shows the filter chamber 1117 extending in a racetrack or squared rectangle shape. The filter chamber is configured to receive and retain a planar filter (e.g., a 1 micron filter) that filters fluid passing through the filter chamber. According to the embodiment of FIG. 25, the outlet 1118 is configured so that fluid flows down from the filter inlet 1116 before being drawn back up through the outlet to be delivered to a patient. Such an arrangement ensures the fluid passes through the filter before being delivered. FIG. 26 is a perspective view of another embodiment of a transfer engine 1200. As shown in FIG. 26, the transfer engine includes two spike housings separated by a tube. That is, a first spike housing 1202 includes a first spike 1203 and an inlet 1204. A second spike housing 1210 includes a second spike 1211. Connecting the spike housings is a tube 1220. The tube 1220 may be flexible or rigid. Such an arrangement allows the center-to-center spacing of the spikes 1203, 1211 to be varied for a variety of container sizes using the same spike housings. That is, the tube 1220 may be swapped to have a variety of different length to fit into differently sized embodiments of a reconstitution device.

Figure 27:
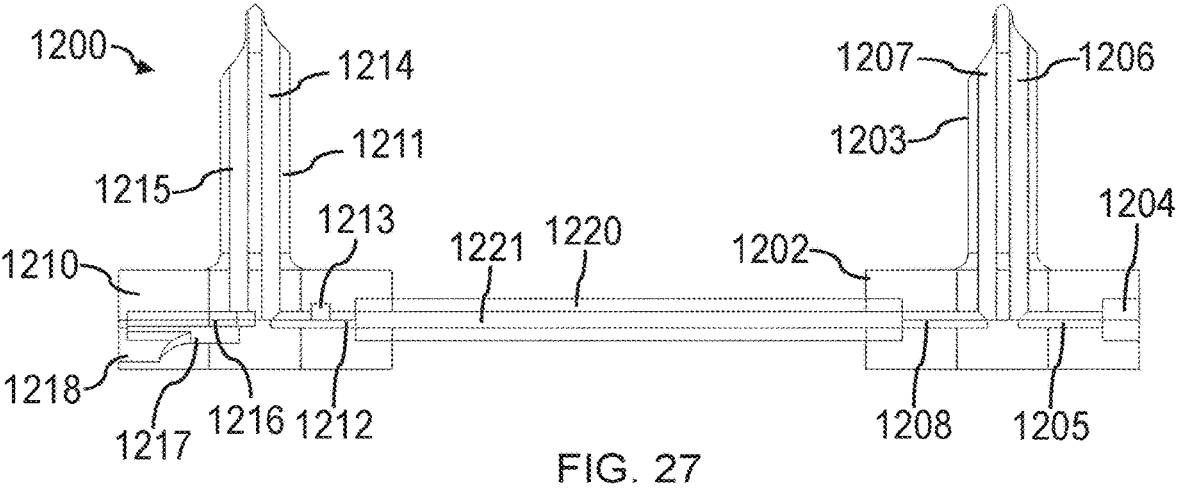
FIG. 27 is a side cross-sectional view of the transfer engine of FIG. 26 taken along line 27-27.
Figure 28:
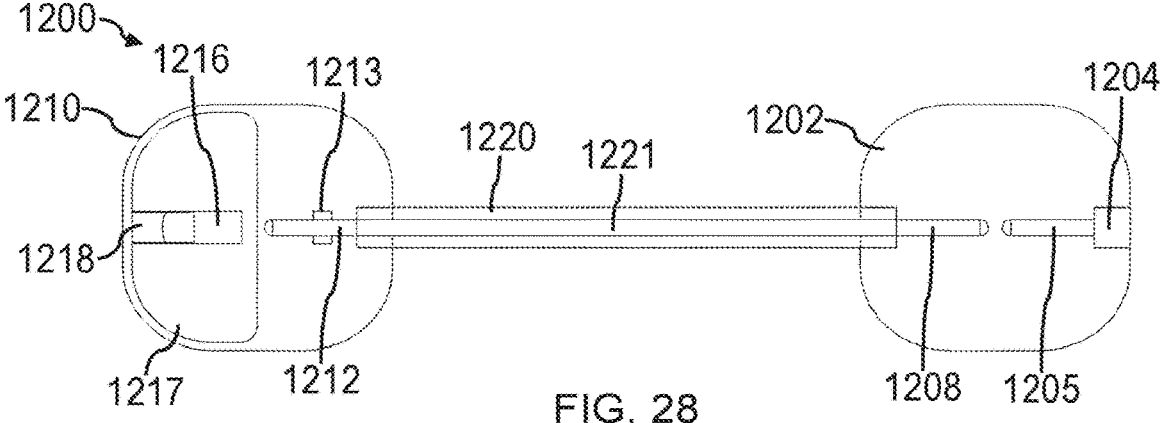
FIG. 28 is a top cross-sectional view of the transfer engine of FIG. 26 taken along line 28-28.

FIG. 27 is a side cross-sectional view of the transfer engine 1200 of FIG. 26 taken along line 27-27, and FIG. 28 is a top cross-sectional view of the transfer engine taken along line 28-28. As shown in FIGS. 27-28, the transfer engine 1200 has a linear layout. The first spike housing 1202 includes an inlet connected to a first fluid path 1205. The first fluid path extends from the inlet to a first lumen 1206 disposed in the first spike 1203. In some embodiments, the air inlet 1204 may include a hydrophobic filter to prevent loss of fluid from the transfer engine while allowing air to enter the transfer engine. The first spike housing also includes a second fluid path 1208 connected to a second lumen 1207 disposed in the first spike. The second fluid path is connected to the tube 1220, and in particular a tube fluid path 1221. The second spike housing 1210 includes a third fluid path 1212 that is connected to the tube fluid path 1221 and extends to a third lumen 1214 disposed in the second spike 1211. Accordingly, the second fluid path 1208, tube fluid path 1221, and third fluid path 1212 form a continuous fluid path from the second lumen 1207 to the third lumen 1214. A check valve 1213 is disposed in the third fluid path 1212 and allows one-way flow from the second lumen 1207 to the third lumen 1214. The second spike housing also includes a fourth lumen 1215 disposed in the second spike 1211. A fourth fluid path 1216 extends between the fourth lumen 1215 and a filter chamber 1217. The filter chamber is in turn connected to an outlet 1218 where fluid may be withdrawn from the transfer engine. A filter may be disposed in the filter chamber to filter fluid being withdrawn from the transfer engine.

Figure 29:
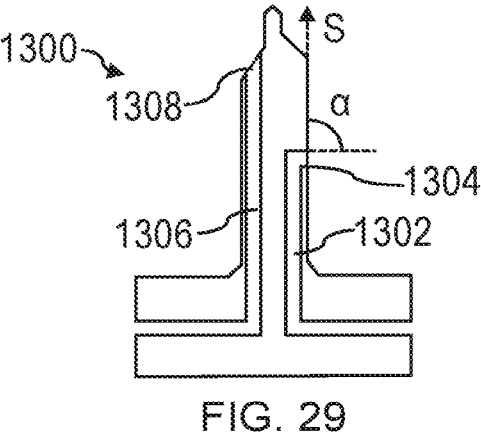
FIG. 29 is a cross-sectional schematic of an embodiment of a spike.

FIG. 29 is a cross-sectional schematic of an embodiment of a spike 1300. As shown in FIG. 29, the spike includes a first fluid path 1302 that terminates in a first open end 1304. According to the embodiment of FIG. 29, the first open end is angled relative to a spike insertion direction S by an angle α. In particular, the first open end is perpendicular to the spike piercing or insertion direction and a is equal to 90 degrees. Accordingly, if fluid exits the first open end 1304 at speed, the fluid may create a vortex in a container to facilitate mixing of a reconstituting fluid and medicament. As show in FIG. 29 the spike includes a second fluid path 1306 terminating in a second open end 1308. In contrast to the first open end, the second open end is parallel to a spike insertion direction. Of course, in other embodiments, the first and second open end may be symmetrical or have any combination of angles relative to a spike insertion direction, as the present disclosure is not so limited.

Figure 30:
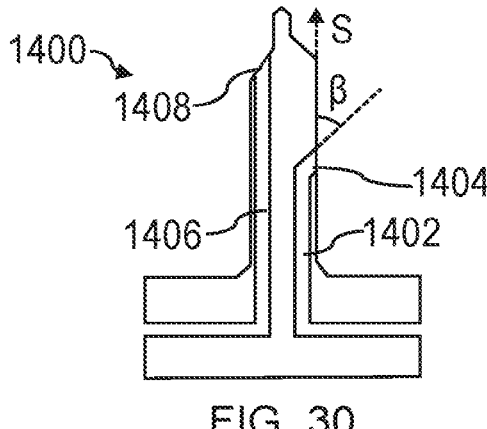
FIG. 30 is a cross-sectional schematic of another embodiment of a spike.

FIG. 30 is a cross-sectional schematic of another embodiment of a spike 1400. As shown in FIG. 30, the spike includes a first fluid path 1402 that terminates in a first open end 1404. According to the embodiment of FIG. 30, the first open end is angled relative to a spike insertion direction S by an angle β. In particular, the first open end is inclined relative to the spike insertion direction at a non-perpendicular angle β, which is equal to approximately 45 degrees. Accordingly, if fluid exits the first open end 1404 at speed, the fluid may create a vortex in a container to facilitate mixing of a reconstituting fluid and medicament. As shown in FIG. 30, the spike includes a second fluid path 1406 terminating in a second open end 1408. In contrast to the first open end, the second open end is parallel to a spike insertion direction. Of course, in other embodiments the first open end or second open end may be inclined relative to the spike insertion direction by any suitable angle. In some embodiments, the angle of an open end relative to the spike insertion direction may be 15 degrees, 30 degrees, 60 degrees, 75 degrees, or any other angle between 1 and 90 degrees.

Figure 31:
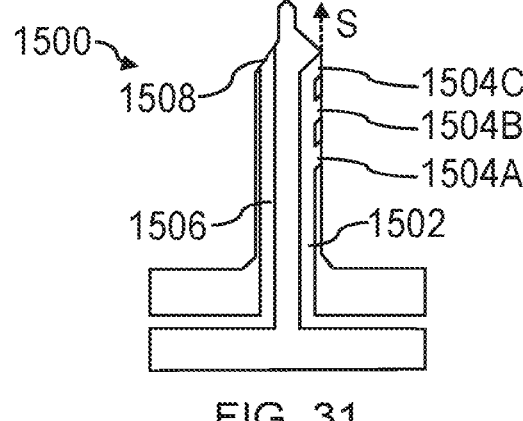
FIG. 31 is a cross-sectional schematic of another embodiment of a spike.

FIG. 31 is a cross-sectional schematic of another embodiment of a spike 1500. As shown in FIG. 31, the spike includes a first fluid path 1502 that terminates in a plurality of first open ends 1504A, 1504B, 1504C. According to the embodiment of FIG. 31, the first open ends are angled relative to a spike insertion direction S. The arrangement of the first fluid path with a plurality of open ends may alter the flow characteristics of fluid passing through the first fluid path at speed. For example, the multiple open ends may reduce the overall force and speed of fluid exiting the first fluid flow path relative to an arrangement having a single first open end. As show in FIG. 31 the spike includes a second fluid path 1506 terminating in a second open end 1508. In contrast to the first open ends, the second open end is parallel to a spike insertion or piercing direction.

In some embodiments, a reconstitution device may include a fluid outlet that is releasably retained in a housing of the reconstitution device until a delivery device is coupled. FIGS. 32A-32D depict schematics of another embodiment of one such reconstitution device 1600. As shown in FIGS. 32A-32D, the reconstitution device includes a housing with an upper portion 1602 and a lower portion 1604. The upper portion is movable (e.g., slidable) relative to the lower portion, where the upper portion moves toward the lower portion from an unactuated position to an actuated position. The upper portion 1602 of the housing includes a cutout 1606 which is configured to selectively provide physical access to a fluid outlet 1610 disposed inside of the reconstitution device housing. That is, the fluid outlet 1610 is physically inaccessible when the housing is in the unactuated position, but is physically accessible through the cutout 1606 when the reconstitution device is actuated. The fluid outlet 1610 is releasably retained inside of the reconstitution device housing by retainers 1608 which are configured to abut projections 1612 disposed on the fluid outlet 1610. The retainers and projections are arranged such that the coupling of a delivery device (e.g., a syringe) to the fluid outlet 1610 releases the fluid outlet from the reconstitution device housing. The fluid outlet may then be removed from the housing and moved, as the fluid outlet 1610 is connected to a transfer engine of the reconstitution device by flexible tubing 1616.

In the state shown in FIG. 32A, the reconstitution device is in an unactuated state. That is, the upper portion 1602 has not been moved toward the lower portion 1604. Accordingly, the cutout 1606 is not aligned with the fluid outlet 1610, such that the fluid outlet 1610 is not physically accessible to a user. According to the embodiment of FIG. 32A, the fluid outlet is retained entirely within the housing when the device is unactuated, although other configurations are contemplated. For example, the fluid outlet may be partially disposed in the housing and blocked until the reconstitution device is actuated. In some embodiments, a fluid outlet may be visible to a user prior to actuation of a reconstitution device, but may be at least partially obstructed so that the fluid outlet may not be physically accessed. The fluid outlet 1610 is shown shaded in dashed diagonal lines for clarity in FIG. 32A.

In the state shown in FIG. 32B, the reconstitution device has been actuated. That is, the upper portion 1602 of the housing has been moved toward the lower portion 1604 of the housing. As discussed with reference to other exemplary embodiments described herein, actuation of the reconstitution device may pierce fluid containers within the reconstitution device housing. As shown in FIG. 32B, the cutout 1606 is aligned with the fluid outlet 1610, such that the fluid outlet 1610 is physically accessible by a user outside of the reconstitution device housing. As shown in FIG. 32B, the projections 1612 of the fluid outlet 1610 are disposed inside of the retainers 1608 (i.e., on an interior side of the retainers relative to the reconstitution device housing). Accordingly, though the fluid outlet 1610 is physically accessible, the retainers 1608 releasably retain the fluid outlet inside of the reconstitution device housing. Additionally, the retainers 1608 may provide frictional resistance against rotation of the fluid outlet 1610 inside of the reconstitution device housing.

In the embodiment of FIG. 32B, the retainers and fluid outlet are configured so that fully coupling a delivery device to the fluid outlet releases the fluid outlet from the reconstitution device housing. That is, in some embodiments, the fluid outlet may be retained in the reconstitution device housing until a suitable delivery device is fully coupled to the reconstitution device. In the embodiment of FIG. 32B, the retainers are configured to allow rotational force to be applied to the fluid outlet 1610 by the delivery device to release the projections 1612 from the retainers, as will be discussed further with reference to FIG. 32C. According to the embodiment of FIG. 32B, the cutout 1606 may be sized and shaped such that the upper portion 1602 of the housing may impede a user from physically accessing the fluid outlet 1610 with something other than an appropriate delivery device. For example, the cutout may be sized and shaped so that multiple fingers may not be inserted through the cutout to grasp the fluid outlet 1610, but a delivery device like a syringe can be inserted through the cutout to interface with the fluid outlet. In this manner, the cutout 1606 may promote proper use of a delivery device to couple the fluid outlet to the delivery device.

In the state shown in FIG. 32C, a delivery device (e.g., syringe) 1614 has been coupled to the fluid outlet 1610 disposed inside of the reconstitution device. In the embodiment of FIGS. 32A-32D, the fluid outlet 1610 includes external thread and is configured as a luer activated device. Accordingly, the delivery device 1614 includes corresponding threads configured to engage the threads of the fluid outlet. When the reconstitution device is in the state shown in FIG. 32B, the delivery device 1614 may be threadedly coupled to the fluid outlet (e.g., by rotating the delivery device clockwise) while the retainers 1608 provide frictional resistance to maintain the rotational position of the fluid outlet. As the delivery device is threadedly coupled, the fluid outlet 1610 may be retained within the reconstitution device housing until the delivery device is fully coupled to the fluid outlet. Once the delivery device is fully coupled, further rotation of the delivery device may overcome the frictional resistance of the retainers 1608 and rotate the fluid outlet 1610 to the state shown in FIG. 32C, where the projections 1612 are no longer aligned with the retainers 1608. This rotation of the fluid outlet may provide an indication to the user that the delivery device has been fully coupled to the fluid outlet, and that the fluid outlet is releasable from the reconstitution device housing.

As shown in FIG. 32D, the fluid outlet 1610 has been released from the reconstitution device housing and has been removed via the cutout 1606. As noted previously, the projections 1612 may clear the retainers 1608 once the delivery device 1614 is threadedly coupled to the fluid outlet 1610. Accordingly, pulling on the delivery device 1614 may remove the fluid outlet 1610 via the cutout 1606. As shown in FIG. 32D, the fluid outlet is connected to the reconstitution device via flexible tubing 1616, so that the fluid outlet 1610 may be moved to a desired position. When the fluid outlet 1610 is removed from the reconstitution device housing, the flexible tubing 1616 may extend or uncoil from inside of the reconstitution device housing.

While one embodiment of a reconstitution device housing including a fluid outlet releasably retained in the housing until a delivery device is coupled is described with reference to FIGS. 32A-32D, other configurations are contemplated and the present disclosure is not so limited in this regard. For example, in some embodiments, a fluid outlet may be coupled to a reconstitution device housing with a frangible connection that is breakable by coupling the delivery device to the fluid outlet. In some embodiments, coupling a delivery device to a fluid outlet may release a latch retaining the fluid outlet in the reconstitution device housing. In some embodiments, a fluid outlet may have a friction fit with the reconstitution device housing, where coupling the delivery device to the fluid outlet overcomes the friction fit. Any suitable motion or combinations of motions of a delivery device may be employed by a user to release a fluid outlet from a reconstitution device housing, including pushing, pulling, rotating and twisting.

Figure 33:
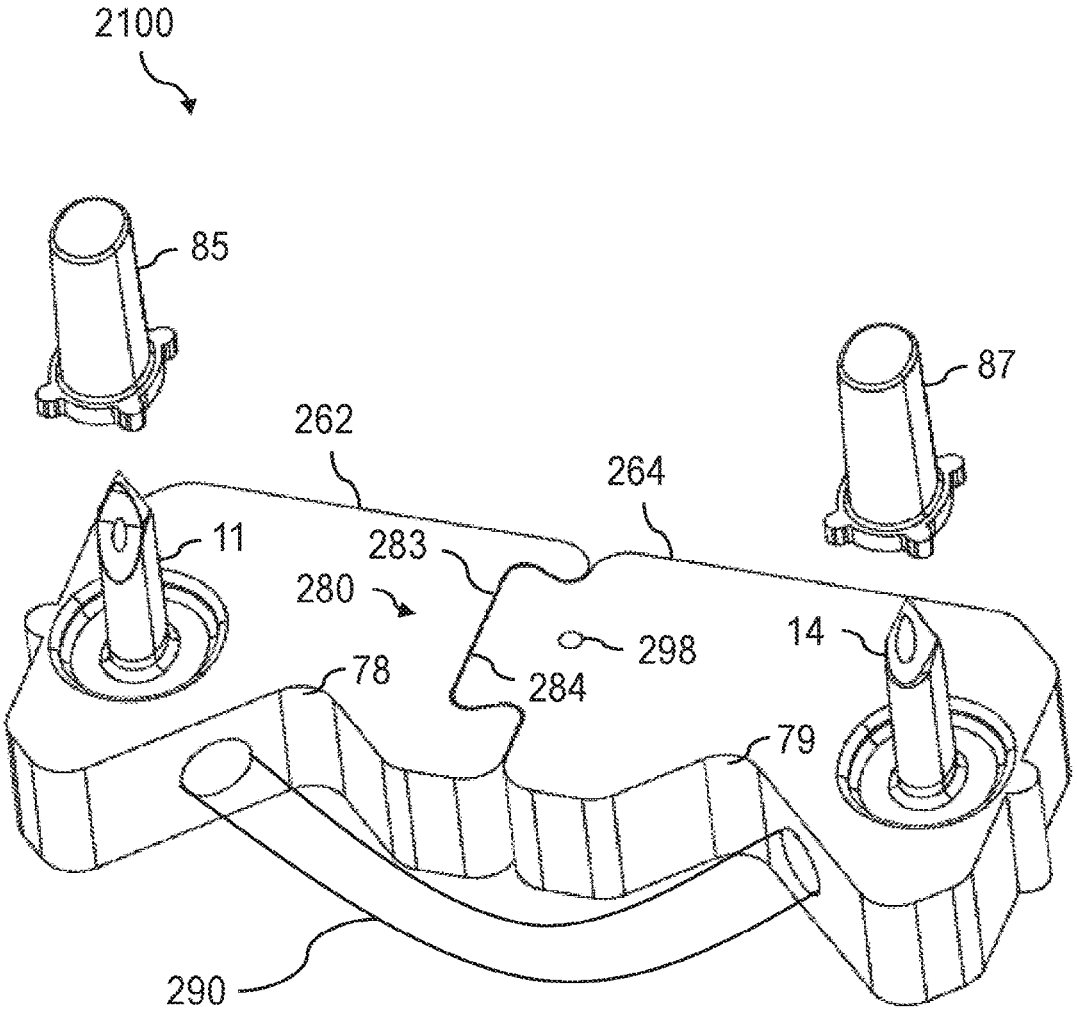
FIG. 33 is a top perspective view of another embodiment of a transfer engine.
Figures 34, 35:
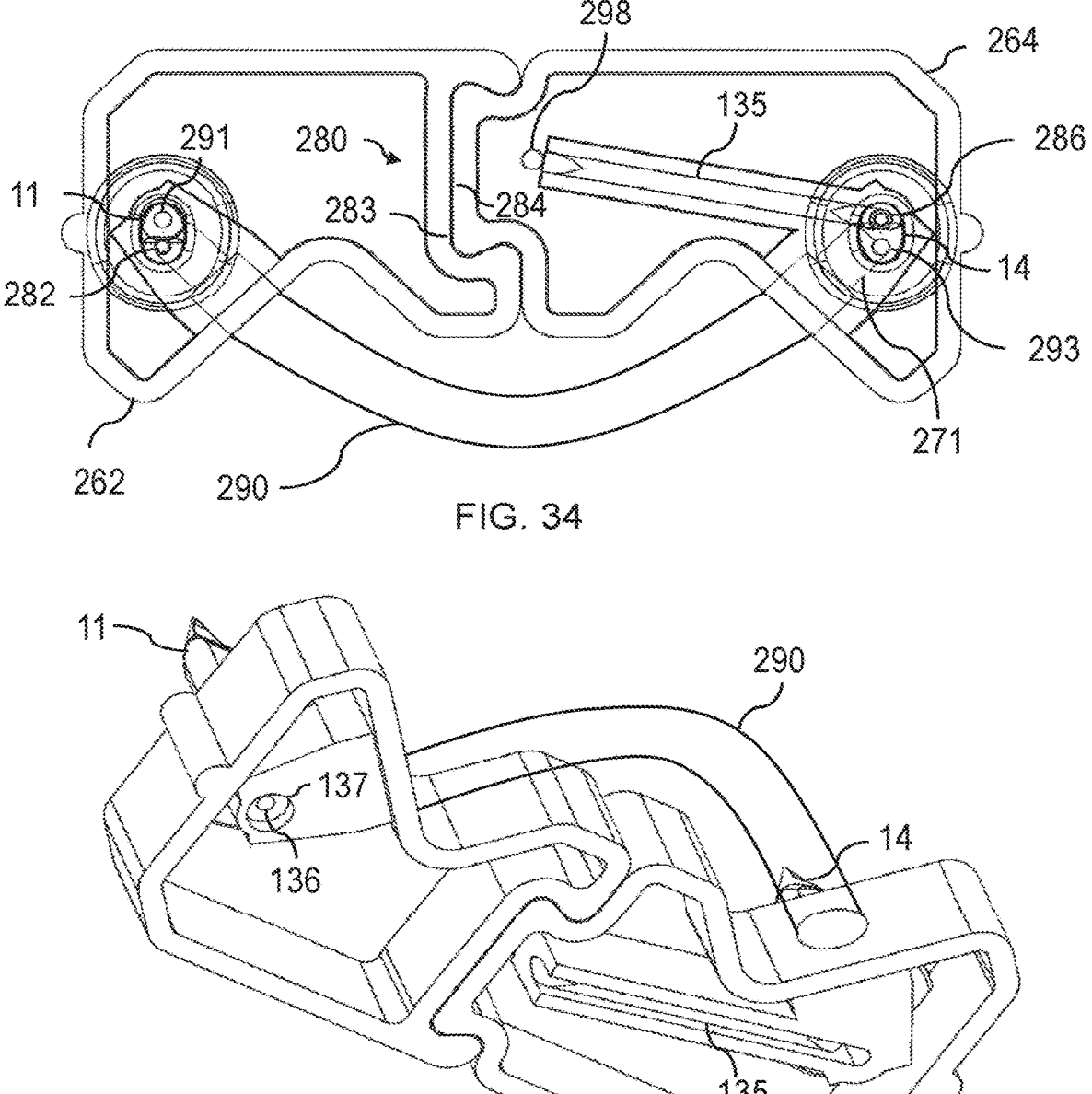
FIG. 34 is a top down view of the transfer engine of FIG. 33.
FIG. 35 is a bottom perspective view of the transfer engine of FIG. 33.

Another illustrative embodiment of a transfer engine 2100 is shown in FIGS. 33-35. As shown in FIG. 33, the transfer engine includes a first spike 11 and a second spike 14. As shown in FIG. 35, the transfer engine includes an inlet 136 (e.g., air inlet), which may include a hydrophobic filter, in some embodiments. The transfer engine may, in some embodiments, include a filter chamber 137 to receive a hydrophobic filter of the inlet. The inlet 136 is connected to a first fluid path 291 which forms a first lumen through the first spike 11. A second fluid path comprising a second lumen 282, tubing 290 and a third lumen 293 connects the first spike 11 to the second spike 14. The third lumen 293 runs through the second spike 14. Disposed in the second fluid path is a check valve 271 which allows one-way flow from the first spike to the second spike. A third fluid path comprising a fourth lumen 286 running through the second spike 14 and a pathway 135 fluidly connects the second spike 14 to an outlet 298. In some embodiments, tubing may couple to the outlet 298 to direct fluid out to a fluid outlet (e.g., a luer connector or other connector) for administration to a user.

The first spike 11 may be formed as part of, or otherwise attached to, a first plate 262, and the second spike 14 may be formed as part of, or otherwise attached to, a second plate 264. The first and second plates may mate with one another via an interlock 280. In some embodiments, the interlock 280 may be formed by a protrusion 284 on the second plate 264 received within an indentation 283 on the first plate 262. It should be appreciated that the positions of the protrusion and indentation may be reversed. In addition, other interlock shapes may be used, such as multiple protrusions/indentations, other jigsaw shapes, or any other suitable shape.

In the illustrative embodiment of FIGS. 33-35, pathway 135 is a molded channel that may be molded as part of, or otherwise attached to, the second plate 264. However, it should be appreciated that other implementations of pathway 135 are possible. In other embodiments, pathway 135 may be tubing, a hypotube, or any other suitable arrangement, as this aspect is not so limited.

In the illustrative embodiment of FIGS. 33-35, a tubing 290 connects the first spike 11 to the second spike 14. In some embodiments, the plates 262, 264 may include indentations 78, 79, respectively, to accommodate the tubing 290. However, it should be appreciated that, in other embodiments, a molded pathway or any other suitable arrangement may be used to connect the first and second spikes instead of tubing.

As seen in FIG. 33, in some embodiments, the transfer engine may include spike sheaths 85, 87 that cover the spikes 11, 14 prior to actuation of the reconstitution device. As containers are pushed downward onto the spikes during actuation, the spikes may pierce through the spike sheaths and into the containers. In some embodiments, the spike sheaths may aid in preventing entry of foreign substances into the fluid pathways by covering the lumens of the spikes prior to use, and/or help to prevent inadvertent premature piercing of the containers.

The spike sheaths may be made of silicone, plastic, elastomer, or any other suitable material.

As discussed above, in some embodiments, the reconstitution device may be configured such that physical access to a fluid outlet may be obstructed prior to actuation. As also discussed above, in some embodiments, a flexible leash may be coupled to the fluid outlet. User access to the flexible leash may be permitted upon alignment of a cutout on the upper portion of the housing with a fluid outlet receptacle. According to one aspect, in some embodiments, the flexible leash, e.g. a pull tab, may be part of or otherwise attached to a cap that covers the fluid outlet. Pulling on the leash may remove the cap from the fluid outlet to expose the fluid outlet for connection to another component such as a syringe or other delivery device. In some embodiments, the fluid outlet is moveable relative to the housing, such that pulling on the leash may remove the fluid outlet from the housing. In some embodiments, the holding force between the fluid outlet and the housing may be less than the holding force between the cap and the fluid outlet such that pulling on the pull tab first causes the fluid outlet to be removed from the housing, then causes the cap to be removed from the fluid outlet. In other embodiments, however, the fluid outlet is fixed relative to the housing and is not configured to be pulled out of the housing during use.

Figure 36:
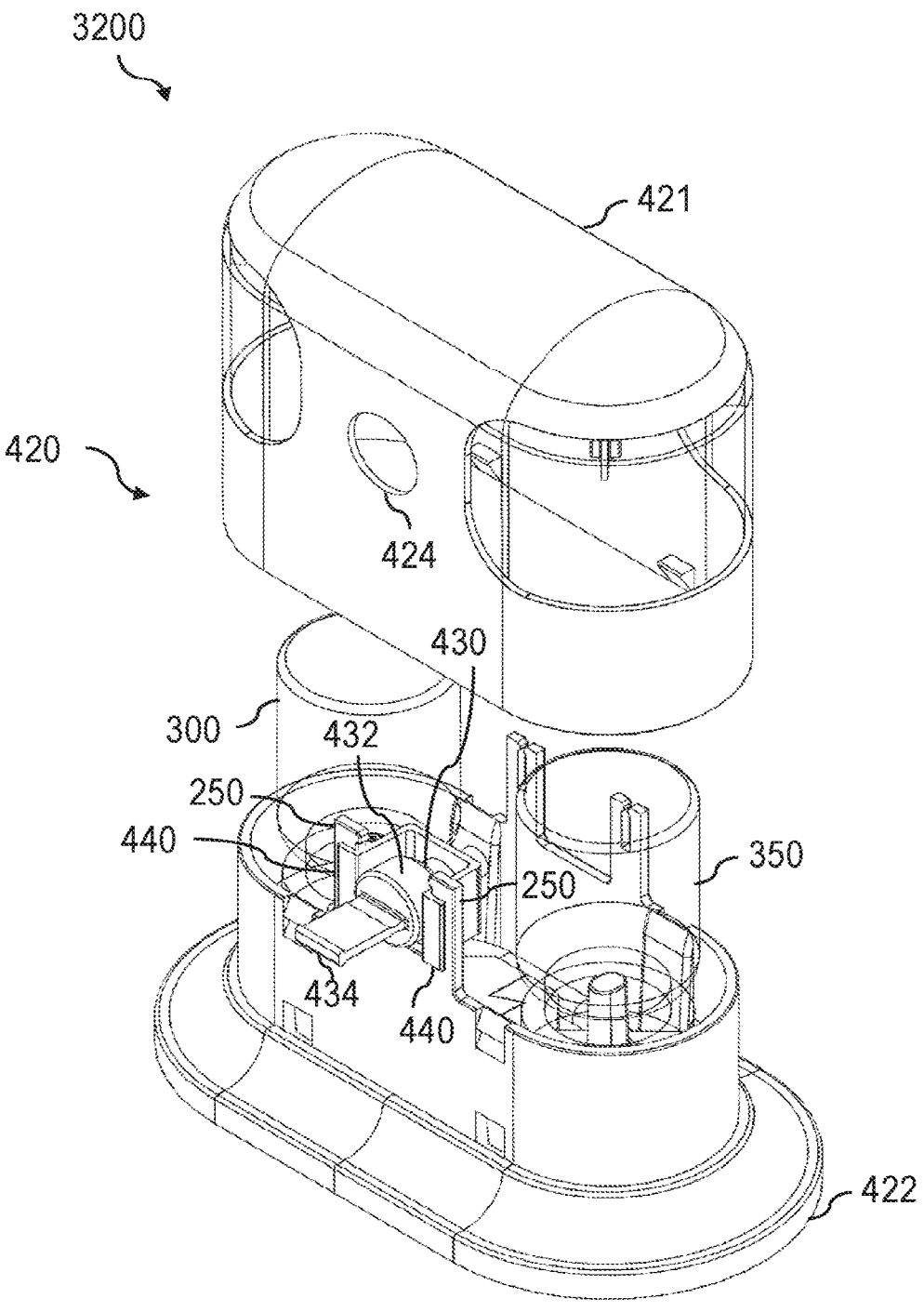
FIG. 36 is an exploded perspective view of another embodiment of a reconstitution device.

One illustrative embodiment of a reconstitution device 3200 is shown in FIG. 36, where the device has a housing 420 having an upper portion 421 and a lower portion 422. The device includes a fluid outlet 430 that is fixed to the lower portion 422 of the housing. In the illustrative embodiment of FIG. 36, the fluid outlet 430 may be formed with or otherwise attached to flanges 440 that may in turn be attached to extensions 250 of the lower portion 422 of the housing. In some embodiments, the additional flanges may be positioned behind the extensions 250 and may attach to the tabs to provide further holding reinforcement. However, it should be appreciated that the fluid outlet may be fixed to the lower portion of the housing by any suitable attachment arrangement, as this aspect is not so limited.

A cap 432 with a pull tab 434 covers the fluid outlet 430. The pull tab 434 may be flexible such that when the upper portion 421 of the housing is in the unactuated state, an interior surface of the upper portion 421 presses against the pull tab 434 such that the pull tab is in a folded or otherwise compressed state. When the upper portion 421 is pushed down, a cutout 424 on the upper portion 421 may move into alignment with the fluid outlet 430 and the cap 432, thus allowing the pull tab 434 to unfold and extend out of the cutout 424 for access by a user.

Figures 37A, 37B, 37C:
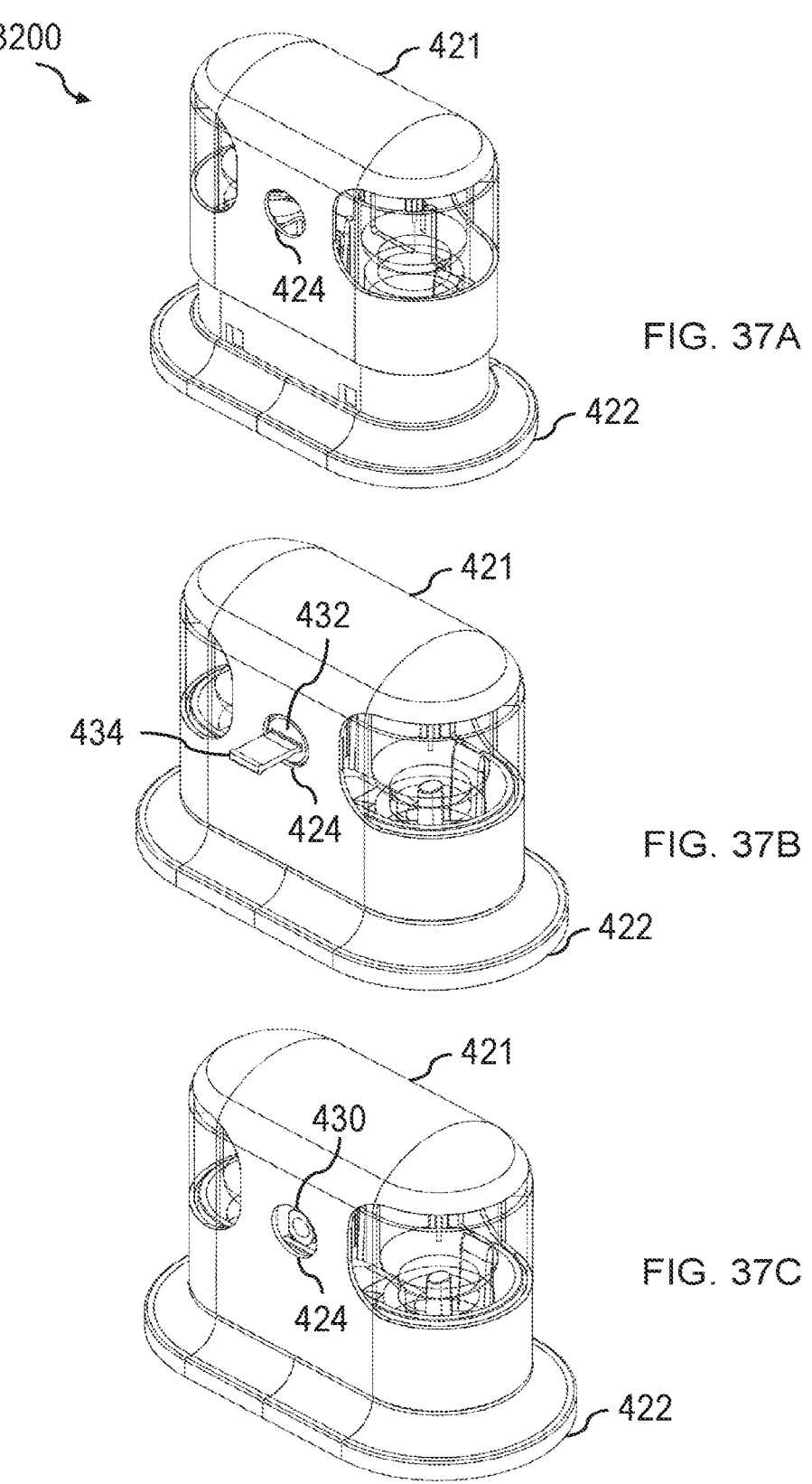
FIG. 37A is the reconstitution device of FIG. 36 in a first state.
FIG. 37B is the reconstitution device of FIG. 37A in a second state.
FIG. 37C is the reconstitution device of FIG. 37A in a third state.

FIGS. 37A-37C depict the various operational stages of the reconstitution device 3200. In FIG. 37A, the device is in the unactuated state. The cutout 424 of the upper portion 421 of the housing is spaced from the fluid outlet, and the pull tab may in be a folded state. e.g., abutting against the inside surface of the upper portion 421. As such, physical access to the pull tab, and to the fluid outlet, is obstructed by the upper portion of the housing. In some embodiments, the pull tab may be hidden from view. In other embodiments, the pull tab may be visible. e.g. if the upper portion is made of a transparent material, but the pull tab may remain inaccessible by a user.

To move the device into the actuated state shown in FIG. 37B, a user may push downward on the upper portion 421 of the housing, causing the upper portion 421 to slide downward toward the lower portion 422 of the housing. Downward movement of the upper portion 421 brings the cutout 424 into alignment with the fluid outlet 430 and the cap 432, allowing the pull tab 434 to unfold and extend out of the cutout 424.

A user may then pull on the pull tab 434 to remove the cap 432, thereby exposing the fluid outlet 430, as shown in FIG. 37C. With the fluid outlet 430 exposed, the user may proceed to attach a syringe or other delivery device to the fluid outlet 430.

Figure 38:
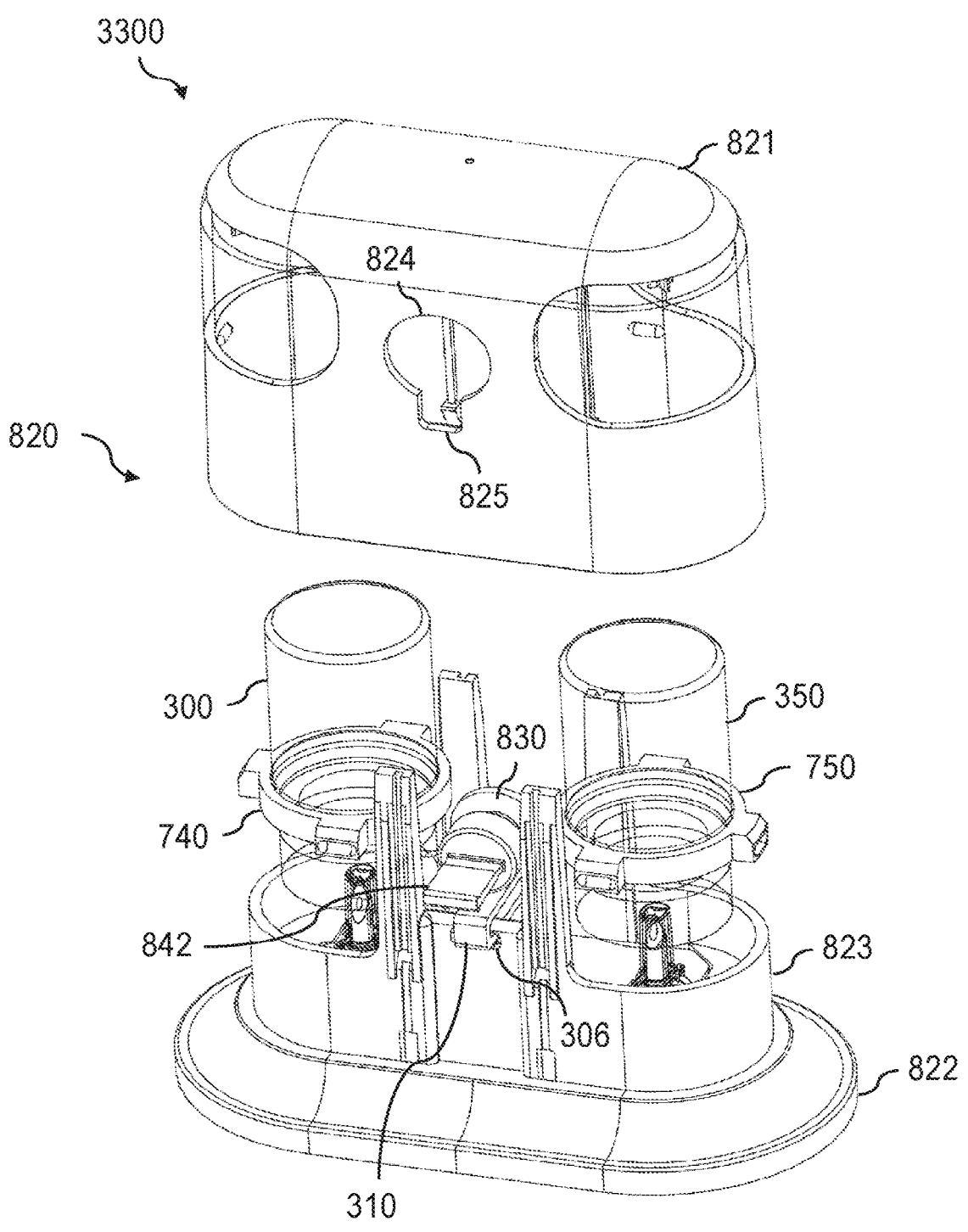
FIG. 38 is an exploded perspective view of another embodiment of a reconstitution device.
Figure 39:
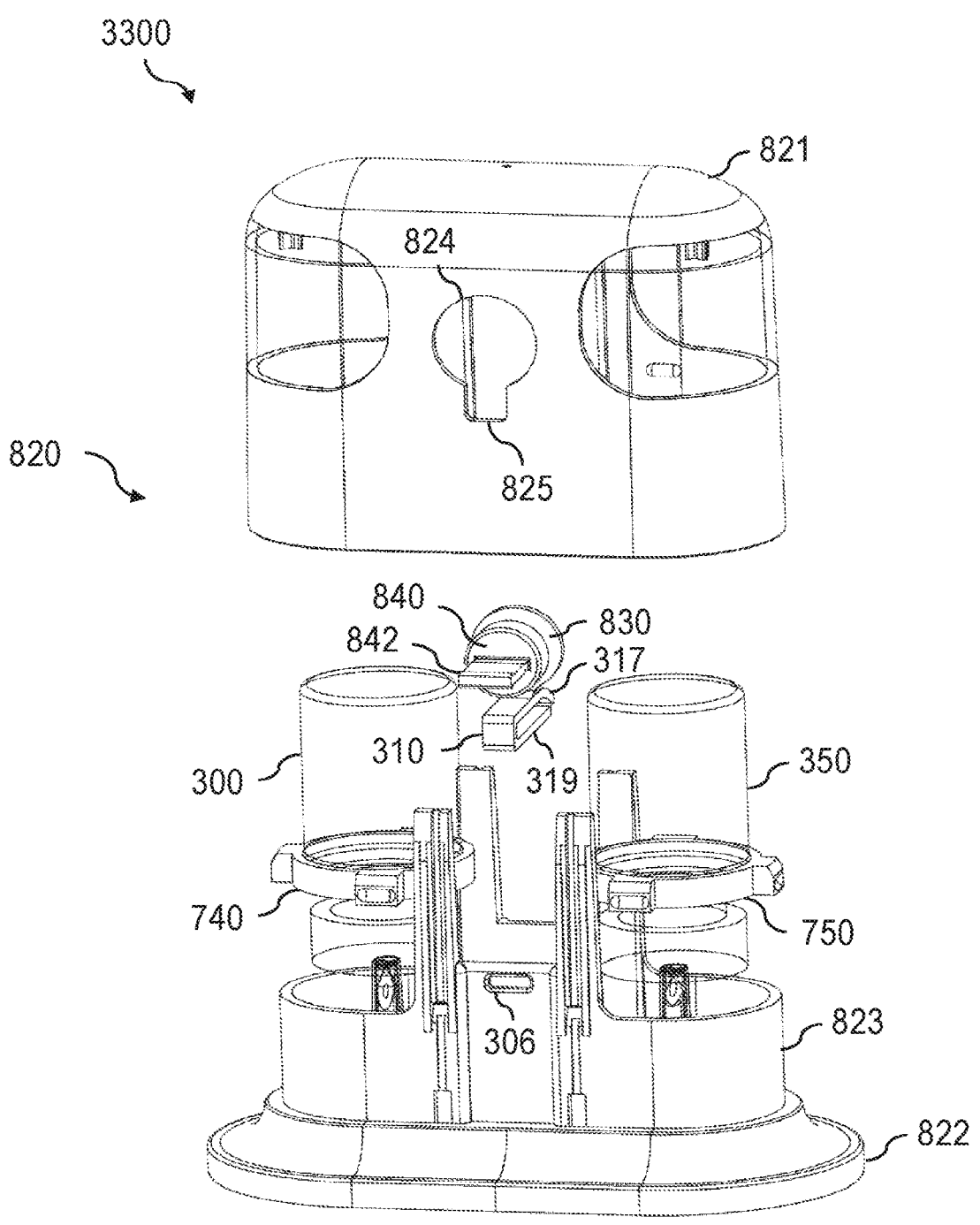
FIG. 39 is another exploded perspective view of the reconstitution device of FIG. 38.

Another illustrative embodiment of a reconstitution device 3300 is shown in FIGS. 38-40D, where the device has a housing 820 having an upper portion 821 and a lower portion 822. The device includes a fluid outlet 830 that is moveable relative to the lower portion 822 of the housing. As shown in the exploded views of FIGS. 38 and 39, the fluid outlet 830 may be formed with or otherwise attached to a clip 310. The clip 310 may have a first leg 317 and a second leg 319. Prior to actuation, the clip is removably coupled to the lower portion 822 of the housing. After actuation, a user may decouple the clip from the lower housing by pulling the fluid outlet out of the housing. As seen in FIG. 39, an inner guide 823 of the lower portion 822 of the housing may include a slot 306 sized to receive the second leg 319 of the clip 310. The clip is shown fully engaged with the slot 306 in FIG. 38. As shown in FIG. 38, with the 310 fully engaged with the slot 306, the clip 310 and the slot 306 may be positioned vertically underneath the fluid outlet 830. In other embodiments, however, the clip and/or the slot may be positioned at different positions relative to the fluid outlet, such as vertically above, to the left, or to the right of the fluid outlet.

In this illustrative embodiment, a cap 840 with a pull tab 842 may cover the fluid outlet 430 prior to device actuation. When a user pulls the pull tab 842 after the device has been actuated, the second leg 319 slides through and exits the slot 306, thus uncoupling the clip and the fluid outlet 830 from the lower portion 822 of the housing. As such, the pull tab 842 may function as a leash that a user may pull on to remove the fluid outlet from the housing. In some embodiments, the holding force of the cap 840 on the fluid outlet 830 may be greater than the holding force of the clip 310 on the lower portion 822 of the housing. As such, pulling on the pull tab 842 may first cause the clip 310 to exit and separate from the slot 306 prior to the cap 840 separating from the fluid outlet 830.

In some embodiments, a cutout 824 of the upper portion 821 may include an extended opening 825 to accommodate movement of the clip 310 through the cutout.

Figures 40A, 40B, 40C:
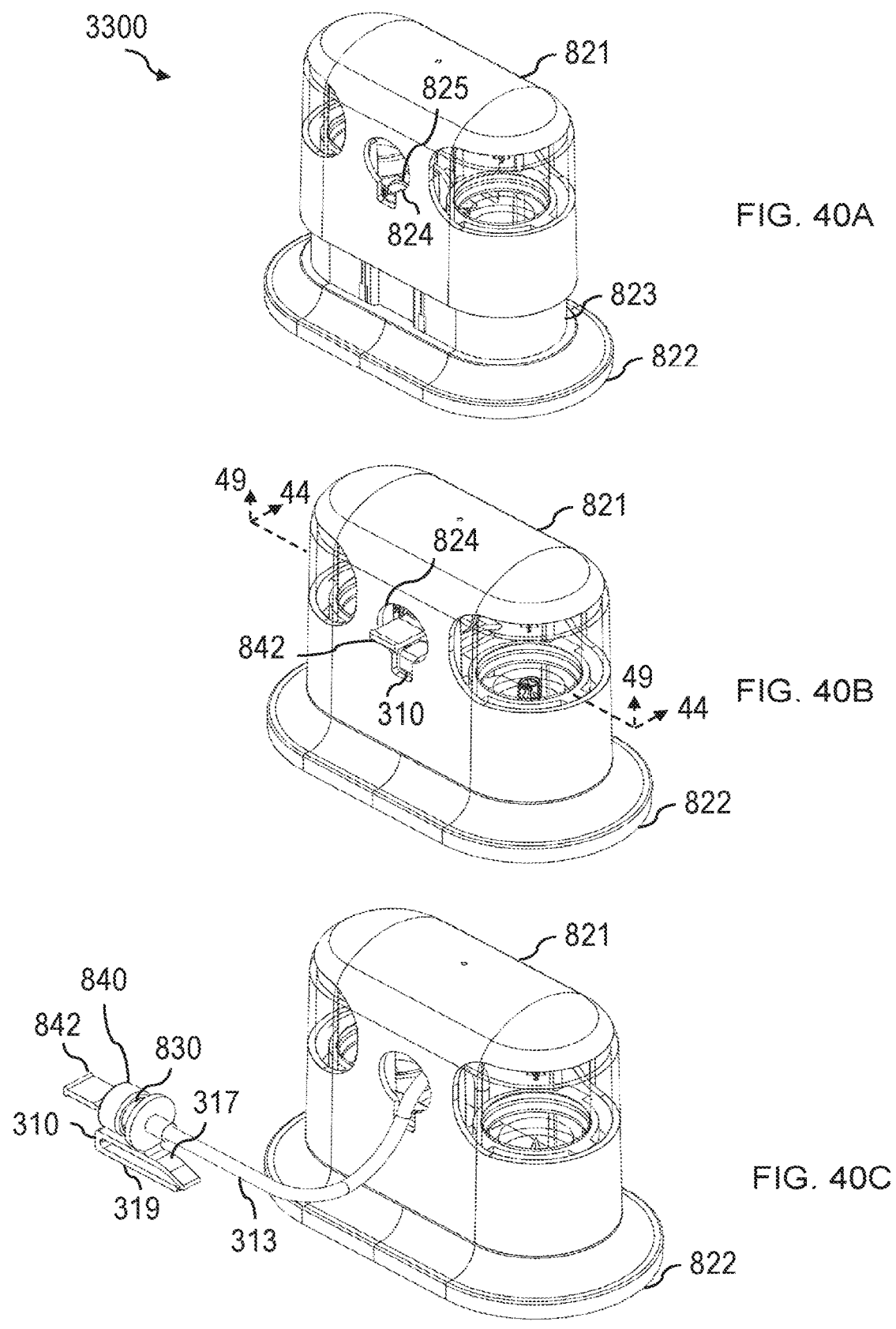
FIG. 40A is the reconstitution device of FIG. 38 in a first state.
FIG. 40B is the reconstitution device of FIG. 40A in a second state.
FIG. 40C is the reconstitution device of FIG. 40A in a third state.

FIGS. 40A-40D depict the various operational stages of the reconstitution device 3300. In FIG. 40A, the device is in the unactuated state. The cutout 824 of the upper portion 821 of the housing is spaced from the fluid outlet 830, and the pull tab may be in a folded state abutting against the inside surface of the upper portion 821. As such, physical access to the pull tab, and to the fluid outlet, may be obstructed by the upper portion of the housing.

To move the device into the actuated state shown in FIG. 40B, a user may push downward on the upper portion 821 of the housing, causing the upper portion 821 to slide downward toward the lower portion 822 of the housing. Downward movement of the upper portion 821 brings the cutout 824 into alignment with the fluid outlet and the cap 840, allowing the pull tab 842 to unfold and extend out of the cutout 824.

Figure 40D:
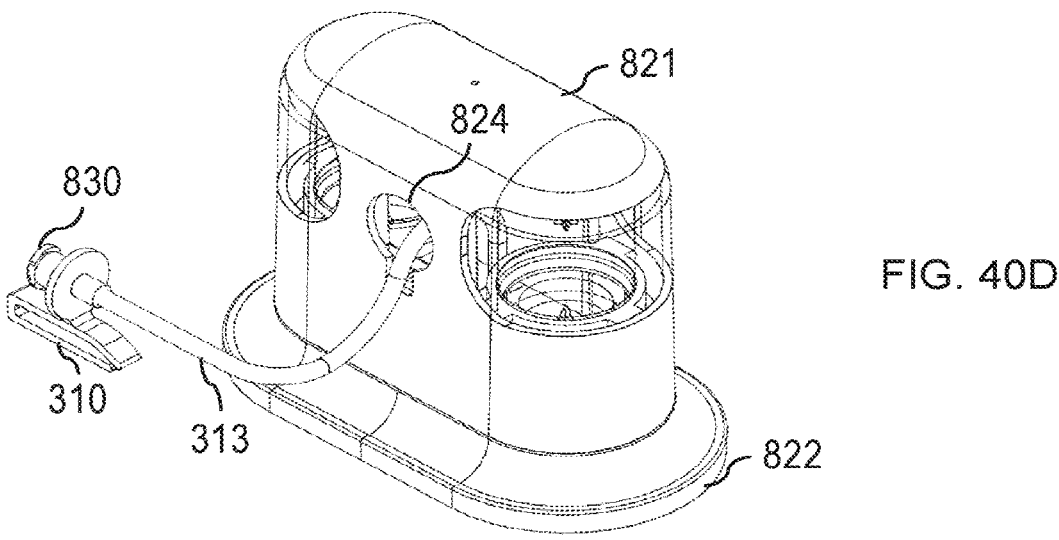
FIG. 40D is the reconstitution device of FIG. 40A in a fourth state.

A user may then pull on the pull tab 842. With the holding force of the cap 840 on the fluid outlet being greater than the holding force of the clip 310 on the lower portion 822 of the housing, pulling on the pull tab 842 causes the clip to exit the slot 306 of the lower portion 822 of the housing. As a result, as shown in FIG. 40C, the cap 840, and the fluid outlet 830, which is attached to the cap, may both be pulled out of the housing as a user pulls on the pull tab 842. After the fluid outlet 830 has been uncoupled from the lower portion 822 of the housing, a user may continue to pull on the pull tab 842 to remove the cap 840 from the fluid outlet 830, thereby exposing the fluid outlet 830, as shown in FIG. 40D. In some embodiments, a user may pull on the pull tab 842 with one hand while holding onto a portion of the fluid outlet 830, clip 310, and/or tubing 313 with the other hand in order to pull the cap 840 off of the fluid outlet 830.

Figure 41:
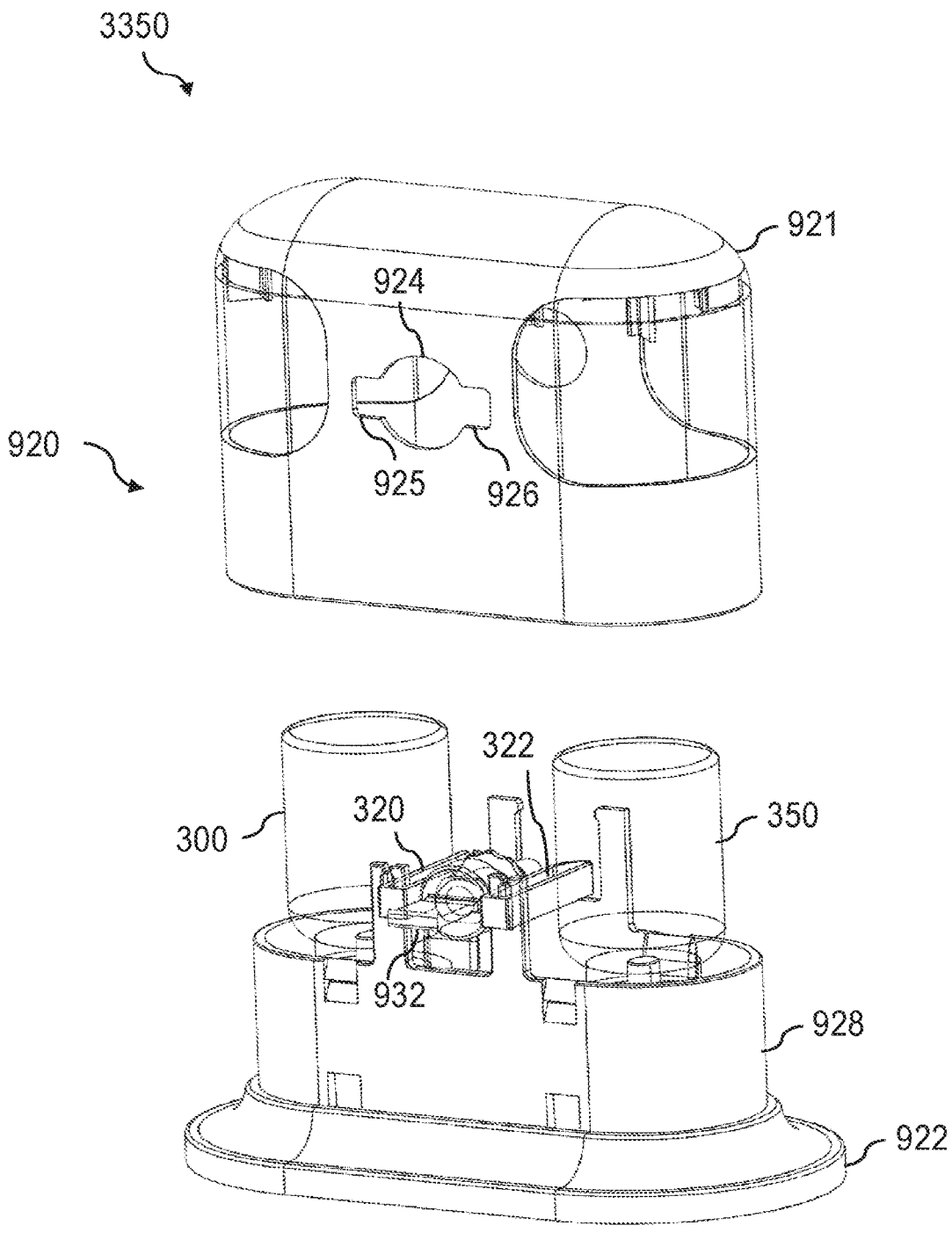
FIG. 41 is an exploded perspective view of another embodiment of a reconstitution device.
Figure 42:
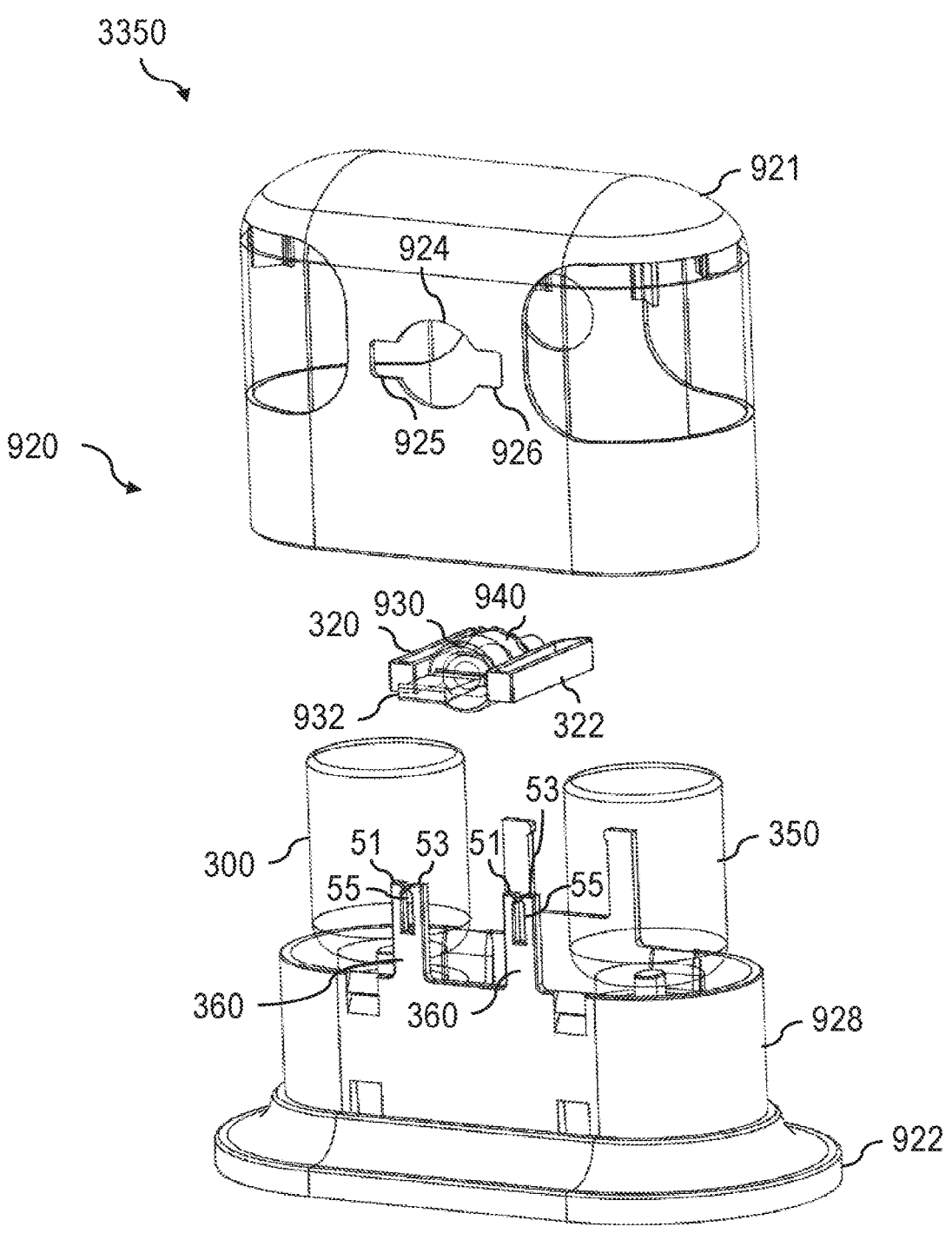
FIG. 42 is another exploded perspective view of the reconstitution device of FIG. 41.

Another illustrative embodiment of a reconstitution device 3350 is shown in FIGS. 41-43C, where the device has a housing 920 having an upper portion 921 and a lower portion 922. Similar to the illustrative embodiment of FIG. 38, the reconstitution device 3300 includes a fluid outlet 940 that is moveable relative to the lower portion 922 of the housing. In this embodiment, however, as shown in FIGS. 41 and 42, the fluid outlet 940 is formed with or otherwise attached to two clips, a first clip 320 and a second clip 322. Prior to actuation, the first clip 320 and the second clip 322 are removably coupled to the lower portion 922 of the housing. In some embodiments, the inner guide 928 may include two extending tabs 360, each having a slot 55. In some embodiments, the slot may be defined by two opposing arms 51, 53. In other embodiments, the slot may be a through-hole through the tab. Prior to actuation of the reconstitution device, the clips 320, 322 of the fluid outlet 940 may be received within the slots 55 to couple the fluid outlet to the lower portion 922 of the housing. As shown in FIG. 41, with the clips 320, 322 received within the slots 55, the slots 55 and the clips 320, 322 may flank the left and right sides of the fluid outlet. In other embodiments, however, the clips and/or the slots may be positioned at different positions relative to the fluid outlet, such as vertically above and below the fluid outlet.

In some embodiments, the cutout 924 may include extended openings 925, 926 to accommodate movement of the clips through the cutout.

In this illustrative embodiment, a cap 930 with a pull tab 932 may cover the fluid outlet 940 prior to device actuation. When a user pulls the pull tab 932 after the device has been actuated, the clips 320, 322 slide through and exit the slots 55, thus uncoupling the clips and the fluid outlet 940 from the lower portion 922 of the housing. As such, the pull tab 932 may function as a leash that a user may pull on to remove the fluid outlet from the housing. In some embodiments, the holding force of the cap 930 on the fluid outlet 940 may be greater than the holding force of the clips 320, 322 on the lower portion 822 of the housing. As such, pulling on the pull tab 932 may first cause the clips 320, 322 to exit and separate from the slots 55 prior to the cap 930 separating from the fluid outlet 940.

Figures 43A, 43B, 43C:
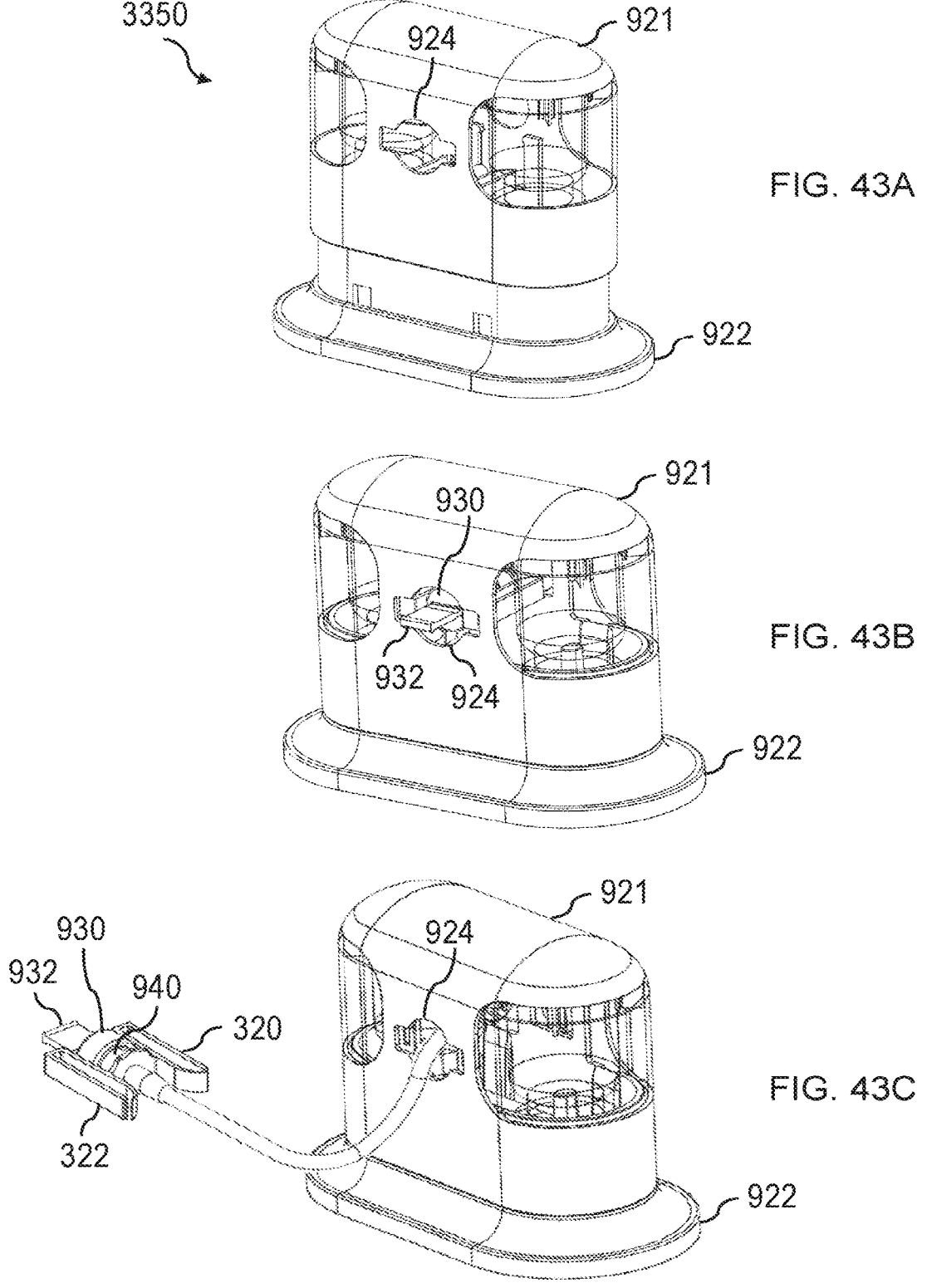
FIG. 43A is the reconstitution device of FIG. 41 in a first state.
FIG. 43B is the reconstitution device of FIG. 43A in a second state.
FIG. 43C is the reconstitution device of FIG. 43A in a third state.

FIGS. 43A-43C depict the various operational stages of the reconstitution device 3350. In FIG. 43A, the device is in the unactuated state. The cutout 924 of the upper portion 921 of the housing is spaced from the fluid outlet 940, and the pull tab may be in a folded state abutting against an inside surface of the upper portion 921. As such, physical access to the pull tab, and to the fluid outlet, may be obstructed by the upper portion 921 of the housing.

To move the device into the actuated state shown in FIG. 43B, a user may push downward on the upper portion 921 of the housing, causing the upper portion 921 to slide downward toward the lower portion 922 of the housing. Downward movement of the upper portion 921 brings the cutout 924 into alignment with the fluid outlet and the cap 930, allowing the pull tab 932 to unfold and extend out of the cutout 924.

A user may then pull on the pull tab 932. With the holding force of the cap 930 on the fluid outlet being greater than the holding force of the clips 320, 322 on the lower portion 922 of the housing, pulling on the pull tab 932 causes the clips to exit the slots 55 of the lower portion 922 of the housing. As a result, as shown in FIG. 43C, the cap 930, and the fluid outlet 940, which is attached to the cap, may both be pulled out of the housing as a user pulls on the pull tab 932. After the fluid outlet 940 has been uncoupled from the lower portion 922 of the housing, a user may continue to pull on the pull tab 932 to remove the cap 930 from the fluid outlet 940, thereby exposing the fluid outlet 940.

While the embodiment of FIG. 38 uses a single clip and the embodiment of FIG. 41 uses two clips, it should be appreciated that any number of clips may be used.

According to one aspect, a reconstitution device may include one or more features that help to retain containers. Such retaining features may help to position the containers, e.g., to help with preventing premature piercing of the containers, and/or to assist with container piercing by facilitating alignment of the containers with spikes during spiking. In some embodiments, the container retaining features may be coupled to a portion of the housing that is moved during actuation. For example, in embodiments in which an upper portion of the housing is pushed downwardly by a user to actuate the reconstitution device, one or more container retaining features may be coupled to the upper portion of the housing.

In some embodiments, a container retention feature includes a ring that surrounds a portion of the container to retain the container. In some embodiments, the ring may be configured to surround a shoulder portion of the container. An internal surface of the ring may be contoured to accommodate the shape of the shoulder portion of the container.

In the illustrative embodiment shown in FIGS. 38-40D and FIGS. 44-48, the reconstitution device includes a first ring 740 that surrounds the first container 300, and a second ring 750 that surrounds the second container 350. As will be discussed in more detail below, the rings may be attached to the upper portion 821 of the housing. By surrounding the containers, the rings may serve to restrict side-to-side movement of the containers.

Figure 44:
FIG. 44 is a cross-sectional view of the reconstitution device of FIG. 40B taken along line 44-44.

In some embodiments, the containers may rest upon a portion of the rings. As seen in FIG. 44, the rings 740, 750 are contoured to accommodate the shape of the shoulder 35 of the containers. For instance, ring 750 has an inner surface 744 that changes in diameter, creating a contoured surface. The inner surface 744 transitions from a first diameter to a second, smaller diameter to accommodate a profile of the shoulder 35 of the container 350. In some embodiments, a cross-section of the inner surface may form an S-shape.

With the shoulder of the container abutting against the contoured inner surface of the ring, the ring may serve to restrict movement of the containers toward the spikes. As the upper portion 821 of the housing is moved toward the lower portion 822 of the housing during device actuation, the rings, which are attached to the upper portion 821 of the housing, move toward the spikes, thus permitting the containers to move toward the spikes for piercing.

In some embodiments, an inner contact may be coupled to an inner surface of the ring. The inner surface of the ring may have a greater rigidity than the inner contact. The inner contact may serve as a finer sizing member that may assist with reducing clearance with a container. The inner contact may be a gasket, molded nubs, radially inwardly extending fingers, or any other suitable contact. For example, in one illustrative embodiment, the inner surface of the ring may include a circumferential groove within which a gasket sits.

It should be appreciated that a container retaining feature may engage with different portions of the container. For example, in some embodiments, the container retaining feature may engage with the body sidewall, the shoulder the neck, the crimp, and/or any other suitable portion of the container.

Figure 45:
FIG. 45 is a perspective cross-sectional view of the reconstitution device of FIG. 44.
Figure 46:
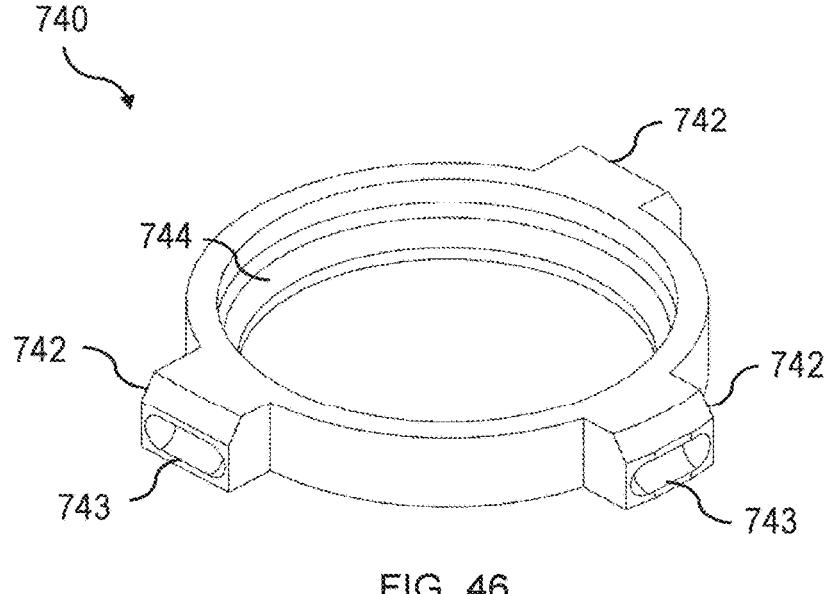
FIG. 46 is a perspective view of a container retainer ring.
Figure 47:
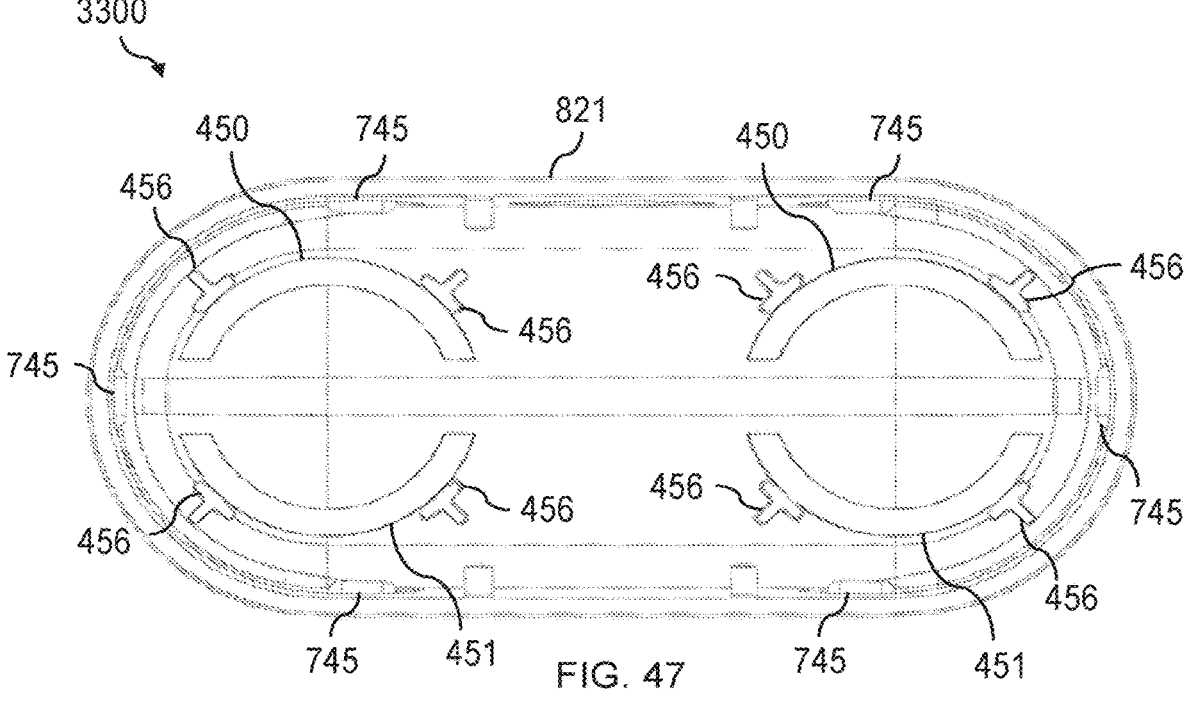
FIG. 47 is a bottom view of an upper portion of the reconstitution device of FIG. 40B.
Figure 48:
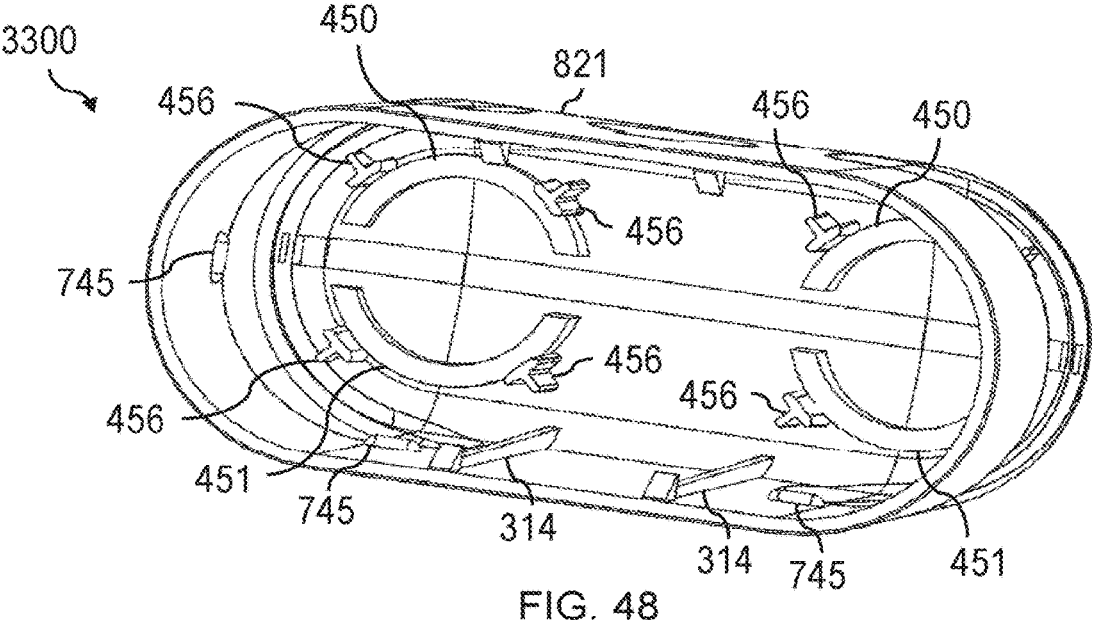
FIG. 48 is a bottom perspective view of the upper portion of FIG. 47.

Attachment of the rings to the housing will now be discussed. As seen in FIG. 46, the ring 740 may include a plurality of radially extending extension portions 742 which may each include a recess 743. As seen in FIGS. 45, 47 and 48, the upper portion 821 of the housing includes a plurality of protrusions 745 shaped to match the shape of the recesses on the rings. In the illustrative embodiment of the figures, the recesses and protrusions are hemi-ellipsoidal. The rings attach to the upper portion of the housing by mating the protrusions of the upper portion 821 with the recesses of the rings. In some embodiments, further holding reinforcement, such as adhesive or fasteners, may be used to reinforce the attachment. In other embodiments, however, the rings are held to the upper portion of the housing simply by snap-fit engagement between the protrusions and the recesses. It should be appreciated that the protrusions and recesses may be reversed such that the recesses are located on the upper portion of the housing, while the protrusions are located on the rings. In addition, while the protrusions and recesses shown in the figures are hemi-ellipsoidal, it should appreciated that they may be hemispherical, rectangular prisms, conical, frustoconical, trapezoidal prisms, or any other suitable shape.

In some embodiments, attachment of the rings to the housing may be achieved via adhesive, fasteners, and/or other attachment arrangements, as an alternative to, or in addition to, the protrusion and recess mating arrangement discussed above.

It should be appreciated that the rings may be omitted from some embodiments. In some embodiments, adhesive, fasteners, or other attachment arrangements may be used to hold the container(s) relative to the housing.

In some embodiments, a container retention feature includes a plurality of arms that at least partially surround a portion of the container to restrict movement of the container.

Figure 49:
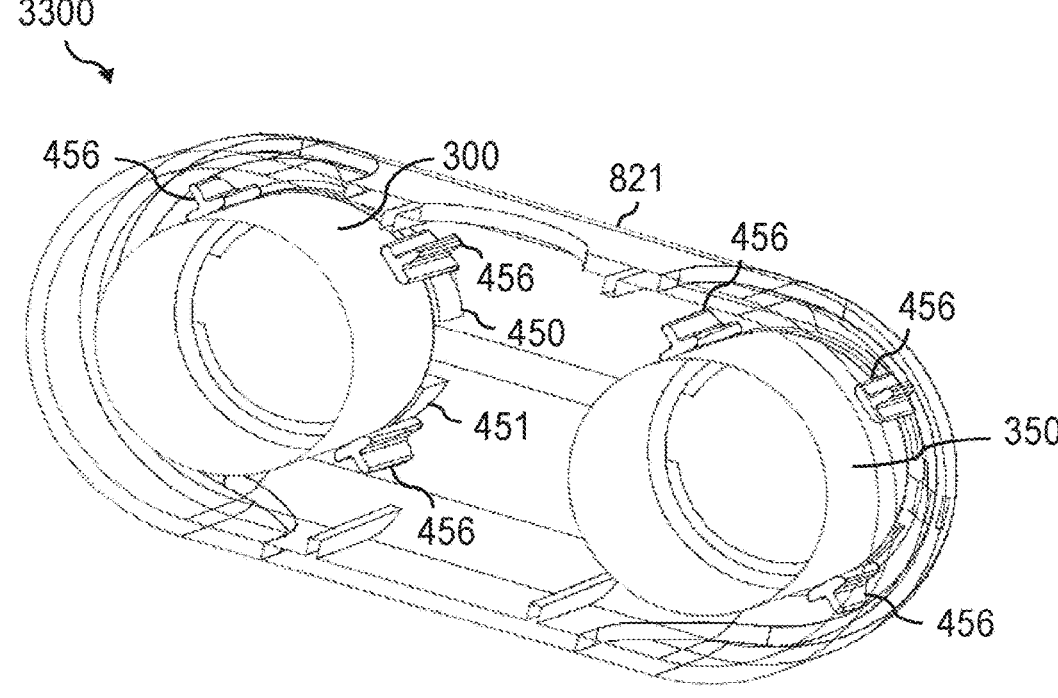
FIG. 49 is a perspective cutaway view of the reconstitution device of FIG. 40B taken along line 49-49.

In the illustrative embodiment shown in FIGS. 47-49, the reconstitution device includes a plurality of arms 456 extending from the upper portion 821 of the housing. As shown in FIG. 49, which is a perspective cross-sectional view showing a portion of the containers 300, 350 received with the upper portion 821 of the housing, the plurality of arms 456 surround the containers 300, 350. The plurality of arms 456 are positioned radially outwardly of the containers and receive a bottom end of the containers.

In some embodiments, the reconstitution device may include a platform that abuts against a bottom end of the containers. The platform may serve to fill a gap between the housing and the container to prevent movement of the container within the housing prior to actuation, e.g. during transport.

In the illustrative embodiment shown in FIGS. 47-48, the reconstitution device includes platforms 450, 451 configured to abut against a bottom end of the containers. In the illustrative embodiment, the platforms are arcuate shaped. However, in other embodiments, the platforms may be circular, oval, square, dome shaped, or any other suitable shape. The platforms may be made of foam, elastomer, silicone, or any other suitable material.

In some embodiments, the reconstitution device may have a modular design that may allow for accommodation of different container sizes with the same housing. For example, the platforms 450, 451 may be interchanged with platforms of other heights and/or radii of curvature to accommodate different container sizes. For instance, shorter containers may still be used with the same housing by using a platform with a greater height. Similarly, the plurality of arms 456 may be interchanged with other arms, e.g. arms positioned at different distances to accommodate containers of different diameters. In some embodiments, the plurality of arms and/or platforms may be pre-molded or otherwise pre-attached to a plate that can be attached to the inside of the upper portion 821 of the housing. Plates having different combinations of arms and/or platforms may be manufactured to accommodate a wide variety of container sizes and shapes. The upper portion of the housing may be configured to attach to any of these plates, thus permitting the housing to have a modular design where the same housing can be used to accommodate different container sizes. In addition, the rings 740, 750 may also be interchanged with rings of different inner diameters to accommodate different container sizes.

As discussed above, in some embodiments, a reconstitution device may include one or more engagement features that permit the upper and lower portions of the housing to slidably engage with one another. In some embodiments, the inner guide may include one or more engagement features that slidably engage with feature(s) on the upper portion. For example, the inner guide may have grooves shaped to receive fins of the upper portion, where the fins are slidable along the grooves. The components may be reversed such that the grooves are on the upper portion and the fins are on the inner guide. Other sliding engagement arrangements may be used, such as other rails, an elongated member running through an enclosed channel, or any other suitable sliding engagement arrangement.

In the illustrative embodiment of FIG. 45, the inner guide 823 may include grooves 760 that receive fins 314 that slide within the grooves 760 to allow the upper portion 821 to slidably move relative to the lower portion 822.

Figure 50A:
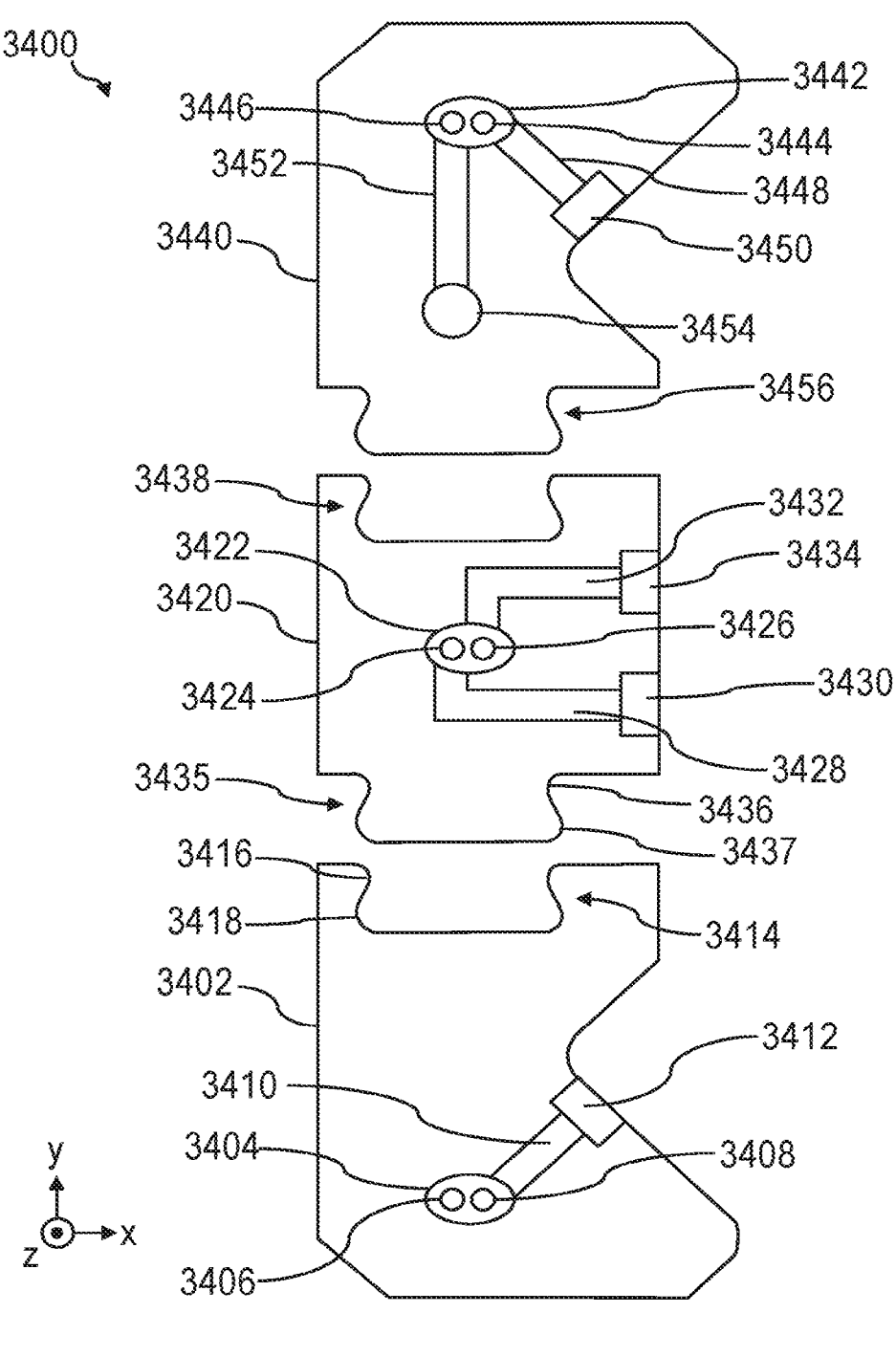
FIG. 50A is an exploded plan view of another embodiment of a transfer engine.

FIG. 50A is an exploded plan view of another embodiment of a transfer engine 3400. According to the embodiment of FIG. 50A, the transfer engine is modular, such that the number of fluid connections of the transfer engine may be increased or decreased to attach a desired number of containers. In the configuration shown in FIG. 50A, the transfer engine is configured to accommodate three containers. As shown in FIG. 50A, the transfer engine includes an inlet adapter 3402. The inlet adapter includes an inlet spike 3404 having a first inlet spike channel 3406 and a second inlet spike channel 3408. The first inlet spike channel 3406 may be fluidly connected to an air inlet, which may include a hydrophobic filter or check valve in some embodiments. The second inlet spike channel is connected to an inlet adapter fluid channel 3410, which allows fluid to flow from a connected container out of the inlet adapter. In the specific embodiment of FIG. 50A, the inlet adapter fluid channel 3410 terminates in an inlet fluid connector 3412 which in the depicted embodiment is configured to receive tubing. Of course, in other embodiments other fluid connectors may be employed, as the present disclosure is not so limited. The fluid arrangement of the inlet adapter 3402 allows air to be introduced into a container via the first inlet spike channel 3406 as fluid flows out of the inlet adapter fluid channel

3410 once the inlet spike pierces an inlet container. In some embodiments, the inlet adapter 3402 may include a check valve configured to allow unidirectional flow from the spike out through the inlet adapter fluid channel 3410. Such an arrangement may ensure fluid does not flow through the first inlet spike channel 3406 toward the air inlet.

According to the embodiment of FIG. 50A, the inlet adapter 3402 includes an inlet adapter coupling 3414 configured to allow the inlet adapter to releasably attach to other adapters (e.g., an intermediate adapter 3420). In particular, in the embodiment of FIG. 50A, the inlet adapter coupling is configured to releasably attach (e.g., interlock) the inlet adapter with the intermediate adapter 3420. The intermediate adapter coupling of FIG. 50A includes a collar 3416 and a pocket 3418, which is configured to receive a first intermediate adapter coupling 3435 having a corresponding shape. As will be discussed further with reference to FIG. 50B, when the first intermediate adapter coupling 3435 and inlet adapter coupling 3414 are engaged and interlocked, the intermediate adapter 3420 and inlet adapter may not be movable relative to one another in a first direction. In the specific example of FIG. 50A, when releasably interlocked, the intermediate adapter and inlet adapter may resist relative movement of one another in a plane (e.g., an x-y plane). However, when releasably interlocked, the inlet adapter coupling and intermediate adapter coupling may allow relative movement in a second direction (e.g., a z direction) to allow the adapters to be released from one another. According to the embodiment of FIG. 50A, the inlet adapter coupling is symmetric. In other embodiments, the inlet adapter may be irregularly shaped or have any suitable shape to allow the adapters to interlock, as the present disclosure is not so limited. In the embodiment of FIG. 50A, the inlet adapter coupling is configured to receive a corresponding coupling. In other embodiments, the inlet adapter coupling may be configured to be received in a corresponding coupling. In the embodiment of FIG. 50A, the inlet adapter coupling is separate and spaced from the inlet adapter fluid channel 3410, such that any physical interconnection and fluid connection are separate. Such an arrangement may be beneficial for simplicity of manufacturing and reliability of connection.

As shown in FIG. 50A, the intermediate adapter 3420 includes a first intermediate adapter coupling 3435. The first intermediate adapter coupling includes a neck 3436 and a tab 3437. The neck 3436 is configured to engage the collar 3416 of the inlet adapter coupling 3414. Similarly, the tab is configured to engage the pocket 3418 of the inlet adapter coupling. As will be discussed further with reference to FIG. 51, the arrangement of the neck, pocket, collar, and tab allow the adapters to be reliably interlocked with one another. As shown in FIG. 50A, the intermediate adapter also includes a second intermediate adapter coupling 3438. The second intermediate adapter coupling is configured to receive a correspondingly shaped coupling (e.g., an outlet adapter coupling 3456). In the embodiment of FIG. 50A, the first intermediate adapter coupling and the second intermediate adapter coupling are positioned on opposing sides of the intermediate adapter, though other configurations are contemplated as discussed further with reference to FIG. 54. In some embodiments as shown in FIG. 50A, the second intermediate adapter coupling may share the same shape and size as the inlet adapter coupling 3414. In such an arrangement the intermediate adapter 3420 may be interchanged or expanded with other copies of the intermediate adapter. That is, another intermediate adapter may be swapped in for the intermediate adapter 3420, or the other intermediate adapter may be used to expand the transfer engine 3400 (for example, see the exemplary embodiment of FIG. 52). A first intermediate adapter coupling (e.g., like first intermediate adapter coupling 3435) may be received in the second intermediate adapter coupling 3438. Accordingly, intermediate adapters may be added as desired to expand the number of spikes to correspond to a desired number of containers that may ultimately deliver a medicinal fluid to a patient.

As shown in FIG. 50A, the intermediate adapter 3420 includes an intermediate spike 3422 configured to pierce an intermediate container. The intermediate spike includes a first intermediate spike channel 3424 fluidly connected to a first intermediate fluid channel 3428. Similar to the inlet adapter, the first intermediate fluid channel terminates in an intermediate fluid connector 3430 (e.g., tubing connector). The intermediate spike also includes a second intermediate spike channel 3426 fluidly connected to a second intermediate fluid channel 3432. Like the first intermediate fluid channel, the second intermediate fluid channel also terminates in an intermediate fluid connector 3434 (e.g., tubing connector). According to the embodiment of FIG. 50A, and as will be discussed further with reference to FIG. 50B, the first intermediate fluid channel is configured to be fluidly connected to the inlet adapter fluid channel 3410 (e.g., via a tube). The second intermediate fluid channel is configured to be connected to an outlet adapter fluid channel 3448. Accordingly, the intermediate adapter is configured to form a fluid path from the inlet adapter to the outlet adapter. Like the inlet adapter 3402, the fluid channels of the intermediate adapter are separate from the first intermediate adapter coupling 3435 and the second intermediate adapter coupling 3438.

According to the embodiment of FIG. 50A, the transfer engine 3400 includes an outlet adapter 3440. The outlet adapter includes an outlet spike 3442 including a first outlet spike channel 3444 fluidly connected to an outlet adapter fluid channel 3448. Like the inlet adapter 3402 and the intermediate adapter 3420, the outlet adapter fluid channel terminates in an outlet fluid connector 3450 (e.g., tubing connector). The outlet spike also includes a second outlet spike channel 3446 fluidly connected to an outlet 3452. The outlet 3452 is connected to an infusion set coupling 3454 which may allow fluid from the transfer engine 3400 to ultimately flow to a patient. In other embodiments, an infusion set or other delivery device may connect directly to the outlet 3452, as the present disclosure is not so limited.

As shown in FIG. 50A, the outlet adapter 3440 includes an outlet adapter coupling 3456. In the embodiment of FIG. 50A, the outlet adapter coupling is configured to be received in the second intermediate adapter coupling 3438. The outlet adapter coupling has a size and shape matching that of the first intermediate adapter coupling 3435. Accordingly, if desired, the outlet adapter coupling may also be received in the inlet adapter coupling 3414 to releasably attach the outlet adapter to the inlet adapter. Such an arrangement may be beneficial where only two containers are to be connected to the transfer engine, such that the intermediate adapter 3420 may be omitted.

Figure 50B:
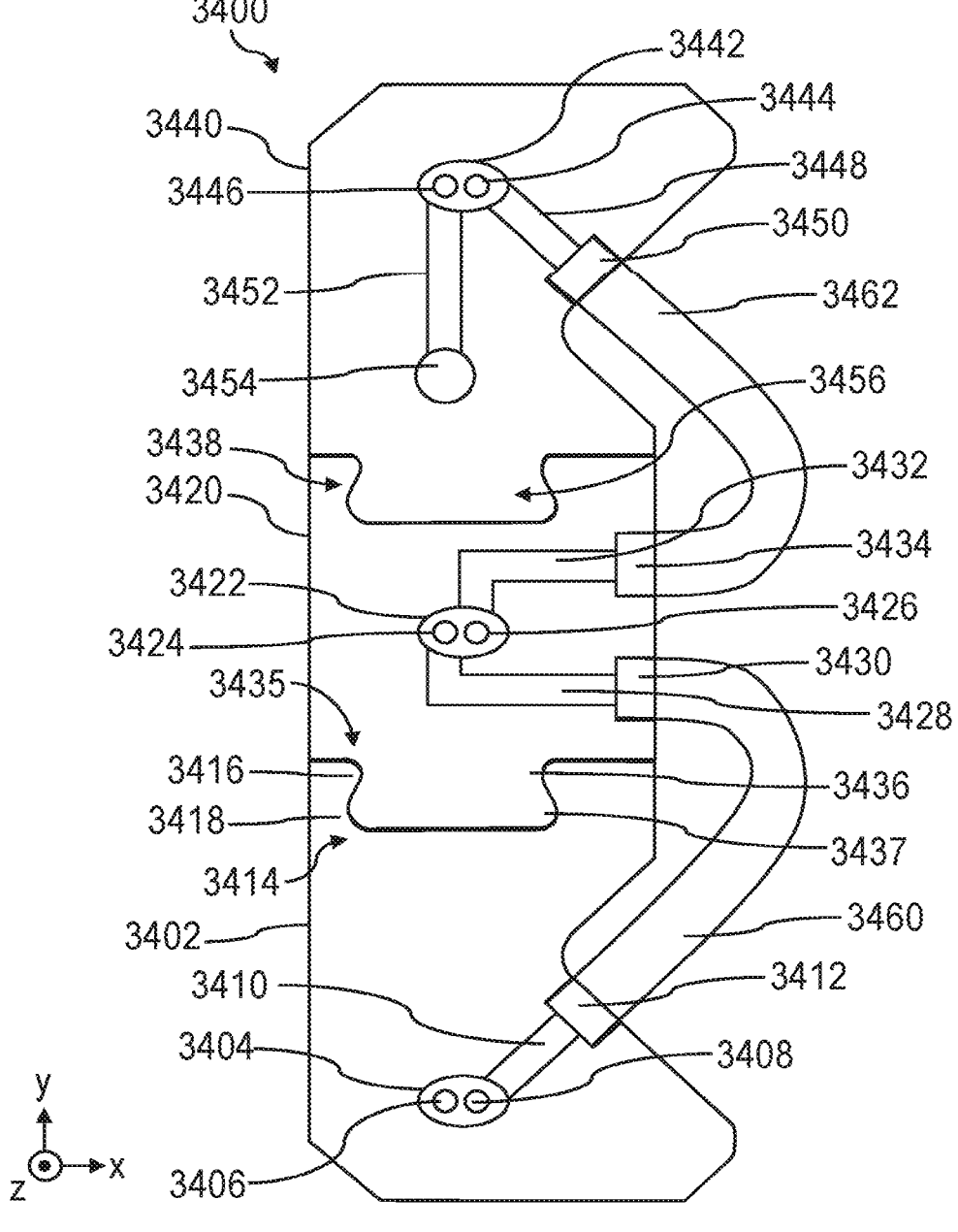
FIG. 50B is a plan view of the transfer engine of FIG. 50A.

FIG. 50B is a plan view of the transfer engine of FIG. 50A in an assembled configuration. As shown in FIG. 50B, the first intermediate adapter coupling 3435 is received in the inlet adapter coupling 3414. Accordingly, the collar 3416 engages the neck 3436 and the pocket 3418 engages the tab 3437. Thus, the inlet adapter 3402 is releasably interlocked with the intermediate adapter 3420. Likewise, as shown in FIG. 50B, the outlet adapter coupling 3456 is received in the second intermediate adapter coupling 3438, such that the intermediate adapter and outlet adapter 3440 are releasably interlocked. Accordingly, the inlet adapter, intermediate adapter, and outlet adapter are all physically connected to one another via the couplings.

Separately from the physical connections of the couplings, the adapters are fluidly connected so as to form a continuous fluid pathway between the inlet spike 3404, intermediate spike 3422, and outlet spike 3442, and ultimately the outlet 3452 so that fluid may be delivered to a patient via an infusion set or other delivery device (e.g., a syringe). As shown in FIG. 50B, the inlet adapter fluid channel 3410 is fluidly connected to the first intermediate fluid channel 3428 with a first tube 3460. The first tube is coupled to the inlet fluid connector 3412 and the first intermediate fluid connector 3430. The outlet adapter fluid channel 3448 is coupled to the second intermediate fluid channel 3432 with a second tube 3462. The second tube is coupled to the outlet fluid connector 3450 and the second intermediate fluid connector 3434. Accordingly, the inlet adapter, intermediate adapter, and outlet adapter are fluidly connected in a serial arrangement. In some embodiments, the fluid connectors may be quick connect tube connectors. In some embodiments, the adapters may include integrated tubes configured to interconnect the tubes of other adapters. In such an embodiment, quick connect fittings or other fittings may be employed. In other embodiments, any suitable connector may be employed to fluidly connect the adapters, as the present disclosure is not so limited.

It should be noted that while tubes and tube connectors are employed in the embodiment of FIG. 50B, any suitable fluid pathway may be employed to fluidly interconnect the various adapters. For example, tubing interconnecting the adapters may be rigid or flexible tubing. Additionally, in some embodiments, the adapter may include integrated fluid connectors and pathways separate from the couplings to allow for a fluid connection without additional components such as tubing.

In some embodiments, the transfer engine of FIGS. 50A-50B may be employed for reconstitution or pooling. In some embodiments, the intermediate adapter and/or outlet adapter may be configured to receive and connect a container containing a solid medicament (e.g., a lyophilized solid). In other embodiments, the intermediate adapter and/or outlet adapter may be configured to receive and connect a container containing a medicinal fluid. Any number of containers containing a solid medicament or medicinal fluid may be employed with a transfer engine according to embodiments described herein, as the present disclosure is not so limited.

It should be noted that while the spike channels and fluid channels are described and labeled separately in the embodiment of FIGS. 50A-50B, in other embodiments the spike channels and fluid channels may be considered a single component. For example, an adapter may be molded such that a fluid channel forms a spike channel.

As discussed previously, the modular transfer engine of FIGS. 50A-50B may be configured in a wide array of different configurations to accommodate a desired number of containers. For example, in some embodiments, the inlet adapter and outlet adapter may be employed together for delivering fluid from two containers (e.g., an inlet container and an outlet container). As another example, in some embodiments, the inlet adapter and outlet adapter may be employed with two intermediate adapters for delivering fluid from four containers (e.g., an inlet container, a first intermediate container, a second intermediate container, and an outlet container). In this manner, the number of adapters may be expanded and contracted as desired for any number of containers, including, but not limited to two containers, three containers, four containers, five containers, six containers, seven containers, and eight containers.

While in the embodiment of FIGS. 50A-50B the inlet adapter coupling is configured for receiving an intermediate adapter coupling or outlet adapter coupling as a socket, in other embodiments the arrangement may be reversed. That is, in some embodiments, an intermediate adapter coupling or outlet adapter coupling may be configured to receive an inlet adapter coupling. Put alternatively, an intermediate adapter coupling or outlet adapter coupling may be configured as a socket configured to receive a protruding inlet adapter coupling. In some embodiments, a coupling of an adapter may include a socket portion and a protruding portion, such that the coupling receives a corresponding protruding portion of another coupling and is also received in a corresponding socket portion of the other coupling. Thus, any suitable coupling may be employed whereby adapters can be physically connected to one another for any embodiment described herein, as the present disclosure is not so limited.

Figure 51:
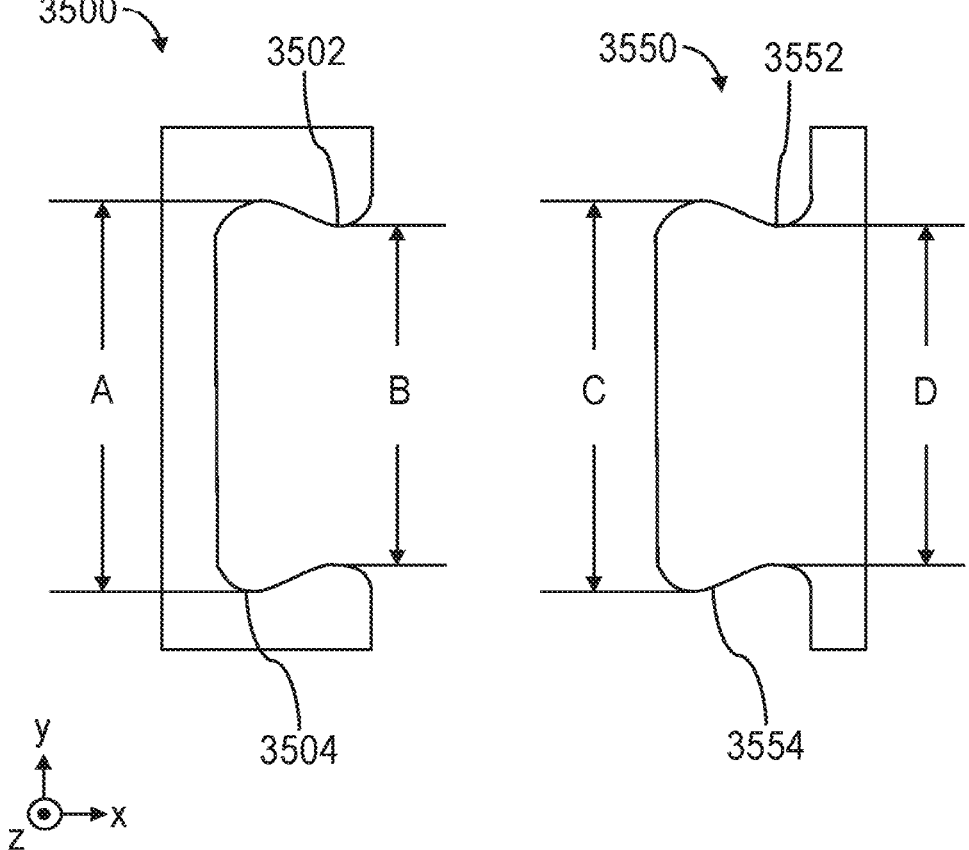
FIG. 51 is a schematic of one embodiment of a transfer engine adapter coupling.

FIG. 51 is a schematic of one embodiment of a transfer engine adapter coupling showing an exemplary mating engagement for securing adapters of a transfer engine together. As shown in FIG. 51, a first coupling 3500 is configured as a socket, and includes a collar 3502 and a pocket 3504. A second coupling 3550 is configured to be received in the first coupling 3500 and includes a neck 3552 and a tab 3554. As shown in FIG. 51, the shape and the size of the first coupling matches that of the second coupling. The tab 3554 is configured to be received in the pocket 3504, and the collar 3502 is configured to engage the neck 3552. As shown in FIG. 51, the collar 3502 and neck 3552 have widths less than the widths of the pocket 3504 and tab 3554. In particular, the pocket 3504 has a pocket width A, the collar 3502 has a collar width B, the tab 3554 has a tab width C, and the neck 3552 has a neck width D. The pocket width A is approximately equal to the tab width C, where the tab width is slightly smaller than the pocket width (e.g., within 1% of the pocket width) to allow the tab to fit within the pocket. Likewise, the collar width B is approximately equal to the neck width D, where the neck width is slightly smaller than the collar width (e.g., within 1% of the collar width) to allow the neck to fit within the collar. The pocket width A is greater than the collar width B (i.e., the collar width B is less than the pocket width A). Likewise, the tab width C is greater than the neck width D (i.e., the neck width D is less than the tab width C). Accordingly, when the second coupling is received in the first coupling, the couplings are not able to move relative to one another in a plane (e.g., an x-y plane). However, the couplings are able to move relative to each other in a second direction (e.g., a z-direction), which in the depicted embodiment is perpendicular to the plane. In other embodiments, the couplings may be prevented from moving relative to one another in a first direction and may be able to move relative to one another in a second direction. In some embodiments, the second direction may be transverse (e.g., perpendicular) to the first direction.

It should be noted that while one embodiment of a coupling is shown in FIG. 51, in other embodiments other couplings may be employed. For example, a coupling pair employed to physically connect multiple adapters may be a mortise and tenon. T-slot and T-slot adapter, or any other suitable coupling. In some embodiments, a coupling may include poka-yoke tabs configured to assist a user in aligning and connecting multiple adapters. In some embodiments, couplings may have a shape configured to control a directionality of a transfer engine formed by multiple adapters. For example, in some embodiments, adapter couplings may be able to connect in a single orientation.

Figure 52:
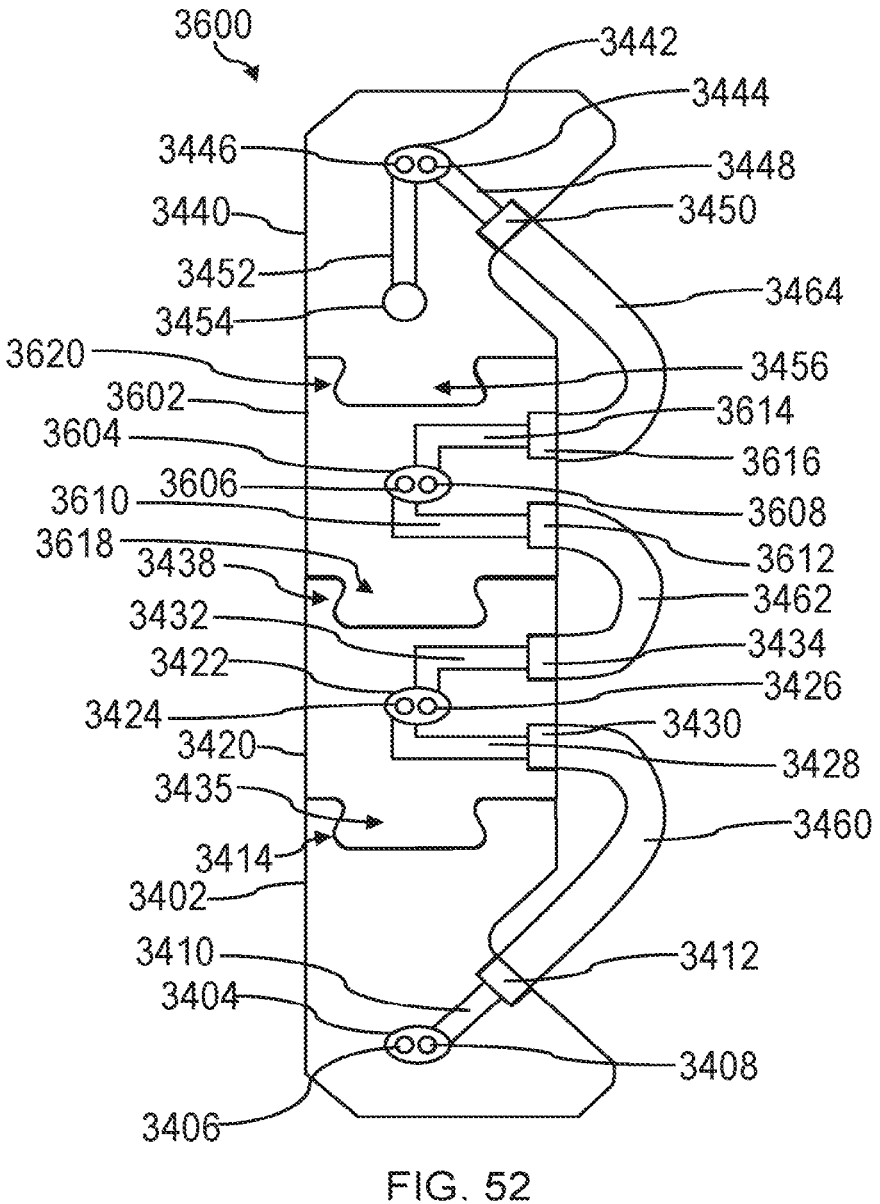
FIG. 52 is a plan view of another embodiment of a transfer engine.

FIG. 52 is a plan view of another embodiment of a transfer engine 3600. According to the embodiment of FIG. 52, the transfer engine is like that of FIGS. 50A-50B, except that a second intermediate adapter 3602 has been added to allow the transfer engine to connect to four containers. That is, the transfer engine includes an inlet adapter 3402, a first intermediate adapter 3420, and an outlet adapter 3440 having a configuration like that of FIGS. 50A-50B. In the embodiment of FIG. 52, the second intermediate adapter 3602 is identical to the first intermediate adapter. That is, the second intermediate adapter includes a second intermediate spike 3604 having a third intermediate spike channel 3606 connected to a third intermediate fluid channel 3610 and a fourth intermediate spike channel 3608 connected to a fourth intermediate fluid channel 3614. The third intermediate fluid channel 3610 and fourth intermediate fluid channel 3614 terminate in intermediate fluid connectors 3612, 3616 (e.g., tube connectors). The second intermediate adapter also includes a third intermediate adapter coupling 3618 and a fourth intermediate adapter coupling 3620. The third intermediate adapter coupling 3618 is received in the second intermediate adapter coupling 3438. The fourth intermediate adapter coupling receives the outlet adapter coupling 3456. Accordingly, the second intermediate adapter coupling may be releasably attached and/or interlocked with the second intermediate adapter coupling and outlet adapter coupling in a serial configuration. According to the embodiment of FIG. 52, the second intermediate adapter coupling is interchangeable with the first intermediate adapter coupling. Accordingly, if desired, the third intermediate adapter coupling may be received in the inlet adapter coupling 3414. Correspondingly, in some embodiments, the fourth intermediate adapter coupling may receive the first intermediate adapter coupling 3435.

As shown in FIG. 52, the fluid connections between the adapters are made with tubes, similar to FIG. 50B. In particular, a first tube 3460 fluidly connects an inlet adapter fluid channel 3410 to a first intermediate fluid channel 3428. A second tube 3462 fluidly connects a second intermediate fluid channel 3432 with the third intermediate fluid channel 3610. Finally, a third tube 3464 fluidly connects the fourth intermediate fluid channel 3614 to an outlet adapter fluid channel 3448. As discussed previously with reference to FIGS. 50A-50B, in FIG. 52 the physical connections between the adapters via the couplings are separate and/or spaced from the fluid connections between the adapters.

In the embodiment of FIG. 52, the various adapters are fluidly connected and physically connected in a serial arrangement. In other embodiments, the adapters may be fluidly connected or physically connected in a parallel arrangement. For example, in some embodiments the inlet adapter, first intermediate adapter, and second intermediate adapter may all be fluidly connected to the outlet adapter. For example, tubing from each of the inlet adapter, first intermediate adapter, and second intermediate adapter may join at a Y-junction into the outlet adapter fluid channel 3448. In such an embodiment, the first intermediate fluid channel 3428 and the third intermediate fluid channel 3610 may function as air inlets. For embodiments in which one or more fluid channels are configured as inlets, the fluid channels may include check valves configured to allow entrance of air into a respective fluid channel but inhibit escape of fluid via the respective fluid channel. In some other embodiments, the fluid channels may include hydrophobic filters configured to allow entrance of air into a respective fluid channel but inhibit escape of fluid via the respective fluid channel. In the embodiment of FIG. 52, the first intermediate fluid channel 3428 and the third intermediate fluid channel 3610 may include check valves to allow air to pass into the channels, but not allow fluid to flow out of the channels. Of course, any suitable parallel, serial, or combination of parallel and serial fluid configuration may be employed for delivering a medicinal fluid from a transfer engine, as the present disclosure is not so limited. Additional examples of a fluid configuration with a combination of parallel and serial flow paths will be discussed with reference to the exemplary embodiment of FIG. 53.

According to exemplary embodiments described herein, any suitable number of check valves may be employed in one or more fluid channels of an adapter, as the present disclosure is not so limited. The check valves may ensure unidirectional flow of fluid from the adapter, regardless of whether a fluid channel is employed as an air inlet or not. In cases where a fluid channel is an air inlet, a check valve may inhibit escape of fluid via the air inlet while allowing air to vent an attached container. However, in alternative cases where the fluid channel is a fluid inlet, the check valve may enforce unidirectional flow. In this manner, in some embodiments an adapter may include at least one check valve in a fluid channel such that the adapter may be modularly employed in a configuration with an air inlet or in a configuration with a fluid inlet. Of course, any suitable arrangement of or number of check valves may be employed in an adapter, as the present disclosure is not so limited.

Figure 53:
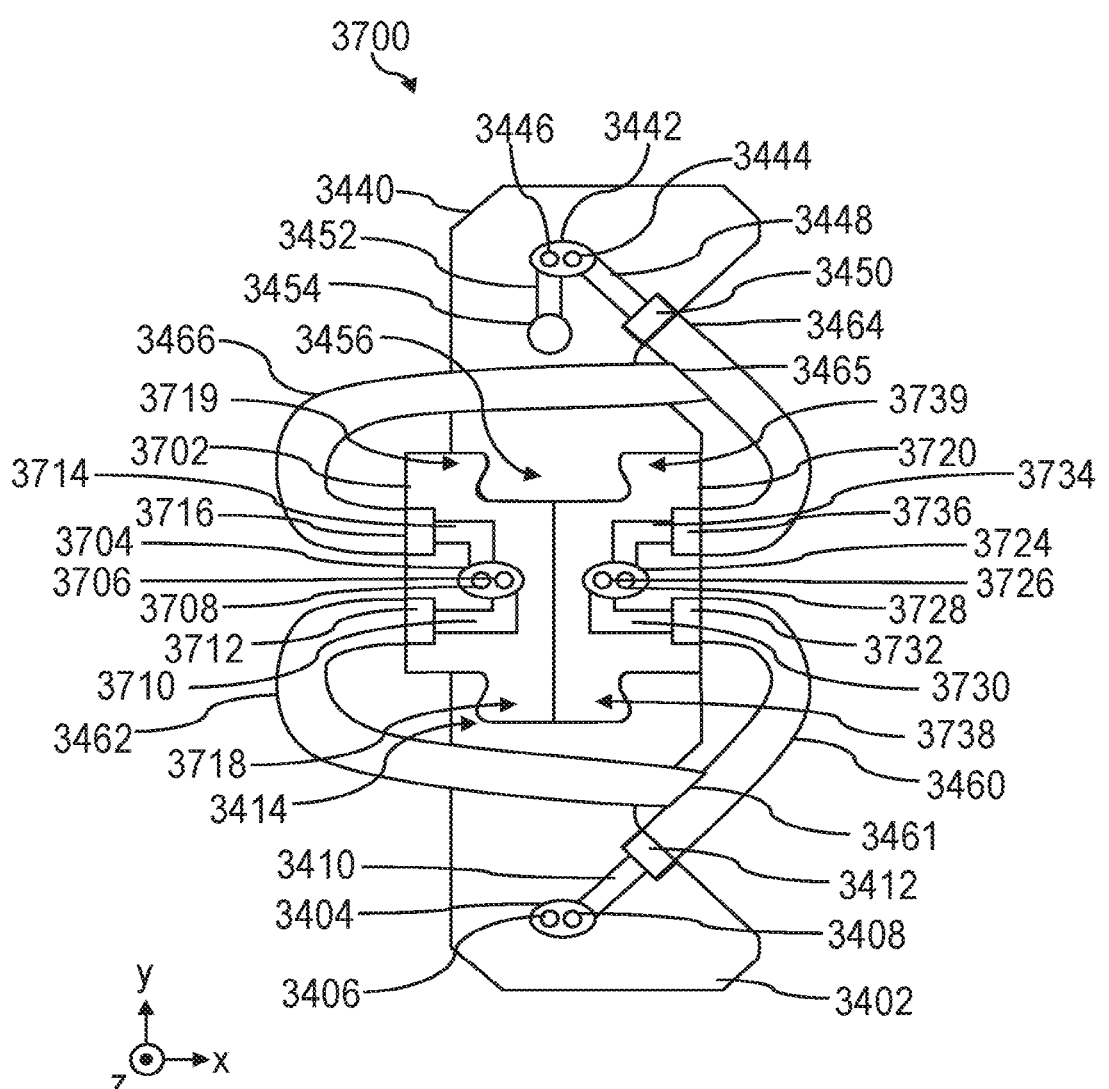
FIG. 53 is a plan view of another embodiment of a transfer engine.

FIG. 53 is a plan view of another embodiment of a transfer engine 3700 including multiple intermediate couplings configured to expand the container capacity of a transfer engine while maintaining a physically compact footprint. According to the embodiment of FIG. 53, the transfer engine includes an inlet adapter 3402 and an outlet adapter 3440 that have configurations as described with reference to the embodiment of FIGS. 50A-50B. As shown in FIG. 53, the transfer engine includes a first intermediate adapter 3702 and a second intermediate adapter 3720. In the embodiment of FIG. 53, the first intermediate adapter and second intermediate adapter are mirror images of each other (e.g., across the y-axis) and are generally configured to provide two spikes in the space of a single intermediate adapter like that shown in and described with reference to FIGS. 50A-50B. The first and second intermediate adapters are configured to releasably attach to the inlet adapter and the outlet adapter concurrently.

As shown in FIG. 53, the first intermediate adapter 3702 includes a first intermediate spike 3704 having a first intermediate spike channel 3706 and a second intermediate spike channel 3708. The first intermediate spike channel is fluidly connected to a first intermediate fluid channel 3710. The second intermediate spike channel is fluidly connected to a second intermediate fluid channel 3714. The first intermediate spike channel and the second intermediate spike channel each terminate in intermediate fluid connectors 3712, 3716. Finally, the first intermediate adapter includes a first intermediate adapter coupling 3718 and a second intermediate adapter coupling 3719. According to the embodiment of FIG. 53, the first intermediate adapter coupling is received in an inlet adapter coupling 3414. The first intermediate adapter coupling is configured to be received in a first side of the inlet adapter coupling, such that the first intermediate adapter coupling occupies at least a portion of the inlet adapter coupling (e.g., half of the inlet adapter coupling). The second intermediate adapter coupling 3719 receives an outlet adapter coupling 3456. Like the first intermediate adapter coupling, the second intermediate adapter coupling is configured to receive a first portion of the outlet adapter coupling. Specifically, in the embodiment of FIG. 53, the second intermediate adapter is configured to receive at least a portion of the outlet adapter coupling (e.g., half of the outlet adapter coupling). Of course, in other embodiments, the first intermediate adapter coupling and second intermediate adapter coupling may engage any portion of corresponding couplings, as the present disclosure is not so limited.

As shown in FIG. 53, the second intermediate adapter 3720 is a mirror image (e.g., across the y-axis) of the first intermediate adapter 3702. Accordingly, the second intermediate adapter includes the same components as the first intermediate adapter. The second intermediate adapter 3720 includes a second intermediate spike 3724 having a third intermediate spike channel 3726 and a fourth intermediate spike channel 3728. The third intermediate spike channel is fluidly connected to a third intermediate fluid channel 3730. The fourth intermediate spike channel is fluidly connected to a fourth intermediate fluid channel 3734. The third intermediate spike channel and the fourth intermediate spike channel each terminate in intermediate fluid connectors 3732, 3736 (e.g., tube connectors). Finally, the second intermediate adapter includes a third intermediate adapter coupling 3738 and a second intermediate adapter coupling 3739. The third intermediate adapter coupling is received in the inlet adapter coupling 3414, and in the particular embodiment of FIG. 53 engages at least a portion of the inlet adapter coupling (e.g., half of the inlet adapter coupling). The fourth intermediate adapter coupling receives the outlet adapter coupling 3456, and in the particular embodiment of FIG. 53 receives at least a portion of the outlet adapter coupling (e.g., half of the outlet adapter coupling). Thus, together the first intermediate adapter and second intermediate adapter connect and releasably interlock with the inlet adapter and outlet adapter concurrently.

As shown in FIG. 53, the transfer engine 3700 is arranged in a partly serial and partly parallel fluid configuration. The inlet adapter is fluidly connected to both the first intermediate adapter and the second intermediate adapter via a first tube 3460 and a second tube 3462. The first tube and second tube are connected at a Y-junction 3461 and are fluidly connected to an inlet adapter fluid channel 3410. The outlet adapter is also fluidly connected to both the first intermediate adapter and the second intermediate adapter via a third tube 3464 and a fourth tube 3466. The third tube and fourth tube are connected at a second Y-junction 3465 and are fluidly connected to an outlet adapter fluid channel 3448. Accordingly, the intermediate adapters are not serially fluidly connected to one another and are instead connected in parallel between the inlet adapter and outlet adapter. However, fluid flow from the inlet adapter passes through the two intermediate adapters before reaching the outlet adapter, and in this manner the transfer engine has a serial fluid configuration between the inlet adapter, intermediate adapters, and outlet adapter.

While in the embodiment of FIG. 53 Y-junctions are employed to interconnect the various adapters, in other embodiments adapters may include multiple fluid channels or integrated fluid junctions to facilitate connection of multiple intermediate adapters in parallel. For example, an inlet adapter may include multiple fluid connectors (e.g., two tube connectors) so that the inlet adapter may accommodate multiple tubes, where the fluid connectors are both fluidly connected to an inlet adapter fluid channel. Accordingly, the inlet adapter may include an internal Y-junction such that direct tubes without Y-junctions may be used to interconnect the inlet adapter to two intermediate adapters. Likewise, the outlet adapter may also include multiple fluid connectors (e.g., two tube connectors) so that the outlet adapter may accommodate multiple tubes, where the fluid connectors are both fluidly connected to an outlet adapter fluid channel. An inlet adapter and outlet adapter may include any suitable number of fluid channels and corresponding fluid connectors so that any number of intermediate adapters may be connected in parallel, as the present disclosure is not so limited.

Figure 54:
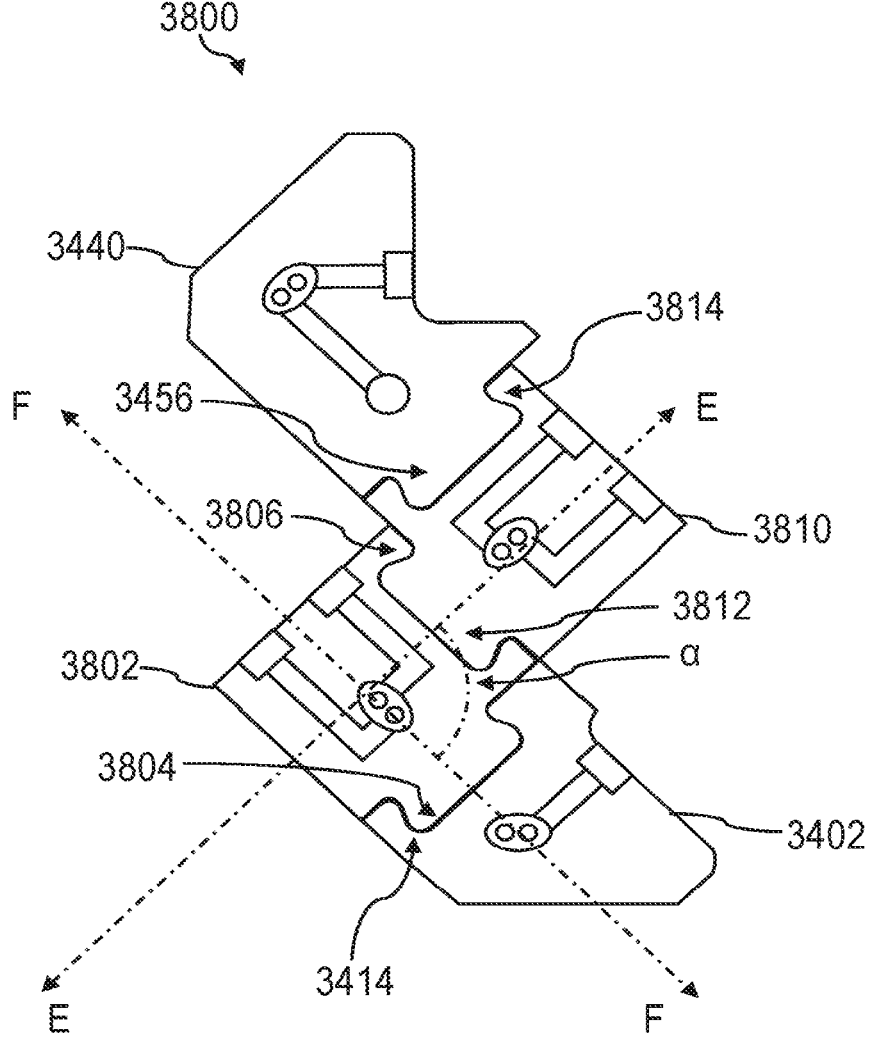
FIG. 54 is a plan view of another embodiment of a transfer engine.

FIG. 54 is a plan view of another embodiment of a transfer engine 3800 showing an alternative layout for adapters. In some cases, it may be desirable to reduce a footprint of adapters for a given number of containers, or it may be otherwise desirable to reduce a specific dimension of the transfer engine. For example, in the previously discussed embodiment of FIG. 54, the transfer engine is laid out in a linear pattern, which reduces an overall width of the transfer engine by having a longer length. However, to reduce an overall largest dimension (e.g., width or length), the adapters may be arranged in a zig-zag pattern as shown in FIG. 54. In the embodiment of FIG. 4, the fluid arrangement is similar to that of FIG. 52. That is, the transfer engine includes an inlet adapter 3402, a first intermediate adapter 3802, a second intermediate adapter 3810, and an outlet adapter 3440. The inlet adapter and outlet adapter are arranged like those of FIGS. 50A-50B. Likewise, the fluid arrangement of the first intermediate adapter and second intermediate adapter is like that of FIG. 52. However, in contrast to the embodiment of FIG. 52, the intermediate adapter couplings are angled relative to one another as discussed further below.

As shown in FIG. 54, the first intermediate adapter 3802 includes a first intermediate adapter coupling 3804 and a second intermediate adapter coupling 3806. The second intermediate adapter includes a third intermediate adapter coupling 3812 and a fourth intermediate adapter coupling 3814. The first intermediate adapter coupling 3804 is received in an inlet adapter coupling 3414. The second intermediate adapter coupling receives the third intermediate adapter coupling. Finally, the fourth intermediate adapter coupling receives the outlet adapter coupling 3456. As shown in FIG. 54, the first intermediate adapter coupling 3804 and the second intermediate adapter coupling 3806 are angled relative to one another. The first intermediate adapter coupling is aligned with a first axis E-E, and the second intermediate adapter coupling is aligned with a second axis F-F. The axes E-E and F-F are angled relative to each other at an angle $\alpha$. In the embodiment of FIG. 54, the angle between the first intermediate adapter coupling and the second intermediate adapter coupling is 90 degrees (e.g., $\alpha=90$ degrees), such that the couplings are orthogonal to each other. In other embodiments, the intermediate couplings may be angled at an acute angle relative to one another (e.g., $\alpha<90$ degrees). In still other embodiments, the intermediate couplings may be angled at an oblique angle relative to one another (e.g., $\alpha>90$ degrees). In the embodiment of FIG. 54, the third intermediate adapter coupling and fourth intermediate adapter coupling are angled relative to one another at an angle equal to that of the angle between the first and second intermediate adapter couplings. In some embodiments, the angle between the first and second intermediate adapter couplings may be different than the third and fourth intermediate adapter couplings.

Figure 55:
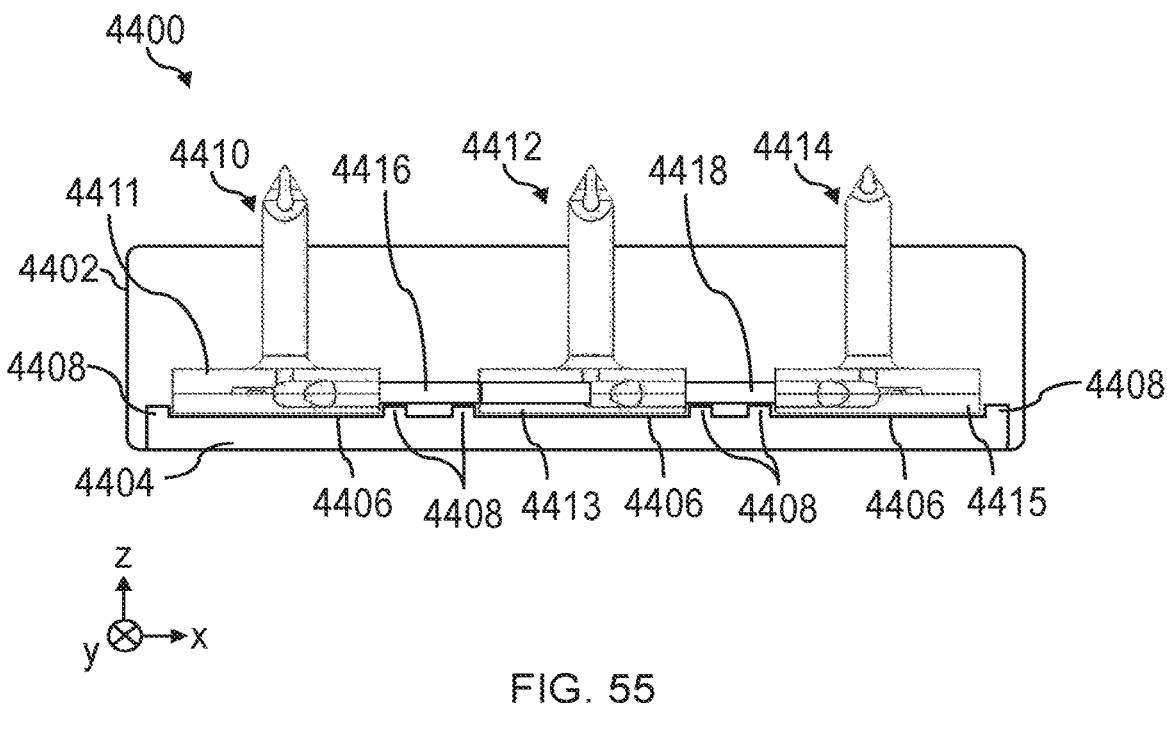
FIG. 55 is a side view of another embodiment of a medicinal fluid delivery device.

FIG. 55 is a side view of another embodiment of a medicinal fluid delivery device 4400. As shown in FIG. 55, the device includes a first adapter 4410 (e.g., an inlet adapter), a second adapter 4412 (e.g., an intermediate adapter), and a third adapter 4414 (e.g., an outlet adapter) connected in a serial fluid arrangement via first tube 4416 and second tube 4418. The adapters are all disposed in a lower portion 4402 of a housing. According to the embodiment of FIG. 55, the lower portion of the housing includes an adapter plate 4404 configured to physically couple the modular adapters together. The adapter plate 4404 may be integrally formed with the lower portion 4402 or formed as a separate component. As shown in FIG. 55, the adapter plate 4404 includes a plurality of depressions 4406 formed by studs 4408. Together the depression and studs are sized and shaped to receive the adapters and inhibit relative movement therebetween. The studs 4408 are configured to engage a first adapter base 4411, a second adapter base 4413, and a third adapter base 4415 (e.g., via an interference fit) to inhibit relative movement between the adapters. In some embodiments as shown in FIG. 55, the studs are configured to engage the sides of the adapter bases. In this manner, the bases of the adapters are couplings which releasably connect to one another via the adapter plate 4404 and are unable to move relative to one another in first direction (e.g., an x-y plane). Of course, while in the embodiment of FIG. 55 the studs 4408 engage the sides of the adapter bases, in other embodiment studs may engage any suitable portion of the adapter. For example, in some embodiments, an adapter base may include an adapter depression (e.g., a tenon) configured to receive a stud. In some embodiments, an adapter base may include a stud configured to be received in a depression of the adapter plate. Of course, any suitable number of studs and depressions may be employed on the adapter base and adapter plate as couplings so that multiple adapters may be releasably connected to one another, as the present disclosure is not so limited. Additionally, while the embodiment of FIG. 55 includes three adapters, any suitable number of adapters may be employed in an arrangement similar to that of FIG. 55. Likewise, while the embodiment of FIG. 55 includes adapters in a serial arrangement, any suitable fluid or physical arrangement may be employed (e.g., matrixed, zig-zagged, etc.), as the present disclosure is not so limited.

Figure 56:
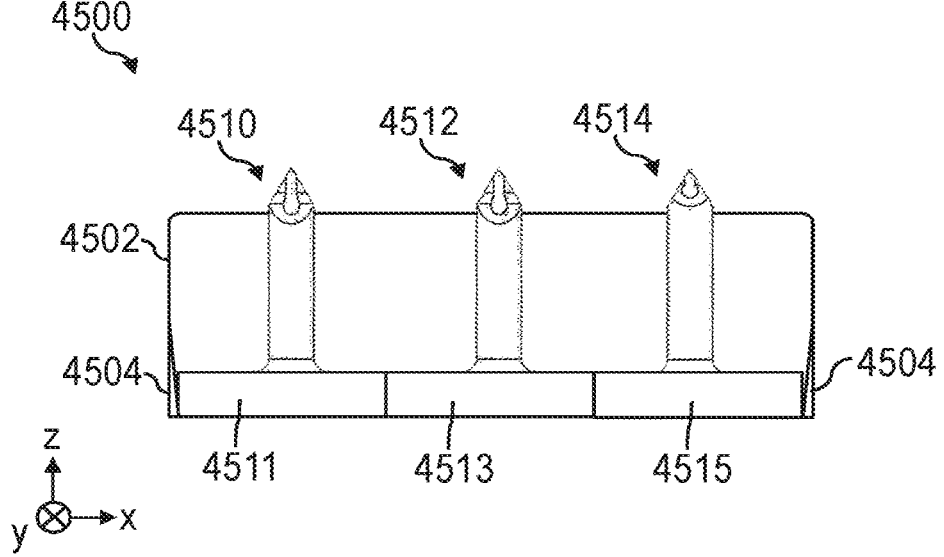
FIG. 56 is a side view of another embodiment of a medicinal fluid delivery device.

FIG. 56 is a side view of another embodiment of a medicinal fluid delivery device 4500. As shown in FIG. 56, the device includes a first adapter 4510 (e.g., an inlet adapter), a second adapter 4512 (e.g., an intermediate adapter), and a third adapter 4514 (e.g., an outlet adapter). The fluid connection of the adapters is not shown in FIG. 56, but the adapters may be fluidly connected in a serial arrangement, parallel arrangement, or any other suitable configuration for delivering the contents of three containers. The adapters are all disposed in a lower portion 4502 of a housing. According to the embodiment of FIG. 56, the lower portion of the housing is configured to form an interference fit with the adapters. In the depicted embodiment, the lower portion of the housing is configured to apply pressure to a first adapter base 4511 and a third adapter base 4515. In turn, the first adapter base and third adapter base 4515 are configured to apply pressure to a second adapter base 4513. Accordingly, the interference fit between the lower housing and the first adapter base 4511, second adapter base 4513, and third adapter base 4515 inhibits relative movement between the adapters via interference and friction. When in the configuration shown in FIG. 56, the adapters may not be able to move relative to one another in a first direction (e.g., an x-y plane). If a force greater than a threshold force is applied in a second direction (e.g., a z-direction), a frictional force may overcome such that an adapter may be moved relative to the other adapters in the second direction. Thus, in the embodiment of FIG. 56, the adapter bases 4511, 4513, 4515 function as couplings between the adapters in cooperation with the lower portion 4502 of the housing. In some embodiments as shown in FIG. 56, the lower portion 4502 includes lead-ins 4504 configured to guide the adapters into position and facilitate forming an interference fit between the lower portion and the adapters 4510, 4512, 4514. Of course, any suitable arrangement having an interference fit may be employed on the lower portion, including embodiments without lead-ins, as the present disclosure is not so limited. Additionally, while the embodiment of FIG. 56 includes three adapters, any suitable number of adapters may be employed in an arrangement similar to that of FIG. 56. Likewise, while the embodiment of FIG. 55 includes adapters in a serial physical arrangement, any suitable physical arrangement may be employed (e.g., matrixed, zig-zagged, etc.), as the present disclosure is not so limited.

FIG. 57 is a plan schematic of another embodiment of a transfer engine 4600. In the embodiment of FIG. 57. "I" is an inlet adapter, "M" is an intermediate adapter, and "O" is an outlet adapter as discussed according to exemplary embodiments described herein. The arrows depict a fluid path between the adapters. The relative positioning of the adapters depicts a physical arrangement of the transfer engine. In some embodiments, the adapters may include various couplings and/or cooperate with a lower portion of a housing to retain the adapters in the physical position depicted in FIG. 57. In the embodiment of FIG. 57, the physical arrangement is zig-zagged similar to that shown in FIG. 54. Additionally, the adapters are fluidly connected in a serial fluid arrangement, with fluid flowing sequentially from the inlet adapter, through the two intermediate adapters, and to the outlet adapter, where a medicinal fluid may be delivered to a user via a suitable delivery device.

FIG. 58 is a plan schematic of another embodiment of a transfer engine 4700. In the embodiment of FIG. 58, "I" is an inlet adapter. "M" is an intermediate adapter, and "O" is an outlet adapter as discussed according to exemplary embodiments described herein. The arrows depict a fluid path between the adapters. The relative positioning of the adapters depicts a physical arrangement of the transfer engine. In some embodiments, the adapters may include various couplings and/or cooperate with a lower portion of a housing to retain the adapters in the physical position depicted in FIG. 58. In the embodiment of FIG. 58, the physical arrangement is a rhomboid matrix. Additionally, the adapters are fluidly connected in a parallel fluid arrangement, with fluid flowing individually from the inlet adapter and two intermediate adapters to the outlet adapter. A resulting medicinal fluid may be delivered to a user via a suitable delivery device from the outlet adapter.

FIG. 59 is a plan schematic of another embodiment of a transfer engine 4800. In the embodiment of FIG. 59. "I" is an inlet adapter. "M" is an intermediate adapter, and "O" is an outlet adapter as discussed according to exemplary embodiments described herein. The arrows depict a fluid path between the adapters. The relative positioning of the adapters depicts a physical arrangement of the transfer engine. In some embodiments, the adapters may include various couplings and/or cooperate with a lower portion of a housing to retain the adapters in the physical position depicted in FIG. 59. In the embodiment of FIG. 59, the physical arrangement is a rhomboid matrix. Additionally, the adapters are fluidly connected in a partially parallel, partially serial fluid arrangement. In particular, fluid flows individually from two inlet adapters to a single intermediate adapter.

Then, fluid from the intermediate adapter to the outlet adapter. A resulting medicinal fluid may be delivered to a user via a suitable delivery device from the outlet adapter.

FIG. 60 is a plan schematic of another embodiment of a transfer engine 4900. In the embodiment of FIG. 60, "I" is an inlet adapter. "M" is an intermediate adapter, and "O" is an outlet adapter as discussed according to exemplary embodiments described herein. The arrows depict a fluid path between the adapters. The relative positioning of the adapters depicts a physical arrangement of the transfer engine. In some embodiments, the adapters may include various couplings and/or cooperate with a lower portion of a housing to retain the adapters in the physical position depicted in FIG. 60. In the embodiment of FIG. 60, the physical arrangement is a square matrix. Additionally, the adapters are fluidly connected in serial fluid arrangement like that of FIG. 57. In particular, fluid flows sequentially from the inlet adapter, through the two intermediate adapters, and to the outlet adapter. A resulting medicinal fluid may be delivered to a user via a suitable delivery device from the outlet adapter.

While exemplary embodiments described herein are arranged in linear, angled, and matrixed patterns, in other embodiments, a transfer engine may be arranged in a square matrix, a hexagonal pattern, or any other suitable geometric pattern, as the present disclosure is not so limited. In some embodiments, an adapter may include any number of couplings so that multiple transfer engines may be arranged in a desired matrix. For example, an adapter may include one coupling, two couplings, three couplings, four couplings, or any other suitable number of couplings. In some embodiments, an inlet adapter may include a first inlet adapter coupling and a second inlet adapter coupling, where the first and second inlet adapter couplings are each configured to connect to a separate intermediate adapter coupling in a parallel configuration. Such an arrangement may provide a fluid arrangement similar to that in the embodiment of FIG. 53, although other fluid configurations are contemplated. In some embodiments, an outlet adapter may include a first outlet adapter coupling and a second outlet adapter coupling, where the first and second outlet adapter couplings are each configured to connect to a separate intermediate adapter coupling in a parallel configuration.

Figure 61A:
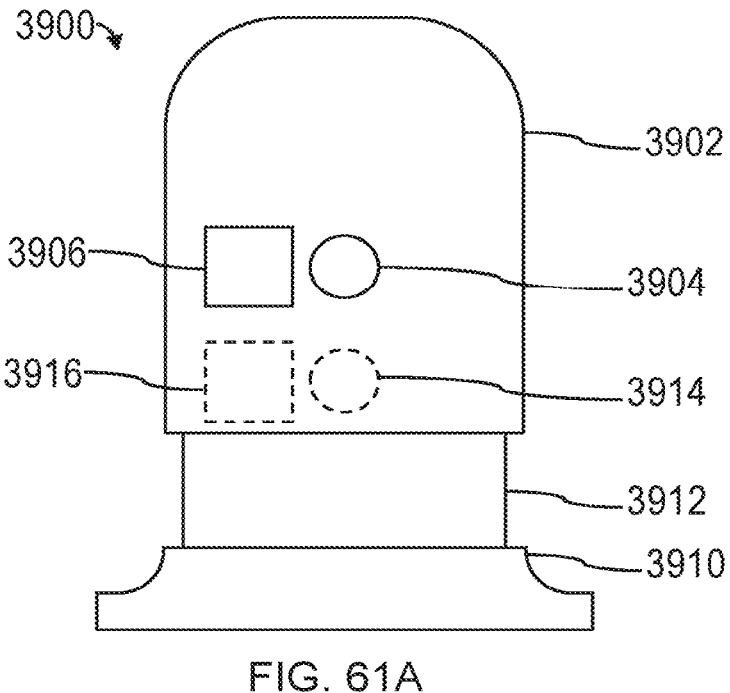
FIG. 61A is a front side schematic of another embodiment of a medicinal fluid delivery device in a first state.
Figure 61B:
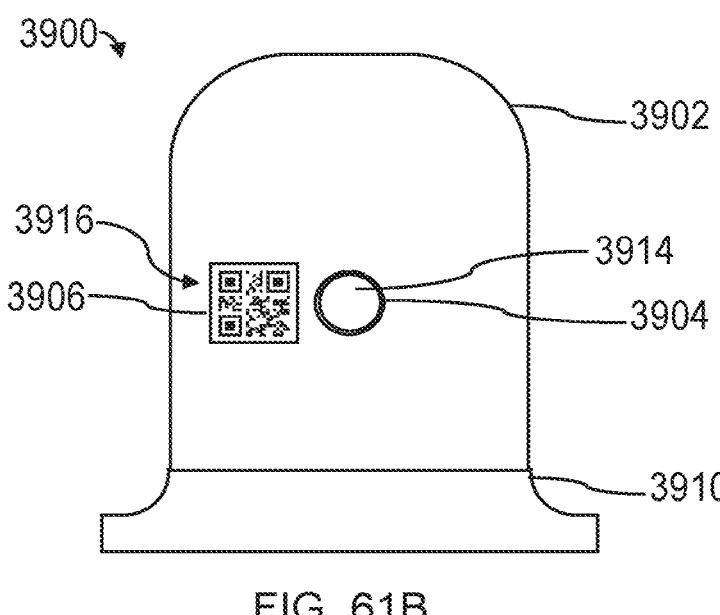
FIG. 61B is a front side schematic of the medicinal fluid delivery device of FIG. 61A in a second state.

FIG. 61A is a front side schematic of another embodiment of a medicinal fluid delivery device 3900 in a first state and FIG. 61B shows the medicinal fluid delivery device in a second state. According to the embodiment of FIGS. 61A-61B, the device includes a housing having an upper portion 3902 and a lower portion 3910. The housing is configured to receive a single container, though in other embodiments any suitable number of containers may be disposed within the housing. The upper portion is configured to move between an unactuated position shown in FIG. 61A and an actuated position shown in FIG. 61B. As in some previously discussed embodiments, the upper portion is configured to slide along an inner guide 3912. The upper portion includes a fluid outlet cutout 3904 configured to reveal and allow physical access to a fluid outlet when the upper portion is moved to the actuated position. In the embodiment of FIGS. 61A-61B, the cutout 3904 is configured to align with a fluid outlet 3914 when the upper portion is in the actuated position. Of course, any arrangement for selectively allowing access to a fluid outlet may be employed according to other exemplary embodiments described herein. In some alternative embodiments, the fluid outlet may be physically accessible regardless of the state of the upper portion 3902, as the present disclosure is not so limited.

The embodiment of FIGS. 61A-61B includes a marker configured to selectively communicate information to a remote device (e.g., a user device such as a smartphone). In the embodiment of FIGS. 61A-61B, the marker is a QR code 3916 disposed on the lower portion 3910 of the housing. In some embodiments as shown in FIGS. 61A-61B, the QR code is at least partially obstructed by the upper portion when the upper portion is in the unactuated position. In particular, the QR code is hidden and not visible when the upper portion is in the unactuated position, as an opaque portion of the upper portion obscures the marker. In the actuated position, however, a marker window 3906 formed in the upper portion aligns with the QR code to expose the QR code to a user, resulting in the QR code being accessible. Accordingly, once the medicinal fluid delivery device is actuated, a user may scan the QR code with a remote device. The QR code may relay information to the remote device when scanned, such as dosage, drug lot information, etc. That is, the QR code may include information that is readable by the remote device. In some embodiments, the marker window 3906 may be formed as a hole in the upper portion. In some embodiments, the marker window 3906 may be a transparent portion of the upper portion that is configured to align with the marker when the upper portion is in the actuated position. Of course, the QR code may be made accessible to a user with any suitable arrangement, as the present disclosure is not so limited. For example, in some embodiments, the upper portion may cover at least a portion of the marker in the unactuated position and uncover the marker in the actuated position without a window. The arrangement of FIGS. 61A-61B may allow information to be transferred to a remote device without pairing or a power source stored onboard the medicinal fluid delivery device.

Figure 62A:
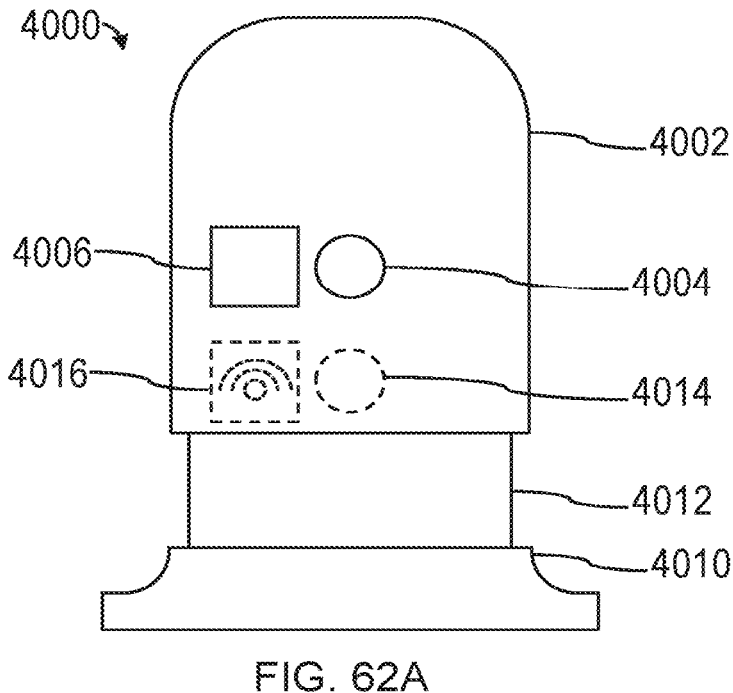
FIG. 62A is a front side schematic of another embodiment of a medicinal fluid delivery device in a first state.
Figure 62B:
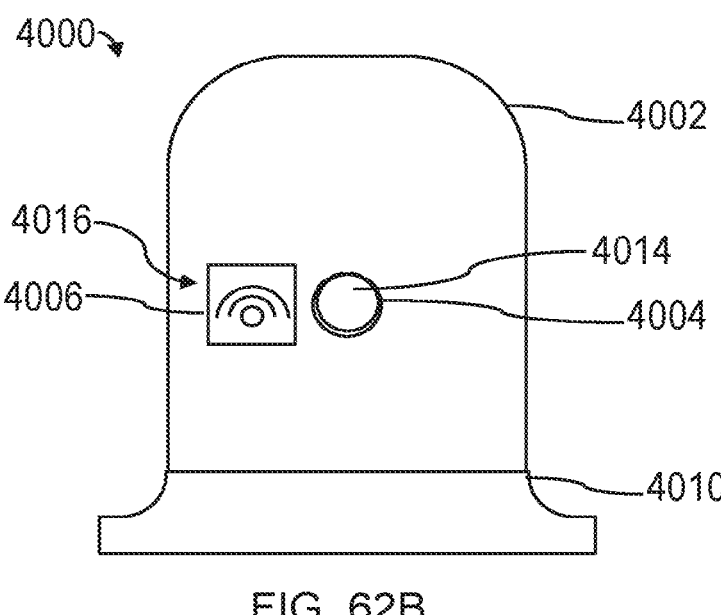
FIG. 62B is a front side schematic of the medicinal fluid delivery device of FIG. 62A in a second state.

FIG. 62A is a front side schematic of another embodiment of a medicinal fluid delivery device 4000 in a first state and FIG. 62B shows the medicinal fluid delivery device in a second state. According to the embodiment of FIGS. 62A-62B, the device includes a housing having an upper portion 4002 and a lower portion 4010. The housing is configured to receive a single container, though in other embodiments any suitable number of containers may be disposed within the housing. The upper portion is configured to move between an unactuated position shown in FIG. 62A and an actuated position shown in FIG. 62B. As in previously discussed embodiments, the upper portion is configured to slide along an inner guide 4012. The upper portion includes a fluid outlet cutout 4004 configured to reveal and allow physical access to a fluid outlet when the upper portion is moved to the actuated position. In the embodiment of FIGS. 62A-62B, the cutout 4004 is configured to align with a fluid outlet 4014 when the upper portion is in the actuated position. Of course, any arrangement for selectively allowing access to a fluid outlet may be employed according to other exemplary embodiments described herein.

The embodiment of FIGS. 62A-62B includes a marker configured to selectively communicate information to a remote device. In the embodiment of FIGS. 62A-62B, the marker is an NFC tag 4016 disposed on the lower portion 4010 of the housing. As shown in FIGS. 62A-62B, the NFC tag is enclosed by the upper portion in the unactuated position. In the actuated position, however, a marker window 4006 formed in the upper portion aligns with the NFC tag to reveal the NFC tag to a user, resulting in the NFC tag being accessible. In some embodiments, the upper portion may be formed of an NFC signal impeder or other radiofrequency (RF) shielding such that the NFC tag is at least partially obstructed by the upper portion when the upper portion is in the unactuated position. According to such an embodiment, the NFC tag may not be activated by a remote device until the NFC tag is aligned with the window, which may be radio transparent. In other embodiments, a visual indicator of where a user may read the NFC tag may be at least partially obstructed by the upper portion in the unactuated position. According to such an embodiment, the window may reveal a visual indicator of where a user may read an NFC tag. Accordingly, once the medicinal fluid delivery device is actuated, a user may scan the NFC tag with a remote device. The NFC tag may relay information to the remote device, such as dosage, drug lot information, etc. In some embodiments, the marker window 4006 may be formed as a hole in the upper portion. In some embodiments, the marker window 4006 may be a radio-transparent portion of the upper portion 4002. Of course, the NFC tag may be made accessible to a user with any suitable arrangement, as the present disclosure is not so limited. The arrangement of FIGS. 62A-62B may allow information to be transferred to a remote device without a power source stored onboard the medicinal fluid delivery device, as the NFC tag may be powered wirelessly by a remote device.

FIG. 63 is a flow chart of another embodiment of a medicinal fluid delivery process. As shown in step 4100, a first container is provided within a housing, where an upper portion of the housing at least partially encloses the first container. In step 4102, a force is applied to the upper portion to move the upper portion from an unactuated position to an actuated position. In some embodiments, moving the upper portion to the actuated position may pierce the first container. In step 4104, a marker is exposed when the upper portion is moved to the second actuated position. For example, a window formed in the upper portion may align with the marker. In some embodiments, moving the upper portion to the actuated position may also make a fluid outlet physically accessible, as discussed further according to other exemplary embodiments herein. In step 4106, fluid is allowed to flow from the first container to a fluid outlet. For example, as discussed previously, moving the upper portion to the actuated position may fluidly connect the first container to the fluid outlet (e.g., via a spike).

Figure 64A:
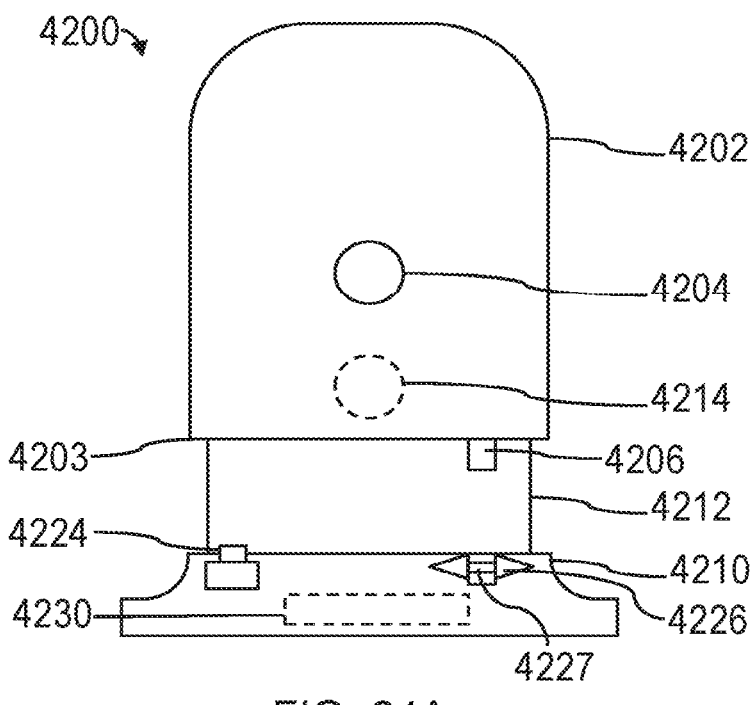
FIG. 64A is a front side schematic of another embodiment of a medicinal fluid delivery device in a first state.
Figure 64B:
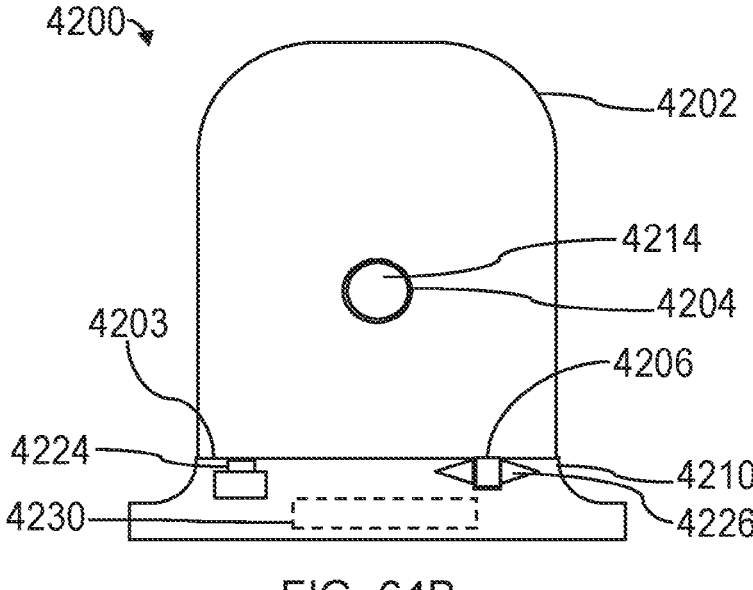
FIG. 64B is a front side schematic of the medicinal fluid delivery device of FIG. 64A in a second state.

FIG. 64A is a front side schematic of another embodiment of a medicinal fluid delivery device 4200 including a communication module in a first state, and FIG. 64B shows the medicinal fluid delivery device of FIG. 64A in a second state. According to the embodiment of FIGS. 64A-64B and similar to previously discussed embodiments, the device includes a housing having an upper portion 4202 and a lower portion 4210. The housing is configured to receive a single container, though in other embodiments any suitable number of containers may be disposed within the housing. The upper portion is configured to move between an unactuated position shown in FIG. 64A and an actuated position shown in FIG. 64B. As in previously discussed embodiments, the upper portion is configured to slide along an inner guide 4212. The upper portion includes a fluid outlet cutout 4204 configured to reveal and allow physical access to a fluid outlet when the upper portion is moved to the actuated position. In the embodiment of FIGS. 64A-64B, the cutout 4204 is configured to align with a fluid outlet 4214 when the upper portion is in the actuated position. Of course, any arrangement for selectively allowing access to a fluid outlet may be employed according to other exemplary embodiments described herein.

The embodiment of FIGS. 64A-64B includes a communication module 4230 and is configured to communicate with one or more remote devices (e.g., user devices). The communications and related functionality are similar to that discussed with reference to the embodiment of FIG. 18. The communication module will be discussed further with reference to FIG. 65. According to the embodiment of FIG. 64A-64B, the communication module may be easily attached to the lower portion 4210. The communication module may be self-contained such that a medicinal fluid delivery device may be easily made to communicate with remote devices when paired with a trigger.

According to the embodiment of FIG. 64A-64B, the medicinal fluid delivery device 4200 includes a trigger configured to activate the communication module 4230. Two examples of triggers are shown in the embodiment of FIGS. 64A-64B, which in other embodiments may be used alone. First, the device includes a switch 4224 (e.g., microswitch) which is configured to engage a engagement portion 4203 of the upper portion 4202 of the housing. The engagement portion 4203 of FIGS. 64A-64B is a lip, though in other embodiments the engagement portion may be a housing wall, internal projection or feature, or any other suitable feature of the upper portion 4202 of the housing. The switch is configured to be activated (e.g., depressed) when the upper portion moves to the actuated position. That is, the switch is configured to be moved from a first switch position to a second switch position by the upper portion. Secondly, the device includes a light beam sensor 4226 disposed in the lower portion 4210 that emits a light beam 4227. In particular, the light beam sensor includes a light beam transmitter and a light beam receiver, where the light beam transmitter is configured to emit a light beam received by the light beam receiver. The upper portion 4202 includes a projection 4206 configured to physically block the light beam when the upper portion is in the actuated position. The light beam sensor is configured to detect when the light beam is interrupted, thereby determining the upper portion is actuated. In some embodiments, a trigger of the medicinal fluid delivery device may connect the communication module 4230 to a power source. Once the communication module is activated by one or both triggers, the communication module may send one or more messages including information to a remote device. While two examples of triggers are shown in FIGS. 64A-64B, any suitable sensor may be employed to wake a communication module, as the present disclosure is not so limited. For example, a strain gauge or other pressure sensor may be disposed in the upper portion and may be configured to detect force or pressure applied to the upper portion by a user. When the detected force or pressure exceeds a threshold force or pressure, the communication module may be activated. As another example, a Hall Effect sensor may be employed to detect movement of the upper portion to the actuated position and wake the communication module, as discussed previously with reference to other exemplary embodiments herein. As still another example, a proximity sensor may be employed to detect movement of the upper portion to the actuated position and wake the communication module.

Figure 65:
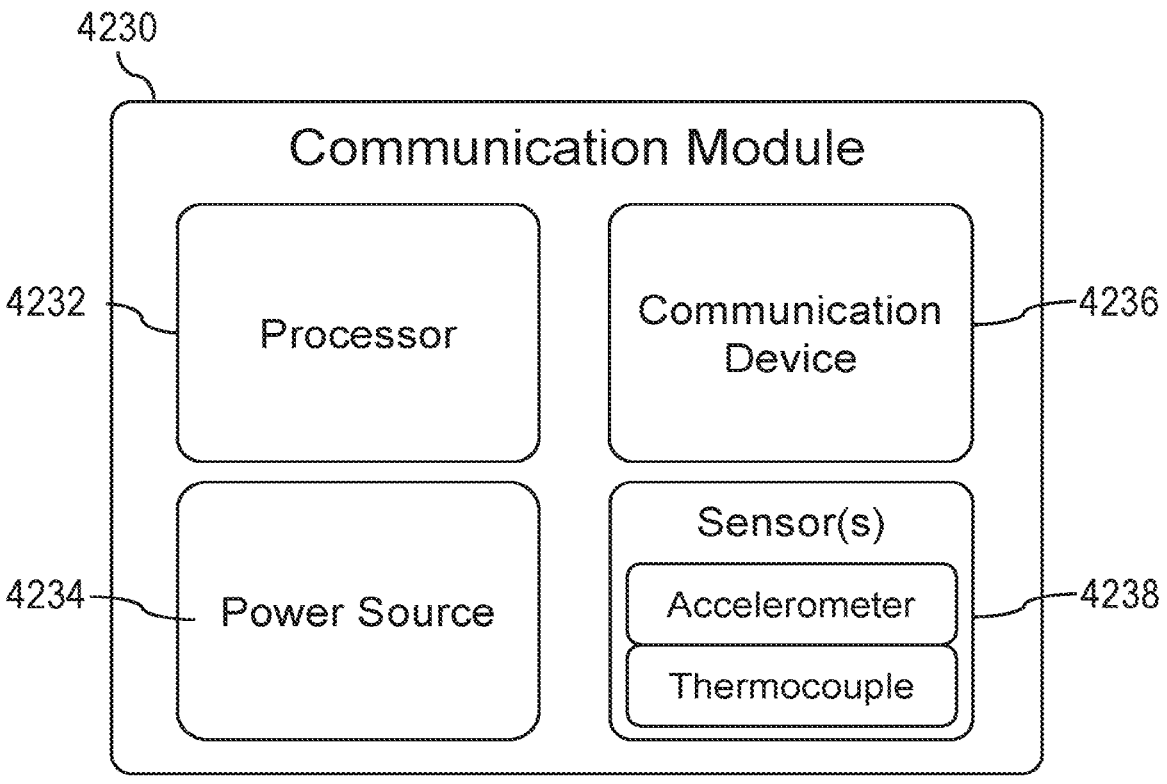
FIG. 65 is schematic of one embodiment of a communication module.

FIG. 65 is schematic of one embodiment of a communication module 4230. As shown in FIG. 65, the communication module includes a processor 4232 that may be configured to execute computer readable instructions stored in non-transitory memory. The communication module also includes a power source 4234 (e.g., a battery) configured to supply power to the various components of the communication module. The communication module also includes a communication device 4236 which may be a radio transceiver employing any suitable radio-frequency communication protocol (e.g., Bluetooth. Bluetooth Low-Energy, Wi- Fi, 802.15.4, ZigBee, GSM, HSPA, CDMA, etc.). In some embodiments as shown in FIG. 65, the communication module may optionally include one or more sensors 4238 that are configured to provide information to the communication module. The sensors may include an accelerometer configured to provide motion information to the communication module and a temperature sensor (e.g., a thermocouple) configured to provide temperature information to the communication module. Information from these sensors may be included in messages sent by the communication module to one or more remote devices. Of course, any suitable sensors may be employed as a part of a communication module, as the present disclosure is not so limited.

In some embodiments, a communication module may include additional components that may provide additional functionality to facilitate use of a medical delivery device. For example, in some embodiments, a communication module may include a vibratory motor configured to agitate the device. In some embodiments, the vibratory motor may be employed to assist with mixing various fluids and solids of the medical fluid delivery device. In some embodiments, the vibratory motor may be configured to provide a haptic alert to a user as discussed with reference to other embodiments described herein. As another example, in some embodiments, the communication module may include a speaker. In some embodiments, the speaker may be configured to provide an auditory alert to a user as discussed with reference to other embodiments described herein.

Figure 66:
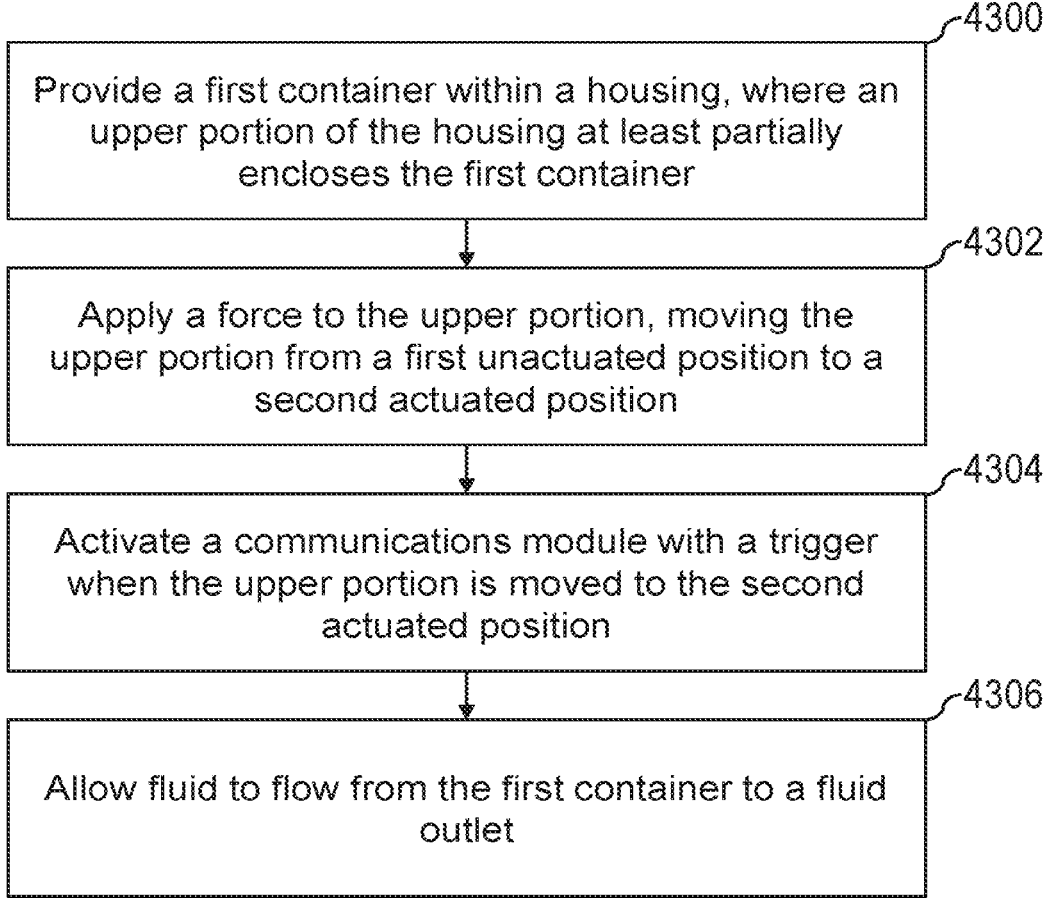
FIG. 66 is a flow chart of another embodiment of a medicinal fluid delivery process.

FIG. 66 is a flow chart of another embodiment of a medicinal fluid delivery process. As shown in step 4300, a first container is provided within a housing, where an upper portion of the housing at least partially encloses the first container. In step 4302, a force is applied to the upper portion to move the upper portion from an unactuated position to an actuated position. In some embodiments, moving the upper portion to the actuated position may pierce the first container. In step 4304, a communication module is activated with a trigger when the upper portion is moved to the actuated position. For example, a switch may be depressed by the upper portion when the upper portion is moved to the actuated position. In some embodiments, moving the upper portion to the actuated position may also make a fluid outlet physically accessible, as discussed further according to other exemplary embodiments herein. In step 4306, fluid is allowed to flow from the first container to a fluid outlet. For example, as discussed previously, moving the upper portion to the actuated position may fluidly connect the first container to the fluid outlet (e.g., via a spike).

It should be noted that while some of the embodiments above depict a reconstitution device, in other embodiments a device similar to these embodiments may be a medicinal fluid delivery device configured to pool medicinal fluids as opposed to reconstituting a solid medicament, or may be configured to access the contents of only a single container. Accordingly, the various features and methods described with reference to these embodiments are also applicable to a medicinal fluid delivery device configured for pooling fluids or for accessing the contents of only a single container, as the present disclosure is not so limited.

In addition to the above, it should be noted that while the devices of some of the devices discussed above are configured for accessing and delivering the contents of two containers, any suitable number of containers may be employed. For example, in some embodiments, a medicinal fluid delivery device like those described above may include a single container, two containers, three containers, four containers, five containers, or any suitable number of containers. Accordingly, the various features and methods described above are also applicable to a medicinal fluid delivery or reconstitution device having any number of containers, as the present disclosure is not so limited.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A reconstitution device comprising;
a first spike extending from a first base piece;
a second spike extending from a second base piece, wherein said first and second base pieces are coupled to one another via an interlocking arrangement;
an inlet in fluid communication with the first spike;
an outlet in fluid communication with the second spike;
a fluid pathway leading from the first spike to the second spike; and
a housing circumscribing the first base piece and the second base piece.

2. The reconstitution device of claim 1, wherein said first and second base pieces are coupled to one another via an intermediate piece.

3. The reconstitution device of claim 1, wherein the first base piece and second base piece are attached directly to each other.

4. The reconstitution device of claim 2, further comprising a third spike coupled to the intermediate piece.

5. The reconstitution device of claim 1, further comprising a check valve positioned in the fluid pathway.

6. The reconstitution device of claim 1, wherein the inlet is an air inlet.

7. The reconstitution device of claim 1, further comprising a hydrophobic filter at the inlet.

8. The reconstitution device of claim 1, further comprising:
a first sheath covering at least a portion of the first spike; and
a second sheath covering at least a portion of the second spike.

9. The reconstitution device of claim 1, wherein the housing has a lower portion and an upper portion in movable engagement with the lower portion, the upper portion being movable relative to the lower portion from an unactuated position and an actuated position.

10. The reconstitution device of claim 9, further comprising a first container aligned with the first spike and a second container aligned with the second spike, wherein the first spike is configured to spike the first container and the second spike is configured to spike the second container when the upper portion of the housing is moved to the actuated position.

11. The reconstitution device of claim 10, wherein the second container contains a vacuum such that fluid in the first container is at a higher pressure than a pressure of an interior of the second container.

12. The reconstitution device of claim 9, wherein the outlet is movable relative to the housing.

* * * * *